US010428062B2

(12) United States Patent
Acharya et al.

(10) Patent No.: US 10,428,062 B2
(45) Date of Patent: Oct. 1, 2019

(54) GEMINAL SUBSTITUTED AMINOBENZISOXAZOLE COMPOUNDS AS AGONISTS OF α7-NICOTINIC ACETYLCHOLINE RECEPTORS

(71) Applicant: Forum Pharmaceuticals, Inc., Waltham, MA (US)

(72) Inventors: Raksha Acharya, Bedford, MA (US); Duane A. Burnett, Wayland, MA (US); Matthew Gregory Bursavich, Needham, MA (US); Andrew Simon Cook, Stow, MA (US); Bryce Alden Harrison, Framingham, MA (US); Andrew J. McRiner, Melrose, MA (US)

(73) Assignee: Axovant Sciences GmbH, Basel (CH)

( * ) Notice: Subject to any disclaimer, the term of this patent is extended or adjusted under 35 U.S.C. 154(b) by 0 days.

(21) Appl. No.: 15/233,664

(22) Filed: Aug. 10, 2016

(65) Prior Publication Data
US 2017/0044155 A1     Feb. 16, 2017

Related U.S. Application Data

(60) Provisional application No. 62/204,230, filed on Aug. 12, 2015.

(51) Int. Cl.
*C07D 453/02* (2006.01)
*C07D 453/00* (2006.01)
*A61P 25/00* (2006.01)

(52) U.S. Cl.
CPC ......... *C07D 453/02* (2013.01); *C07D 453/00* (2013.01); *A61P 25/00* (2018.01)

(58) Field of Classification Search
CPC ...... C07D 453/02; C07D 453/00; A61P 25/00
USPC ....................... 514/275, 278, 379
See application file for complete search history.

(56) References Cited

U.S. PATENT DOCUMENTS

| | | | |
|---|---|---|---|
| 3,666,767 A | 5/1972 | Wittekind et al. |
| 3,835,142 A | 9/1974 | Wittekind et al. |
| 4,863,919 A | 9/1989 | Smith |
| 5,444,068 A | 8/1995 | Heitsch et al. |
| 5,635,525 A | 6/1997 | Heitsch et al. |
| 5,750,522 A | 5/1998 | Saab et al. |
| 5,889,002 A | 3/1999 | Nielsen et al. |
| 5,935,585 A | 8/1999 | Bernardon et al. |
| 6,171,603 B1 | 1/2001 | Bernardon et al. |
| 6,225,310 B1 | 5/2001 | Nielsen et al. |
| 6,462,036 B1 | 10/2002 | Doyle et al. |
| 6,624,173 B1 | 9/2003 | Crooks et al. |
| 6,727,070 B2 | 4/2004 | Thomas et al. |
| 6,869,958 B2 | 3/2005 | Li |
| 6,911,543 B2 | 6/2005 | Walker et al. |
| 7,019,011 B2 | 3/2006 | Lesuisse et al. |
| 7,071,216 B2 | 7/2006 | Renhowe et al. |
| 7,166,629 B2 | 1/2007 | Lesuisse et al. |
| 7,176,198 B2 | 2/2007 | Piotrowski et al. |
| 7,196,109 B2 | 3/2007 | Lesuisse et al. |
| 7,214,686 B2 | 5/2007 | Bencherif et al. |
| 7,241,773 B2 | 7/2007 | Ji et al. |
| 7,253,196 B2 | 8/2007 | Henriksson et al. |
| 7,371,862 B2 | 5/2008 | Vanotti et al. |
| 7,388,118 B2 | 6/2008 | Romero et al. |
| 7,407,981 B2 | 8/2008 | Lesuisse et al. |
| 7,423,150 B2 | 9/2008 | Costales et al. |
| 7,455,978 B2 | 11/2008 | Thomas et al. |
| 7,514,450 B2 | 4/2009 | Peters et al. |
| 7,582,669 B2 | 9/2009 | Lesuisse et al. |
| 7,629,374 B2 | 12/2009 | Lesuisse et al. |
| 7,652,010 B2 | 1/2010 | Peters et al. |
| 7,674,899 B2 | 3/2010 | Peters et al. |
| 7,683,084 B2 | 3/2010 | Faghih et al. |
| 7,687,515 B2 | 3/2010 | Cai et al. |
| 7,696,238 B2 | 4/2010 | Merla et al. |
| 7,728,010 B2 | 6/2010 | Amiri et al. |
| 7,741,364 B2 | 6/2010 | Faghih et al. |
| 7,750,022 B2 | 7/2010 | Peters et al. |
| 7,786,171 B2 | 8/2010 | Schrimpf et al. |
| 7,795,453 B2 | 9/2010 | Flebner et al. |

(Continued)

FOREIGN PATENT DOCUMENTS

| | | |
|---|---|---|
| EP | 0327335 | 10/1992 |
| JP | 3087763 | 9/2000 |

(Continued)

OTHER PUBLICATIONS

International Search Report and Written Opinion dated Oct. 27, 2016 for co-pending International Application No. PCT/US2016/046367.
International Search Report dated Feb. 19, 2016 for PCT/US2015/065497 (4 pages).
International Search Report dated Aug. 16, 2016 for PCT/US2016/036689 (3 pages).
International Search Report dated Oct. 27, 2016 for PCT/US2016/046367 (3 pages).
International Search Report dated Jan. 10, 2017 for PCT/US2016/056607 (3 pages).

(Continued)

*Primary Examiner* — Pancham Bakshi
(74) *Attorney, Agent, or Firm* — Jones Day

(57) ABSTRACT

The present invention relates to novel geminal substituted aminobenzisoxazole compounds, and pharmaceutical compositions of the same, that are suitable as agonists or partial agonists of α7-nAChR, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

13 Claims, 2 Drawing Sheets

(56) References Cited

U.S. PATENT DOCUMENTS

| | | |
|---|---|---|
| 7,807,700 B2 | 10/2010 | Henriksson et al. |
| 7,872,017 B2 | 1/2011 | Ji et al. |
| 7,897,766 B2 | 3/2011 | Schrimpf et al. |
| 7,902,217 B2 | 3/2011 | Xie et al. |
| 7,902,222 B2 | 3/2011 | Ji et al. |
| 7,994,223 B2 | 8/2011 | Schrimpf et al. |
| 8,076,350 B2 | 12/2011 | Ji et al. |
| 8,163,914 B2 | 4/2012 | Scanio et al. |
| 8,163,915 B2 | 4/2012 | Bunnelle |
| 8,163,916 B2 | 4/2012 | Schrimpf et al. |
| 8,168,791 B2 | 5/2012 | Shi et al. |
| 8,173,667 B2 | 5/2012 | Feuerback et al. |
| 8,273,891 B2 | 9/2012 | Schumacher et al. |
| 8,278,320 B2 | 10/2012 | McDonald et al. |
| 8,288,389 B2 | 10/2012 | Best et al. |
| 8,299,108 B2 | 10/2012 | Amiri et al. |
| 8,309,577 B2 | 11/2012 | Cook et al. |
| 8,314,119 B2 | 11/2012 | Schrimpf et al. |
| 8,383,657 B2 | 2/2013 | Faghih et al. |
| 8,415,382 B2 | 4/2013 | Costales et al. |
| 8,431,575 B2 | 4/2013 | Gohimukkula et al. |
| 8,445,690 B2 | 5/2013 | Bridgewater et al. |
| 8,470,813 B2 | 6/2013 | Faghih et al. |
| 8,481,555 B2 | 7/2013 | Lentz et al. |
| 8,507,516 B2 | 8/2013 | McDonald et al. |
| 8,536,221 B2 | 9/2013 | Mortell et al. |
| 8,541,592 B2 | 9/2013 | Henriksson et al. |
| 8,546,410 B2 | 10/2013 | Liu et al. |
| 8,586,746 B2 | 11/2013 | Schrimpf et al. |
| 8,609,713 B2 | 12/2013 | Faghih et al. |
| 8,614,330 B2 | 12/2013 | Amiri et al. |
| 8,648,085 B2 | 2/2014 | Mittelbiberach et al. |
| 8,686,011 B2 | 4/2014 | Henriksson et al. |
| 8,741,900 B2 | 6/2014 | Gohimukkula et al. |
| 8,778,939 B2 | 7/2014 | Nichols et al. |
| 8,841,289 B2 | 9/2014 | Ratcliffe et al. |
| 8,846,661 B2 | 9/2014 | Schrimpf et al. |
| 8,853,241 B2 | 10/2014 | Ji et al. |
| 8,946,432 B2 | 2/2015 | Sinha et al. |
| 8,980,888 B2 | 3/2015 | Okano et al. |
| 8,980,889 B2 | 3/2015 | Okano et al. |
| 8,987,453 B2 | 3/2015 | Schrimpf et al. |
| 9,012,447 B2 | 4/2015 | Hitchcock et al. |
| 9,045,461 B2 | 6/2015 | Gohimukkula et al. |
| 2002/0028808 A1 | 3/2002 | Hansen |
| 2002/0035106 A1 | 3/2002 | Hansen et al. |
| 2003/0109519 A1 | 3/2003 | Sturis |
| 2003/0125323 A1 | 7/2003 | Sturis |
| 2003/0235583 A1 | 12/2003 | Sturis et al. |
| 2004/0019053 A1 | 1/2004 | Roark |
| 2004/0043983 A1 | 3/2004 | Li |
| 2004/0147522 A1 | 7/2004 | Wong et al. |
| 2004/0192594 A1 | 9/2004 | Reid et al. |
| 2005/0186591 A1 | 8/2005 | Bumcrot et al. |
| 2005/0239853 A1 | 10/2005 | Bart et al. |
| 2005/0245567 A1 | 11/2005 | Peters et al. |
| 2006/0116395 A1 | 6/2006 | Piotrowski et al. |
| 2007/0082350 A1 | 4/2007 | Landfield et al. |
| 2007/0185086 A1 | 8/2007 | Bencherif et al. |
| 2007/0281938 A1 | 12/2007 | Henriksson et al. |
| 2008/0268044 A1 | 10/2008 | Appleby et al. |
| 2009/0005390 A1 | 1/2009 | Peters et al. |
| 2009/0099099 A1 | 4/2009 | Wang et al. |
| 2009/0170869 A1 | 7/2009 | Best et al. |
| 2009/0197860 A1 | 8/2009 | Ji et al. |
| 2009/0312356 A1 | 12/2009 | De Micheli et al. |
| 2010/0298289 A1 | 11/2010 | Raphy et al. |
| 2010/0305089 A1 | 12/2010 | Ji et al. |
| 2011/0014283 A1 | 1/2011 | Clarke et al. |
| 2011/0020447 A1 | 1/2011 | Clarke et al. |
| 2011/0082107 A1 | 4/2011 | Henriksson et al. |
| 2011/0189280 A1 | 8/2011 | Clarke et al. |
| 2011/0262407 A1 | 10/2011 | Bencherif et al. |
| 2012/0035178 A1 | 2/2012 | Cook et al. |
| 2012/0035189 A1 | 2/2012 | Cook et al. |
| 2012/0065219 A1 | 3/2012 | Ji et al. |
| 2012/0190704 A1 | 7/2012 | Schrimpf et al. |
| 2012/0190706 A1 | 7/2012 | Scanio et al. |
| 2012/0196890 A1 | 8/2012 | Bunnelle |
| 2012/0202804 A1 | 8/2012 | Hatfield et al. |
| 2012/0202828 A1 | 8/2012 | Hatfield et al. |
| 2012/0245195 A1 | 9/2012 | Chen et al. |
| 2012/0288501 A1 | 11/2012 | Amiri et al. |
| 2013/0123278 A1 | 5/2013 | Edwards et al. |
| 2013/0131064 A1 | 5/2013 | Cook et al. |
| 2013/0217683 A1 | 8/2013 | Xie et al. |
| 2013/0224195 A1 | 8/2013 | Costales et al. |
| 2013/0225584 A1 | 8/2013 | Andreotti et al. |
| 2013/0231365 A1 | 9/2013 | Koenig |
| 2013/0252901 A1 | 9/2013 | Mediannikov et al. |
| 2013/0310419 A1 | 11/2013 | Sinha et al. |
| 2013/0331387 A1 | 12/2013 | Sinha et al. |
| 2014/0018327 A1 | 1/2014 | Sinha et al. |
| 2014/0024644 A1 | 1/2014 | Hitchcock et al. |
| 2014/0221377 A1 | 8/2014 | Cook et al. |
| 2014/0234270 A1 | 8/2014 | Bencherif et al. |
| 2015/0094309 A1 | 4/2015 | Cook et al. |
| 2015/0132327 A1 | 5/2015 | Okano et al. |
| 2015/0133448 A1 | 5/2015 | Okano et al. |
| 2015/0158867 A1 | 6/2015 | Schrimpf et al. |
| 2015/0166536 A1 | 6/2015 | Okano et al. |
| 2015/0275303 A1 | 10/2015 | Feuerbach et al. |

FOREIGN PATENT DOCUMENTS

| | | | |
|---|---|---|---|
| JP | 2003-267977 | 9/2003 | |
| WO | WO 1993/009116 | 5/1993 | |
| WO | WO 2001/066546 | 9/2001 | |
| WO | WO 02/100858 A2 * | 12/2002 | ........... C07D 453/02 |
| WO | WO 2002/100858 | 12/2002 | |
| WO | WO 2004/022544 | 3/2004 | |
| WO | WO 2004/039366 | 5/2004 | |
| WO | WO 2004/039815 | 5/2004 | |
| WO | WO 2004/062662 | 7/2004 | |
| WO | WO 2005/066166 | 7/2005 | |
| WO | WO 2005/066167 | 7/2005 | |
| WO | WO 2006/065233 | 6/2006 | |
| WO | WO 2006/069097 | 6/2006 | |
| WO | WO 2006/122799 | 11/2006 | |
| WO | WO 2007/018738 | 2/2007 | |
| WO | WO 2007/038367 | 4/2007 | |
| WO | WO 2007/045478 | 4/2007 | |
| WO | WO 2007/080191 | 7/2007 | |
| WO | WO 2008/000469 | 1/2008 | |
| WO | WO 2009/017454 | 2/2009 | |
| WO | WO 2009/050227 | 4/2009 | |
| WO | WO 2009/083526 | 7/2009 | |
| WO | WO 2011/036167 | 3/2011 | |
| WO | WO 2012/108490 | 8/2012 | |
| WO | WO 2013/132380 | 9/2013 | |
| WO | WO 2013/174947 | 11/2013 | |
| WO | WO 2013/177024 | 11/2013 | |
| WO | WO 2014/072957 | 5/2014 | |
| WO | WO 2014/083003 | 6/2014 | |
| WO | WO 2014/091388 | 6/2014 | |
| WO | WO 2014/111839 | 7/2014 | |
| WO | WO 2014/141091 | 9/2014 | |
| WO | WO 2014/195848 | 12/2014 | |
| WO | WO 2014/203150 | 12/2014 | |
| WO | WO 2015/066371 | 5/2015 | |
| WO | WO 2016/100184 | 6/2016 | |

OTHER PUBLICATIONS

European Search Report dated Apr. 26, 2018 for EP 15870786.9 (7 pages).

Compound Summary for CID 160186, *PubChem Open Chemistry Database*, NIH U.S. National Library of Medicine, National Center for Biotechnology Information, Entry Creation Date: Jul. 11, 2005.

Marrero, Mario B. et al. "An α7 Nicotinic Acetylcholine Receptor-Selective Agonist Reduces Weight Gain and Metabolic Changes in a Mouse Model of Diabetes," *The Journal of Pharmacology and Experimental Therapeutics*, 332:1 (Jan. 1, 2010) 173-180.

(56) References Cited

OTHER PUBLICATIONS

Mazurov, Anatoly et al. "2-(Arylmethyl)-3-substituted Quinuclidines as Selective α7 Nicotinic Receptor Ligands," *Bioorganic & Medicinal Chemistry Letters*, 15:8 (Apr. 15, 2005) 2073-2077.

European Search Report dated Jan. 9, 2019 for EP 16835845.5 (8 pages).

European Search Report dated Jan. 23, 2019 for EP 16808279.0 (5 pages).

Albuquerque, E. X. et al. "Modulation of Nicotinic Receptor Activity in the Central Nervous System: A Novel Approach to the Treatment of Alzheimer Disease," *Alzheimer Disease and Associated Disorders*, 15:1 (2001) S19-S25.

D'Andrea, Michael R. et al. "Targeting the Alpha 7 Nicotinic Acetylcholine Receptor to Reduce Amyloid accumulation in Alzheimer's Disease Pyramidal Neurons," *Current Pharmaceutical Design*, 12 (2006) 677-684.

Deutsch, Stephen I. et al. "Progressive Worsening of Adaptive Functions in Down Syndrome May be Mediated by the Complexing of Soluble Aβ Peptides with the Alpha7 Nicotinic Acetylcholine Receptor: Therapeutic Implications," *Clinical Neuropharmacology*, 26:5 (2003) 277-283.

Gundisch, Daniela et al., "Nicotinic Acetylcholine Receptor Ligands, a Patent Review (2006-2011)," *Expert Opinion on Therapeutic Patents*, 21:12 (Nov. 20, 2011) 1867-1896.

Haydar, Simon N. et al. "SAR and Biological Evaluation of SEN12333/WAY-317538: Novel Alpha7 Nicotinic Acetylcholine Receptor Agonist," *Bioorganic & Medicinal Chemistry*, 17 (2009) 5247-5258.

Jenkins, Jeremy L. et al. "A 3D Similarity Method for Scaffold Hopping from Known Drugs or Natural Ligands to New Chemotypes," *J. Med. Chem.*, 47 (2004) 6144-6159.

Jeyarasasingam, G. et al. "Stimulation of Non-Alpha7 Nicotinic Receptors Partially Protects Dopaminergic Neurons from 1-Methyl-4-Phenylpyridinium-Induced Toxicity in Culture," *Neuroscience*, 109:2 (2002) 275-285.

Nagele, R. G. et al. "Intracellular Accumulation of β-Amyloids$_{1-42}$ in Neurons is Facilitated by the Alpha7 Nicotinic Acetylcholine Receptor in Alzheimer's Disease," *Neuroscience*, 11:2 (2002) 199-211.

Nordberg, Agneta "Neuroprotection in Alzheimer's Disease—New Strategies for Treatment," *Neurotoxicity Research*, 2 (2000) 157-165.

Wang, Hoau-Yan et al. "Dissociating β-Amyloid from Alpha7 Nicotinic Acetylcholine Receptor by a Novel Therapeutic Agent, S24795, Normalizes Alpha7 Nicotinic Acetylcholine and NMDA Receptor Function in Alzheimer's Disease Brain," *The Journal of Neuroscience*, 29:35 (Sep. 2, 2009) 10961-10973.

* cited by examiner

GEMINAL SUBSTITUTED AMINOBENZISOXAZOLE COMPOUNDS AS AGONISTS OF α7-NICOTINIC ACETYLCHOLINE RECEPTORS

CROSS REFERENCE TO RELATED APPLICATION

This application claims the benefit of priority from U.S. Provisional Application No. 62/204,230, filed Aug. 12, 2015. The foregoing related application, in its entirety, is incorporated herein by reference.

FIELD OF THE INVENTION

The present invention relates to novel geminal substituted aminobenzisoxazole compounds, and pharmaceutical compositions of the same, that are suitable as agonists or partial agonists of the α7-nicotinic acetylcholine receptor, and methods of preparing these compounds and compositions, and the use of these compounds and compositions in methods of maintaining, treating and/or improving cognitive function. In particular, methods of administering the compound or composition to a patient in need thereof, for example a patient with a cognitive deficiency and/or a desire to enhance cognitive function, that may derive a benefit therefrom.

BACKGROUND OF THE INVENTION

Many forms of cognitive disease represent a steadily growing medical and social problem of our aging societies around the world. The prevalence of cognitive disease, for example dementia in North America, is approximately 6 to 10% of the population, with Alzheimer's disease accounting for a substantial portion of these cases. It is also recognized that many other neurological and psychiatric disorders may display symptoms of cognitive impairment. Some believe the main pathological features of Alzheimer's disease may relate to intraneuronal neurofibrillary tangles, formation of amyloid beta plaques and/or neurodegeneration of mainly cholinergic and, in later stages, also serotonergic, noradrenergic, and other neurons, resulting in deficiencies of acetylcholine and other neurotransmitters. Some theories suggest that the gradual development of an acetylcholine signaling deficiency may be responsible for the early clinical manifestations of cognitive disease. Consequently, some believe that compounds that improve cholinergic functioning, such as acetylcholine esterase inhibitors may ameliorate the cognitive deficits in patients with cognitive disease. The most widely used acetylcholine esterase inhibitor is donepezil hydrochloride (Aricept®). In addition to Alzheimer's disease, cholinergic deficits (reductions in neurotransmitter and/or receptor levels) are observed in other disorders where there are cognitive deficits, such as schizophrenia, major depressive disorder, and Parkinson's disease.

Nicotinic acetylcholine receptors (nAChR) form a large family of ion channels which are activated by the neurotransmitter acetylcholine which is produced in the body (Galzi and Changeux, Neuropharmacol. 1995, 34, 563-582). A functional nAChR consists of five subunits which may be different (certain combinations of α1-9 and (β1-4,γ,δ,ε subunits) or identical (α7-9). This leads to the formation of a diversity of subtypes which differ in the distribution in the muscles, the nervous system and other organs (McGehee and Role, Annu. Rev. Physiol. 1995, 57, 521-546). Activation of nAChR leads to influx of cations into the cell and to stimulation of nerve cells or muscle cells. Selective activation of individual nAChR subtypes restricts this stimulation to the cell types which have a corresponding nAChR subtype and is thus able to avoid unwanted side effects such as, for example, stimulation of nAChRs in the muscles. Clinical experiments with nicotine and experiments in various animal models indicate that central nicotinic acetylcholine receptors are involved in learning and memory processes (e.g. Rezvani and Levin, Biol. Psychiatry 2001, 49, 258-267). Nicotinic acetylcholine receptors of the alpha7 subtype (α7 nAChR) have a particularly high concentration in regions of the brain which are important for learning and memory, such as the hippocampus and the cerebral cortex (Seguela et al., J. Neurosci. 1993, 13, 596-604). The α7 nAChR has a particularly high permeability for calcium ions, modulates neurotransmission, influences the growth of axons and, in this way, modulates neuronal plasticity (Broide and Leslie, Mol. Neurobiol. 1999, 20, 1-16).

WO 2003/055878 describes a variety of agonists of the α7 nAChR said to be useful for improving cognition. WO 2003/055878 suggests that certain agonists of the α7 nAChR are useful for improving perception, concentration, learning or memory, especially after cognitive impairments like those occurring for example in situations/diseases/syndromes such as mild cognitive impairment, age-associated learning and memory impairments, age-associated memory loss, Alzheimer's disease, schizophrenia and certain other cognitive disorders.

BRIEF SUMMARY OF THE INVENTION

An aspect of the invention provides a geminal substituted aminobenzisoxazole compound represented by Formula (Ia) or Formula (Ib):

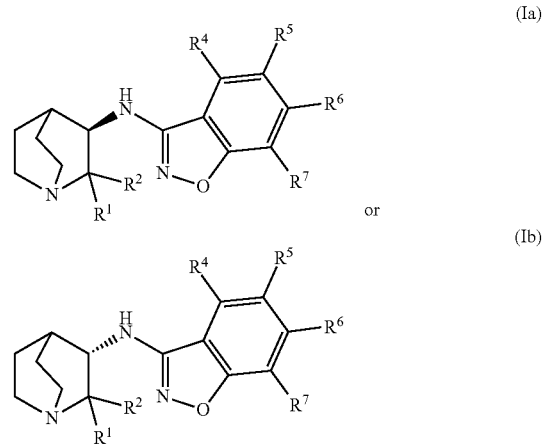

wherein:
R$^1$ and R$^2$ independently represent an unbranched C$_1$-C$_4$-alkyl radical or a branched C$_3$-C$_4$-alkyl radical; or the C(R$^1$)(R$^2$) moiety forms a (3-4 membered)-carbocycle, wherein R$^1$ and R$^2$ taken together represent a C$_2$-C$_3$-alkyl di-radical; wherein the unbranched C$_1$-C$_4$-alkyl radical, the branched C$_3$-C$_4$-alkyl radical, and the C$_2$-C$_3$-alkyl di-radical may be independently substituted with up to 4 radical substituents comprising: -D, —F, —CN, —CH$_3$, —CH$_2$CH$_3$, =O, or —OR$^3$;
R$^3$ independently represents —H; an unbranched C$_1$-C$_4$-alkyl radical; a branched C$_3$-C$_4$-alkyl radical; or a $C_3$-$C_4$-cycloalkyl radical; wherein the unbranched $C_1$-$C_4$-alkyl radical, the branched $C_3$-$C_4$-alkyl radical, and the $C_3$-$C_4$-cycloalkyl radical may be independently substituted with up to 4 radical substituents comprising: -D, —F, —CN, =O, —OH, —$OC_1$-$C_4$-alkyl, or —$OCF_3$; and $R^4$, $R^5$, $R^6$, and $R^7$ independently represent —H, -D, halogen radical, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^8)(R^9)$, —$(CO)N(R^8)(R^9)$, —$NR^8(CO)(R^9)$, —$SO_2C_1$-$C_4$-alkyl, —$SO_2N(R^8)(R^9)$, —$(CH_2)_mSO_2C_1$-$C_4$-alkyl, —$(CH_2)_mSO_2N(R^8)(R^9)$, —$N(R^8)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^8)SO_2C_1$-$C_4$-alkyl, may be independently substituted with up to 5 radical substituents comprising: -D, halogen radical, =O, —$OR^8$, —$(CH_2)_mOR^8$, —$N(R^8)(R^9)$, —$NR^8(CO)(R^9)$, —$(CH_2)_mN(R^8)(R^9)$, —$SO_2C_1$-$C_4$-alkyl, —$SO_2N(R^8)(R^9)$, —$(CH_2)_mSO_2C_1$-$C_4$-alkyl, —$(CH_2)_m SO_2N(R^8)(R^9)$, —$N(R^8)SO_2C_1$-$C_4$-alkyl, —$(CO)(CH_2)_mR^8$, —$(CO)N(R^8)(R^9)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents comprising: -D, halogen radical, —CN, —$OR^8$, —$(CH_2)_mOR^8$, —$N(R^8)(R^9)$, —$NR^8(CO)(R^9)$, —$(CH_2)_mN(R^8)(R^9)$, —$SO_2N(R^8)(R^9)$, —$(CH_2)_mSO_2C_1$-$C_4$-alkyl, —$(CH_2)_mSO_2N(R^8)(R^9)$, —$N(R^8)SO_2C_1$-$C_4$-alkyl, —$(CO)(CH_2)_mR^8$, —$(CO)N(R^8)(R^9)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical;

$R^8$ and $R^9$ independently represent —H; an unbranched $C_1$-$C_6$-alkyl radical, a branched $C_3$-$C_6$-alkyl radical; a $C_3$-$C_6$-cycloalkyl radical; or the $N(R^8)(R^9)$ moiety forms a cycle, wherein $R^8$ and $R^9$ taken together represent a $C_2$-$C_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —($SO_2$)-unbranched $C_1$-$C_4$-alkyl, or —($SO_2$)-branched $C_3$-$C_4$-alkyl, and with the further proviso that when the at least one ring atom is sulfur, the sulfur may be independently substituted with 0 to 2 =O; wherein the $C_2$-$C_6$-alkyl di-radical or the alky portion of said (3-6 membered)-heteroalkyl di-radical may be independently substituted with up to 5 radical substituents comprising: D, halogen radical, =O, an unbranched $C_1$-$C_6$-alkyl radical, or a branched $C_3$-$C_6$-alkyl radical; and m independently represents an integer from 1 to 6; or a pharmaceutically acceptable salt thereof.

An aspect of the invention relates to the geminal substituted aminobenzisoxazole compound represented by Formula (Ia):

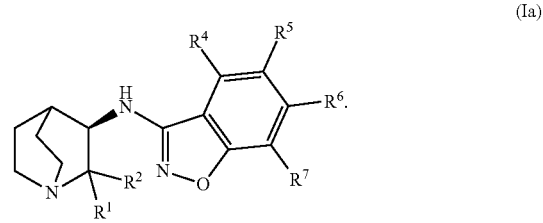

(Ia)

An aspect of the invention relates to the geminal substituted aminobenzisoxazole compound represented by Formula (Ia), wherein $R^1$ and $R^2$ independently represent an unbranched $C_1$-alkyl radical and said compound is represented by Formula (IIa):

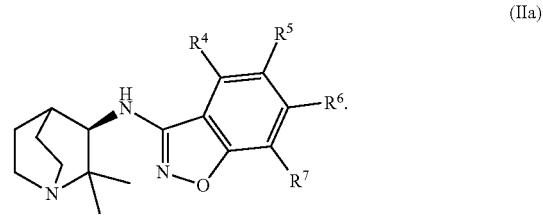

(IIa)

An aspect of the invention relates to the geminal substituted aminobenzisoxazole compound represented by Formula (Ia), wherein $R^1$ and $R^2$ taken together represent a $C_2$-alkyl di-radical and said compound is represented by Formula (IIIa):

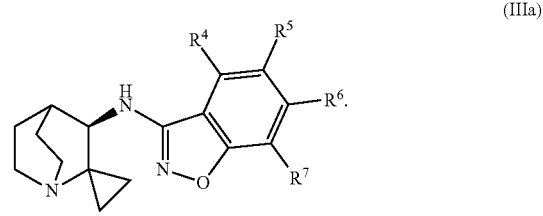

(IIIa)

An aspect of the invention relates to the geminal substituted aminobenzisoxazole compound represented by Formula (Ib):

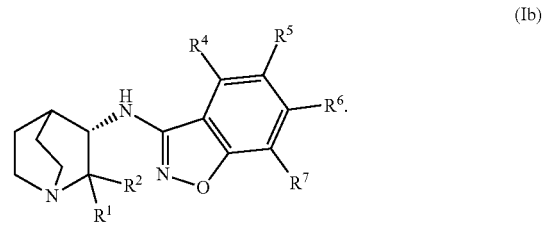

(Ib)

An aspect of the invention relates to the geminal substituted aminobenzisoxazole compound represented by Formula (Ib), wherein $R^1$ and $R^2$ independently represent an unbranched $C_1$-alkyl radical and said compound is represented by Formula (IIb):

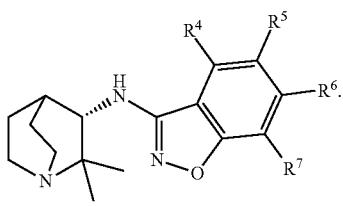

(IIb)

An aspect of the invention relates to the geminal substituted aminobenzisoxazole compound represented by Formula (Ib), wherein $R^1$ and $R^2$ taken together represent a $C_2$-alkyl di-radical and said compound is represented by Formula (IIIb):

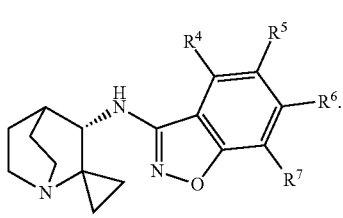

(IIIb)

An aspect of the invention relates to a single stereoisomer of the geminal substituted aminobenzisoxazole compound represented by Formula (Ia) or (Ib), Formula (IIa) or (IIb), or Formula (IIIa) or (IIIb), or a pharmaceutically acceptable salt thereof.

An aspect of the invention relates to a single enantiomer or a single diastereomer of the geminal substituted aminobenzisoxazole compound represented by Formula (Ia) or (Ib), Formula (IIa) or (IIb), or Formula (IIIa) or (IIIb), or a pharmaceutically acceptable salt thereof.

An aspect of the invention relates to a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof; and at least one pharmaceutically acceptable carrier, excipient or diluent.

An aspect of the invention relates to a method comprising administering to a patient in need thereof an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating a patient in need thereof, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of maintaining, treating, curing and/or improving at least one cognitive function in a patient in need thereof, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating a patient diagnosed as having a cognitive impairment, comprising: administering to the an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating a patient in need thereof, comprising: administering to the patient, for example, a patient diagnosed with having a cognitive impairment, Limited Cognitive Impairment, Mild Cognitive Impairment, Alzheimer's disease, and/or schizophrenia, a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; such that the patient may derive a benefit therefrom.

Another aspect of the invention provides a method of treating one or more symptoms associated with a cognitive impairment, comprising administering to a patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein the patient suffers from, or has been diagnosed as having, a cognitive impairment.

Another aspect of the invention provides a method of improving cognition of a patient in need thereof, comprising: administering to the patient a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of improving cognition in a patient suffering from a cognitive impairment, such as a cognitive impairment associated with either schizophrenia or Alzheimer's disease, for example mild Alzheimer's disease, moderate Alzheimer's disease, severe Alzheimer's disease, or mild-to-moderate Alzheimer's disease, comprising administering an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating a patient suffering from, diagnosed with having, or suffers from one or more symptoms associated with, a cognitive impairment, for example, Alzheimer's disease, dementia of an Alzheimer's type, MCI, LCI, or schizophrenia, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent. For example, the method of treating a patient suffering from, diagnosed with having, or suffers from one or more symptoms associated with, a cognitive impairment, may provide said patient at least one of the following: (i) treats, minimizes progression of, prevents the deterioration of, or reduces the rate of deterioration of, one or more symptoms associated with the cognitive impairment; (ii) treats the cognitive impairment; (iii) improves cognition in said cognitively impaired patient; (iv) improves one or more behavioral symptoms associated with the cognitive impairment; (v) provides a pro-cognitive effect; (vi) provides a pro-cognitive effect in at least one of the following: visual motor, learning, delayed memory, or executive function, or (vii) provides a positive effect on clinical function in said cognitively impaired patient.

Another aspect of the invention provides a method of treating a patient previously treated, or currently being treated, with an AChEI, that is suffering from, or has been diagnosed with having, a cognitive impairment, for example, Alzheimer's disease, dementia of an Alzheimer's type, MCI, LCI, or schizophrenia, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluents; wherein the method improves one or more symptoms associated with the cognitive impairment in the previously, or currently, AChEI treated patient.

Another aspect of the invention provides a method of treating a patient suffering from, or diagnosed with having a cognitive impairment, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein the method provides a positive effect on cognition or a positive effect on clinical function in said cognitively impaired patient, and wherein said patient has been previously treated or is currently being treated with an AChEI.

Another aspect of the invention provides a method of improving cognition in a patient diagnosed as having a probable cognitive disease, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of improving or substantially improving one or more symptoms in a cognitive disease patient, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of slowing the rate of deterioration of at least one symptom in a cognitive disease patient, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient the pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating one or more symptoms associated with a cognitive disease in a patient suffering therefrom, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent Another aspect provides a method of minimizing or substantially halting the rate of progression of one or more cognitive diseases in a patient suffering from a cognitive disease, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of substantially stopping or reversing progression of one or more cognitive diseases, in a patient suffering therefrom, comprising: administering to the patient an effective dose of a geminal substituted aminobenzisoxazole compound represented by Formula (Ia) or (Ib), Formula (IIa) or (IIb), Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating dementia, comprising: administering to a patient in need thereof an effective amount of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the effective amount of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein said effective amount is administered in an effective dose.

Another aspect of the invention provides a method of treating dementia, comprising: administering to a patient in need thereof an effective amount of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

Another aspect of the invention provides a method of treating dementia, comprising: administering to a patient in need thereof an effective amount of a geminal substituted aminobenzisoxazole compound represented by Formula (Ia) or (Ib), Formula (IIa) or (IIb), or Formula (IIIa) or (IIIb), or a pharmaceutically acceptable salt thereof, wherein the geminal substituted aminobenzisoxazole compound represented by Formula (Ia) or (Ib), Formula (IIa) or (IIb), or Formula (IIIa) or (IIIb), or a pharmaceutically acceptable salt thereof, is administered in the form of a pharmaceutical composition comprising at least one pharmaceutically acceptable carrier, excipient or diluent.

Another aspect of the invention provides a method of treating dementia, comprising: administering to a patient in need thereof an effective amount of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein the pharmaceutical composition is in the form of a tablet.

Another aspect of the invention provides a method of treating a patient having a cognitive disease and being administered an acetylcholine esterase inhibitor, comprising: administering to a patient in need thereof an effective amount of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient an effective dose of a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein the treatment comprises halting the administration of the acetylcholine esterase inhibitor prior to treating with the geminal substituted aminobenzisoxazole compound represented by Formula (Ia) or (Ib), Formula (IIa) or (IIb), or Formula (IIIa) or (IIIb), or a pharmaceutically acceptable salt thereof.

DETAILED DESCRIPTION OF THE INVENTION

Figure 1:
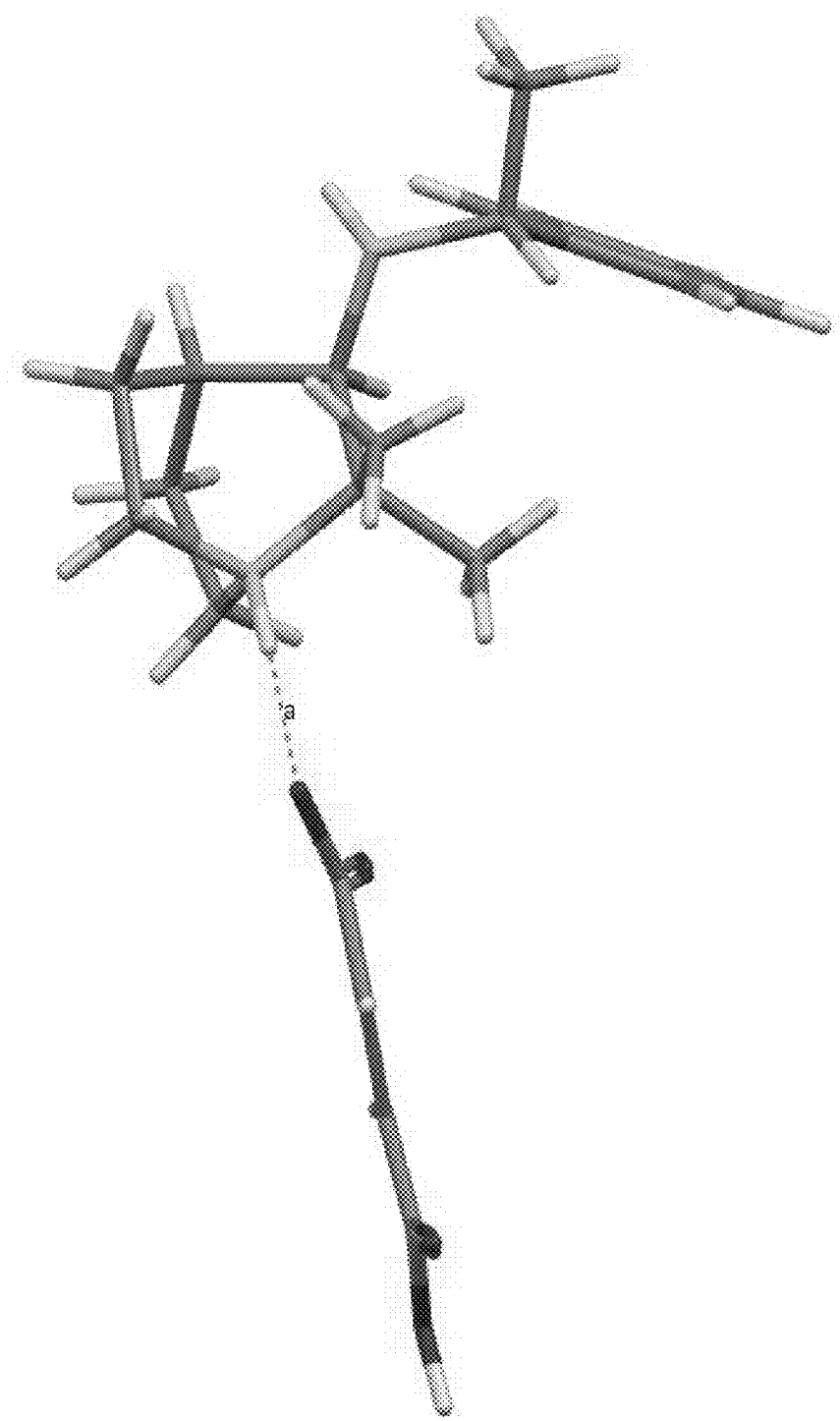
FIG. 1: Illustrates a 3-D representation of the formed crystal of (R)-2,2-dimethyl-N—((R)-1-phenylethyl)quinuclidin-3-amine fumarate.

An embodiment of the present invention provides a geminal substituted aminobenzisoxazole compound represented by Formula (Ia) or Formula (Ib):

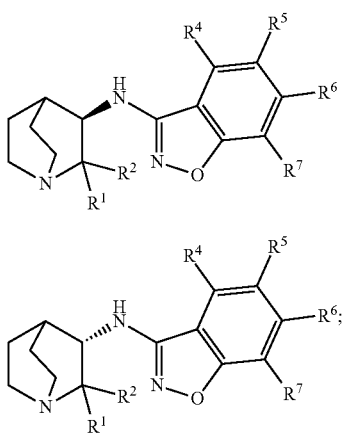

wherein:
R¹ and R² independently represent an unbranched $C_1$-$C_4$-alkyl radical or a branched $C_3$-$C_4$-alkyl radical; or the $C(R^1)(R^2)$ moiety forms a (3-4 membered)-carbocycle, wherein R¹ and R² taken together represent a $C_2$-$C_3$-alkyl di-radical; wherein the unbranched $C_1$-$C_4$-alkyl radical, the branched $C_3$-$C_4$-alkyl radical, and the $C_2$-$C_3$-alkyl di-radical may be independently substituted with up to 4 radical substituents comprising: -D, —F, —CN, —$CH_3$, —$CH_2CH_3$, =O, or —$OR^3$;

R³ independently represents —H; an unbranched $C_1$-$C_4$-alkyl radical; a branched $C_3$-$C_4$-alkyl radical; or a $C_3$-$C_4$-cycloalkyl radical; wherein the unbranched $C_1$-$C_4$-alkyl radical, the branched $C_3$-$C_4$-alkyl radical, and the $C_3$-$C_4$-cycloalkyl radical may be independently substituted with up to 4 radical substituents comprising: -D, —F, —CN, =O, —OH, —$OC_1$-$C_4$-alkyl, or —$OCF_3$; and R⁴, R⁵, R⁶, and R⁷ independently represent —H, -D, halogen radical, —CN, an unbranched $C_1$-$C_4$-alkyl radical, a branched $C_3$-$C_4$-alkyl radical, a $C_3$-$C_6$-cycloalkyl radical, an unbranched —$OC_1$-$C_4$-alkyl, a branched or cyclic —$OC_3$-$C_4$-alkyl, —$N(R^8)(R^9)$, —$CO)N(R^8)(R^9)$, —$NR^8(CO)(R^9)$, —$SO_2N(R^8)(R^9)$, —$SO_2N(R^8)(R^9)$, —$(CH_2)_mSO_2C_1$-$C_4$-alkyl, —$(CH_2)_m$ $SO_2N(R^8)(R^9)$, —$N(R^8)SO_2C_1$-$C_4$-alkyl, an aryl radical, or a heteroaryl radical; wherein the alkyl portion of the unbranched $C_1$-$C_4$-alkyl radical, the branched $C_3$-$C_4$-alkyl radical, the $C_3$-$C_6$-cycloalkyl radical, the unbranched —$OC_1$-$C_4$-alkyl, the branched or cyclic —$OC_3$-$C_4$-alkyl, the —$SO_2C_1$-$C_4$-alkyl, the —$(CH_2)_mSO_2C_1$-$C_4$-alkyl, or the —$N(R^8)SO_2C_1$-$C_4$-alkyl, may be independently substituted with up to 5 radical substituents comprising: -D, halogen radical, =O, —$OR^8$, —$(CH_2)_mOR^8$, —$N(R^8)(R^9)$, —$NR^8(CO)(R^9)$, —$(CH_2)_mN(R^8)(R^9)$, —$SO_2C_1$-$C_4$-alkyl, —$SO_2N(R^8)(R^9)$, —$(CH_2)_mSO_2C_1$-$C_4$-alkyl, —$(CH_2)_m$ $SO_2N(R^8)(R^9)$, —$N(R^8)SO_2C_1$-$C_4$-alkyl, —$(CO)(CH_2)_mR^8$, —$(CO)N(R^8)(R^9)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical; and wherein the aryl radical or the heteroaryl radical may be independently substituted with up to 5 radical substituents comprising: -D, halogen radical, —CN, —$OR^8$, —$(CH_2)_mOR^8$, —$N(R^8)(R^9)$, —$NR^8(CO)(R^9)$, —$(CH_2)_mN(R^8)(R^9)$, —$SO_2C_1$-$C_4$-alkyl, —$SO_2N(R^8)(R^9)$, —$(CH_2)_mSO_2C_1$-$C_4$-alkyl, —$(CH_2)_m$ $SO_2N(R^8)(R^9)$, —$N(R^8)SO_2C_1$-$C_4$-alkyl, —$(CO)(CH_2)_mR^8$, —$(CO)N(R^8)(R^9)$, an unbranched $C_1$-$C_6$-alkyl radical, a branched $C_3$-$C_6$-alkyl radical, a $C_3$-$C_6$-cycloalkyl radical, a $C_1$-$C_6$-hydroxyalkyl radical, a $C_1$-$C_2$-haloalkyl radical, or —$OC_1$-$C_2$-haloalkyl radical;

R⁸ and R⁹ independently represent H; an unbranched $C_1$-$C_6$-alkyl radical, a branched $C_3$-$C_6$-alkyl radical; a $C_3$-$C_6$-cycloalkyl radical; or the $N(R^8)(R^9)$ moiety forms a cycle, wherein R⁸ and R⁹ taken together represent a $C_2$-$C_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —($SO_2$)-unbranched $C_1$-$C_4$-alkyl, or —($SO_2$)-branched $C_3$-$C_4$-alkyl, and with the further proviso that when the at least one ring atom is sulfur, the sulfur may be independently substituted with 0 to 2 =O; wherein the $C_2$-$C_6$-alkyl di-radical or the alky portion of said (3-6 membered)-heteroalkyl di-radical may be independently substituted with up to 5 radical substituents comprising: D, halogen radical, =O, an unbranched $C_1$-$C_6$-alkyl radical, or a branched $C_3$-$C_6$-alkyl radical; and m independently represents an integer from 1 to 6;

or a pharmaceutically acceptable salt thereof.

In certain embodiments, the geminal substituted aminobenzisoxazole compound represented by Formula (Ia) may comprise the R¹ and R² independently representing an unbranched $C_1$-$C_3$-alkyl radical, such as an unbranched $C_1$-$C_2$-alkyl radical; or the $C(R^1)(R^2)$ moiety forms a (3-4 membered)-carbocycle, wherein R¹ and R² taken together represent a $C_2$-$C_3$-alkyl di-radical; wherein the unbranched $C_1$-$C_3$-alkyl radical, such as the unbranched $C_1$-$C_2$-alkyl radical; and the $C_2$-$C_3$-alkyl di-radical may be independently substituted with up to 4 radical substituents, such as up to 3 radical substituents, comprising: -D, —F, —Cl, —CN, —$CH_3$, —$CH_2CH_3$, =O, or —$OR^3$, such as —$OCF_3$. For example, in certain embodiments, the geminal substituted aminobenzisoxazole compound represented by Formula (Ia) may comprise the R¹ and R² independently representing an unbranched $C_1$-$C_2$-alkyl radical; or the $C(R^1)(R^2)$ moiety forms a (3-4 membered)-carbocycle, wherein R¹ and R² taken together represent a $C_2$-$C_3$-alkyl di-radical; wherein the unbranched $C_1$-$C_3$-alkyl radical, such as the unbranched $C_1$-$C_2$-alkyl radical; and the $C_2$-$C_3$-alkyl di-radical may be independently substituted with up to 4 radical substituents, such as up to 3 radical substituents, comprising: -D, —F, —Cl, —CN, =O, or —$OR^3$, such as —$OCF_3$.

In certain embodiments, the geminal substituted aminobenzisoxazole compound represented by Formula (Ia) may comprise the R³ independently representing —H; an unbranched $C_1$-$C_4$-alkyl radical, such as an unbranched $C_1$-$C_3$-alkyl radical or $C_1$-$C_2$-alkyl radical; a branched $C_3$-$C_4$-alkyl radical, such as a branched $C_3$-alkyl radical; or a $C_3$-$C_4$-cycloalkyl radical, such as a $C_3$-cycloalkyl radical; wherein the unbranched $C_1$-$C_4$-alkyl radical, such as the unbranched $C_1$-$C_3$-alkyl radical or $C_1$-$C_2$-alkyl radical; the branched $C_3$-$C_4$-alkyl radical, such as the branched $C_3$-alkyl radical; or the $C_3$-$C_4$-cycloalkyl radical, such as the $C_3$-cycloalkyl radical, may be independently substituted with up to 4 radical substituents, such as up to 3 radical substituents, comprising: -D, —F, —Cl, —CN, =O, —OH, —OC$_1$-C$_4$-alkyl, or —OCF$_3$.

In certain embodiments, the geminal substituted aminobenzisoxazole compound represented by Formula (Ia) may comprise the R$^1$ and R$^2$ independently representing an unbranched C$_1$-alkyl radical, wherein said compound is represented by Formula (IIa):

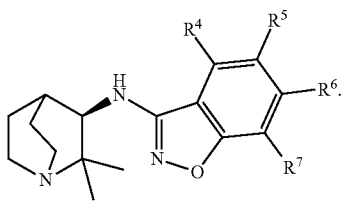

(IIa)

In certain embodiments, the geminal substituted aminobenzisoxazole compound represented by Formula (Ia) may comprise the R$^1$ and R$^2$ taken together represent a C$_2$-alkyl di-radical, wherein said compound is represented by Formula (IIIa):

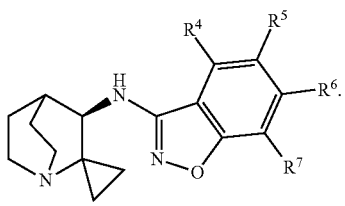

(IIIa)

In certain embodiments, the geminal substituted aminobenzisoxazole compound represented by Formula (Ib) may comprise the R$^1$ and R$^2$ independently representing an unbranched C$_1$-alkyl radical, wherein said compound is represented by Formula (IIb):

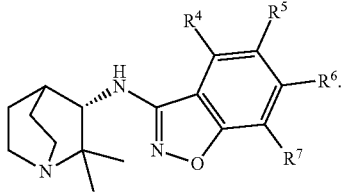

(IIb)

In certain embodiments, the geminal substituted aminobenzisoxazole compound represented by Formula (Ib) may comprise the R$^1$ and R$^2$ taken together represent a C$_2$-alkyl di-radical, wherein said compound is represented by Formula (IIIb):

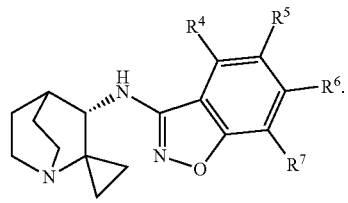

(IIIb)

In certain embodiments, the geminal substituted aminobenzisoxazole compound represented by Formula (Ia) or (Ib), Formula (IIa) or (IIb), or Formula (IIIa) or (IIIb), may comprise R$^4$, R$^5$, R$^6$, and R$^7$ independently representing —H, -D, halogen radical, —CN, an unbranched C$_1$-C$_3$-alkyl radical, a branched C$_3$-C$_4$-alkyl radical, a C$_3$-C$_5$-cycloalkyl radical, an unbranched —OC$_1$-C$_4$-alkyl, a branched or cyclic —OC$_3$-C$_4$-alkyl, —N(R$^8$)(R$^9$), —(CO)N(R$^8$)(R$^9$), —NR$^8$(CO)(R$^9$), —SO$_2$C$_1$-C$_2$-alkyl, —SO$_2$N(R$^8$)(R$^9$), —(CH$_2$)$_m$SO$_2$C$_1$-C$_2$-alkyl, —(CH$_2$)$_m$SO$_2$N(R$^8$)(R$^9$), —N(R$^8$)SO$_2$C$_1$-C$_2$-alkyl, an aryl radical, or a heteroaryl radical; wherein the alkyl portion of the unbranched C$_1$-C$_3$-alkyl radical, the branched C$_3$-C$_4$-alkyl radical, the C$_3$-C$_5$-cycloalkyl radical, the unbranched —OC$_1$-C$_4$-alkyl, the branched or cyclic —OC$_3$-C$_4$-alkyl, the —SO$_2$C$_1$-C$_2$-alkyl, the —(CH$_2$)$_m$SO$_2$C$_1$-C$_2$-alkyl, or the —N(R$^8$)SO$_2$C$_1$-C$_2$-alkyl, may be independently substituted with up to 5 radical substituents, for example, up to 4 radical substituents or up to 3 radical substituents, comprising: -D, halogen radical, =O, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_2$-alkyl, —SO$_2$N(R$^8$)(R$^9$), —(CH$_2$)$_m$SO$_2$C$_1$-C$_2$-alkyl, —(CH$_2$)$_m$SO$_2$N(R$^8$)(R$^9$), —N(R$^8$)SO$_2$C$_1$-C$_2$-alkyl, —(CO)(CH$_2$)$_m$R$^8$, —(CO)N(R$^8$)(R$^9$), an unbranched C$_1$-C$_4$-alkyl radical, a branched C$_3$-C$_4$-alkyl radical, a C$_3$-C$_5$-cycloalkyl radical, a C$_1$-C$_4$-hydroxyalkyl radical, a C$_1$-C$_2$-haloalkyl radical, or —OC$_1$-C$_2$-haloalkyl radical; and wherein the aryl radical or the heteroaryl radical may be independently substituted with up to 5 radical substituents, for example, up to 4 radical substituents or up to 3 radical substituents, comprising: -D, halogen radical, —CN, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_2$-alkyl, —SO$_2$N(R$^8$)(R$^9$), —(CH$_2$)$_m$SO$_2$C$_1$-C$_2$-alkyl, —(CH$_2$)$_m$SO$_2$N(R$^8$)(R$^9$), —N(R$^8$)SO$_2$C$_1$-C$_2$-alkyl, —(CO)(CH$_2$)$_m$R$^8$, —(CO)N(R$^8$)(R$^9$), an unbranched C$_1$-C$_4$-alkyl radical, a branched C$_3$-C$_4$-alkyl radical, a C$_3$-C$_5$-cycloalkyl radical, a C$_1$-C$_4$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise R$^4$ and R$^5$ independently representing —H, -D, —F, —Cl, —Br, —CN, an unbranched C$_1$-C$_3$-alkyl radical, a branched C$_3$-C$_4$-alkyl radical, a C$_3$-C$_4$-cycloalkyl radical, —CHF$_2$, —CH$_2$F, —CF$_3$, an unbranched —OC$_1$-C$_3$-alkyl, a branched or cyclic —OC$_3$-alkyl, —OCF$_3$, —SO$_2$CH$_3$, —SO$_2$N(CH$_3$)$_2$, or —N(R$^8$)SO$_2$CH$_3$; wherein the alkyl portion of the unbranched C$_1$-C$_3$-alkyl radical, the branched C$_3$-C$_4$-alkyl radical, the C$_3$-C$_4$-cycloalkyl radical, the unbranched —OC$_1$-C$_3$-alkyl, or the branched or cyclic —OC$_3$-alkyl, may be independently substituted with up to 5 radical substituents, for example, up to 4 radical substituents or up to 3 radical substituents, comprising: -D, —F, —Cl, —OR$^8$, =O, —CH$_3$, —CHF$_2$, —CH$_2$F, —CF$_3$, cyclopropyl radical, cyclobutyl radical, or —OCF$_3$; and wherein R$^8$ may independently represent —H, —CH$_3$, or —CH$_2$CH$_3$.

In certain embodiments, the geminal substituted aminobenzisoxazole compound represented by Formula (Ia) or (Ib), Formula (IIa) or (IIb), or Formula (IIIa) or (IIIb), may comprise R$^4$ and R$^5$ independently representing —H, -D, —F, —Cl, —CH$_3$, —CH$_2$CH$_3$, a cyclopropyl radical, —CHF$_2$, —CH$_2$F, —CF$_3$, —OCH$_3$, —OCH$_2$CH$_3$, —OCH(CH$_3$)$_2$, —OCF$_3$, —SO$_2$CH$_3$, —SO$_2$N(CH$_3$)$_2$, or —N(H)SO$_2$CH$_3$.

In certain embodiments, the geminal substituted aminobenzisoxazole compound represented by Formula (Ia) or (Ib), Formula (IIa) or (IIb), or Formula (IIIa) or (IIIb), may comprise R$^4$ and R$^5$ independently representing —H, -D, or halogen radical, for example, —F, —Cl, or —Br. For example, in certain embodiments, R$^4$ and R$^5$ may independently represent —H, -D, —F, or —Cl, such as —H, -D, or —F. In certain embodiments, R$^4$ and R$^5$ may independently represent —H or -D. In certain embodiments, R$^4$ may independently represent —H or -D, and R$^5$ may independently represent —F or —Cl, such as —F. In certain embodiments, R$^4$ may independently represent —F or —Cl, such as —F, and R$^5$ may independently represent —H or -D.

In certain embodiments, the geminal substituted aminobenzisoxazole compound represented by Formula (Ia) or (Ib), Formula (IIa) or (IIb), or Formula (IIIa) or (IIIb), may comprise R$^6$ independently representing —F, —Cl, —Br, —CN, an unbranched C$_1$-C$_4$-alkyl radical, a branched C$_3$-C$_4$-alkyl radical, a C$_3$-C$_6$-cycloalkyl radical, an unbranched —OC$_1$-C$_4$-alkyl, a branched or cyclic —OC$_3$-C$_4$-alkyl, —N(R$^8$)(R$^9$), —(CO)N(R$^8$)(R$^9$), —NR$^8$(CO)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, an aryl radical, or a heteroaryl radical; wherein the alkyl portion of the unbranched C$_1$-C$_4$-alkyl radical, the branched C$_3$-C$_4$-alkyl radical, the C$_3$-C$_6$-cycloalkyl radical, the unbranched —OC$_1$-C$_4$-alkyl, the branched or cyclic —OC$_3$-C$_4$-alkyl, the —SO$_2$C$_1$-C$_4$-alkyl, the —(CH$_2$)$_m$SO$_2$C$_1$-C$_4$-alkyl, or the —N(R$^8$)SO$_2$C$_1$-C$_4$-alkyl, may be independently substituted with up to 5 radical substituents, for example, up to 4 radical substituents or up to 3 radical substituents, comprising: -D, —F, —Cl, —Br, =O, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein the aryl radical or the heteroaryl radical may be independently substituted with up to 5 radical substituents, for example, up to 4 radical substituents or up to 3 radical substituents, comprising: -D, —F, —Cl, —Br, —CN, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise R$^6$ independently representing —F, —Cl, —Br, —CN, an unbranched C$_1$-C$_4$-alkyl radical, a branched C$_3$-C$_4$-alkyl radical, a C$_3$-C$_4$-cycloalkyl radical, an unbranched —OC$_1$-C$_4$-alkyl, a branched or cyclic —OC$_3$-C$_4$-alkyl, —OCHF$_2$, —OCH$_2$F, —OCF$_3$, —OCH$_2$CF$_3$, —N(R$^8$)(R$^9$), —(CO)N(R$^8$)(R$^9$), —NR$^8$(CO)(R$^9$), —SO$_2$CH$_3$, —SO$_2$N(R$^8$)(R$^9$), —CH$_2$CH$_2$SO$_2$C$_1$-C$_4$-alkyl, or —N(R$^8$)SO$_2$CH$_3$, an aryl radical, or a heteroaryl radical; wherein the alkyl portion of the unbranched C$_1$-C$_4$-alkyl radical, the branched C$_3$-C$_4$-alkyl radical, the C$_3$-C$_4$-cycloalkyl radical, the unbranched —OC$_1$-C$_4$-alkyl, the branched or cyclic —OC$_3$-C$_4$-alkyl, or the —CH$_2$CH$_2$SO$_2$C$_1$-C$_4$-alkyl, may be independently substituted with up to 5 radical substituents, for example, up to 4 radical substituents or up to 3 radical substituents, comprising: -D, —F, —Cl, —Br, =O, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein the aryl radical or the heteroaryl radical may be independently substituted with up to 5 radical substituents, for example, up to 4 radical substituents or up to 3 radical substituents, comprising: -D, —F, —Cl, —Br, —CN, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise R$^6$ independently representing —F, —Cl, —Br, —CN, —CH$_3$, —CH$_2$CH$_3$, cyclopropyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, —OCHF$_2$, —OCH$_2$F, —OCF$_3$, —OCH$_2$CF$_3$, —SO$_2$CH$_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the phenyl radical or the heteroaryl radical, such as the N-pyrazole radical, the furan radical, the thiophene radical, the imidazole radical, the oxazole radical, the thiazole radical, the pyridyl radical, the pyrazine radical, the pyrimidine radical, or the oxadiazole radical, may be independently substituted with up to 5 radical substituents, for example, up to 4 radical substituents or up to 3 radical substituents, comprising: -D, —F, —Cl, —Br, —CN, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —(CO)(CH$_2$)$_m$R$^8$, —(CO)N(R$^8$)(R$^9$), an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise R$^6$ independently representing —F, —Cl, —Br, —CN, —CH$_3$, —CH$_2$CH$_3$, cyclopropyl radical, —CHF$_2$, —CH$_2$F, —CH$_2$CF$_3$, —CF$_3$, —CH$_2$CF$_3$, —OCH$_3$, —OCH$_2$CH$_3$, —OCH(CH$_3$)$_2$, —O-cyclopropyl, —OCF$_3$, —SO$_2$CH$_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the phenyl radical or the heteroaryl radical, such as the N-pyrazole radical, the furan radical, the thiophene radical, the imidazole radical, the oxazole radical, the thiazole radical, the pyridyl radical, the pyrazine radical, the pyrimidine radical, or the oxadiazole radical, may be independently substituted with up to 5 radical substituents, for example, up to 4 radical substituents or up to 3 radical substituents, comprising: -D, —F, —Cl, —Br, —CN, —OR$^8$, —CH$_3$, cyclopropyl radical, —CHF$_2$, —CH$_2$F, —CF$_3$, —CH$_2$CF$_3$, —OCF$_3$, or —OCH$_2$CF$_3$. For example, in certain embodiments, R$^6$ may independently represent —F, —Cl, —Br, —CN, —CH$_3$, —CH$_2$CH$_3$, cyclopropyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$. In certain embodiments, R$^6$ may independently represent —F, —Cl, —Br, —CH$_3$, or —OCH$_3$, such as R$^6$ may independently represent —F, —Cl, —CH$_3$, or —OCH$_3$.

In certain embodiments, the geminal substituted aminobenzisoxazole compound represented by Formula (Ia) or (Ib), Formula (IIa) or (IIb), or Formula (IIIa) or (IIIb), may comprise R$^7$ independently representing —H, -D, —F, —Cl, —Br, —CN, an unbranched C$_1$-C$_4$-alkyl radical, a branched C$_3$-C$_4$-alkyl radical, a C$_3$-C$_6$-cycloalkyl radical, an unbranched —OC$_1$-C$_4$-alkyl, a branched or cyclic —OC$_3$-C$_4$-alkyl, —N(R$^8$)(R$^9$), —(CO)N(R$^8$)(R$^9$), —NR$^8$(CO)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, an aryl radical, or a heteroaryl radical; wherein the alkyl portion of the unbranched C$_1$-C$_4$-alkyl radical, the branched C$_3$-C$_4$-alkyl radical, the C$_3$-C$_6$-cycloalkyl radical, the unbranched —OC$_1$-C$_4$-alkyl, the branched or cyclic —OC$_3$-C$_4$-alkyl, the —SO$_2$C$_1$-C$_4$-alkyl, the —(CH$_2$)$_m$SO$_2$C$_1$-C$_4$-alkyl, or the —N(R$^8$)SO$_2$C$_1$-C$_4$-alkyl, may be independently substituted with up to 5 radical substituents, for example, up to 4 radical substituents or up to 3 radical substituents, comprising: -D, —F, —Cl, —Br, =O, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), —OCF$_3$ an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein aryl radical or the heteroaryl radical may be independently substituted with up to 5 radical substituents, for example, up to 4 radical substituents or up to 3 radical substituents, comprising: -D, —F, —Cl, —Br, —CN, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —SO$_2$C$_1$-C$_4$-alkyl, —SO$_2$N(R$^8$)(R$^9$), —(CH$_2$)$_m$SO$_2$C$_1$-C$_4$-alkyl, —(CH$_2$)$_m$SO$_2$N(R$^8$)(R$^9$), —N(R$^8$)SO$_2$C$_1$-C$_4$-alkyl, —(CO)(CH$_2$)$_m$R$^8$, —(CO)N(R$^8$)(R$^9$), —OCF$_3$, an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise R$^7$ independently representing —H, -D, —F, —Cl, —CN, an unbranched C$_1$-C$_3$-alkyl radical, a branched C$_3$-C$_4$-alkyl radical, a C$_3$-C$_4$-cycloalkyl radical, unbranched —OC$_1$-C$_3$-alkyl, a branched or cyclic —OC$_3$-C$_4$-alkyl, —OCHF$_2$, —OCH$_2$F, —OCF$_3$, —OCH$_2$CF$_3$; wherein the alkyl portion of the unbranched C$_1$-C$_3$-alkyl radical, the branched C$_3$-C$_4$-alkyl radical, the C$_3$-C$_4$-cycloalkyl radical, the unbranched —OC$_1$-C$_3$-alkyl, or the branched or cyclic —OC$_3$-C$_4$-alkyl, may be independently substituted with up to 5 radical substituents, for example, up to 4 radical substituents or up to 3 radical substituents, comprising: -D, —F, —Cl, —Br, =O, —OR$^8$, —(CH$_2$)$_m$OR$^8$, —N(R$^8$)(R$^9$), —NR$^8$(CO)(R$^9$), —(CH$_2$)$_m$N(R$^8$)(R$^9$), —(CO)(CH$_2$)$_m$R$^8$, —(CO)N(R$^8$)(R$^9$), —OCF$_3$, an unbranched C$_1$-C$_6$-alkyl radical, a branched C$_3$-C$_6$-alkyl radical, a C$_3$-C$_6$-cycloalkyl radical, a C$_1$-C$_6$-hydroxyalkyl radical, a C$_1$-C$_2$-haloalkyl radical, or —OC$_1$-C$_2$-haloalkyl radical; and wherein R$^8$ and R$^9$ may independently represent —H, an unbranched C$_1$-C$_6$-alkyl radical, such as —CH$_3$ or —CH$_2$CH$_3$, a branched C$_3$-C$_6$-alkyl radical, such as —CH(CH$_3$)$_2$, or a C$_3$-C$_6$-cycloalkyl radical, such as a cyclopropyl radical, or the N(R$^8$)(R$^9$) moiety forms a cycle, wherein R$^8$ and R$^9$ taken together represent a C$_2$-C$_6$-alkyl di-radical, such as a C$_2$-C$_5$-alkyl di-radical, or a (3-6 membered)-heteroalkyl di-radical, such as a (3-5 membered)-heteroalkyl di-radical; and wherein m may independently represents an integer from 1 to 6, for example, an integer from 1 to 4, such as 1 to 2, 2 to 3, or 3 to 4.

In certain embodiments, the geminal substituted aminobenzisoxazole compound represented by Formula (Ia) or (Ib), Formula (IIa) or (IIb), or Formula (IIIa) or (IIIb), may comprise $R^7$ independently representing —H, -D, —F, —Cl, —CN, —CH$_3$, —CH(CH$_3$)$_2$, cyclopropyl radical, cyclobutyl radical, —CH$_2$F, —CHF$_2$, —CF$_3$, —CH$_2$CF$_3$, —OCH$_3$, —OCH$_2$CH$_3$, —OCH(CH$_3$)$_2$, —O-cyclopropyl, —OCHF$_2$, —OCH$_2$F, —OCF$_3$, or —OCH$_2$CF$_3$. For example, in certain embodiments, $R^7$ may independently represent —H, -D, —F, —Cl, —CN, —CH$_3$, cyclopropyl radical, cyclobutyl radical, —CH$_2$F, —CHF$_2$, —CF$_3$, —OCH$_3$, —OCH$_2$CH$_3$, —OCH(CH$_3$)$_2$, —O-cyclopropyl, or —OCF$_3$, such as $R^7$ may independently represent —H, -D, —F, —Cl, —CH$_3$, —OCH$_3$, —OCH$_2$CH$_3$, or —CF$_3$, for example, $R^7$ may independently represent —H, -D, —F, —Cl, —CH$_3$, or —OCH$_3$.

In certain embodiments, the geminal substituted aminobenzisoxazole compound represented by Formula (Ia) or (Ib), Formula (IIa) or (IIb), or Formula (IIIa) or (IIIb), may comprise: $R^4$ and $R^5$ independently representing —H or -D, $R^5$ and $R^7$ independently representing —H or -D, $R^4$ and $R^7$ independently representing —H or -D, or $R^4$, $R^5$, and $R^7$ independently representing —H or -D; and $R^6$ independently representing —H, -D, —F, —Cl, —Br, —CN, an unbranched C$_1$-C$_3$-alkyl radical, for example, —CH$_3$ or —CH$_2$CH$_3$, a branched C$_3$-C$_4$-alkyl radical, a cyclopropyl radical, a cyclobutyl radical, —CHF$_2$, —CH$_2$F, —CF$_3$, —CH$_2$CF$_3$, an unbranched —OC$_1$-C$_3$-alkyl, such as —OCH$_3$ or —OCH$_2$CH$_3$, a branched or cyclic —OC$_3$-C$_4$-alkyl, such as —OCH(CH$_3$)$_2$ or —O-cyclopropyl, —OCHF$_2$, —OCH$_2$F, —OCF$_3$, —OCH$_2$CF$_3$, —SO$_2$CH$_3$, a phenyl radical or a heteroaryl radical, such as an N-pyrazole radical, a furan radical, a thiophene radical, an imidazole radical, an oxazole radical, a thiazole radical, a pyridyl radical, a pyrazine radical, a pyrimidine radical, or an oxadiazole radical; wherein the alkyl portion of the unbranched C$_1$-C$_3$-alkyl radical, branched C$_3$-C$_4$-alkyl radical, unbranched —OC$_1$-C$_3$-alkyl, or the branched or cyclic —OC$_3$-C$_4$-alkyl, may be independently substituted with up to 5 radical substituents, for example, up to 4 radical substituents or up to 3 radical substituents, comprising: -D, —F, —Cl, =O, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —CH$_2$CF$_3$, —OCF$_3$, or —OCH$_2$CF$_3$; and wherein the phenyl radical or the heteroaryl radical may be independently substituted with up to 5 radical substituents, for example, up to 4 radical substituents or up to 3 radical substituents, comprising: -D, —F, —Cl, —Br, —CN, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —CH$_2$CF$_3$, —OCF$_3$, or —OCH$_2$CF$_3$.

In certain embodiments, the geminal substituted aminobenzisoxazole compound represented by Formula (Ia) or (Ib), Formula (IIa) or (IIb), or Formula (IIIa) or (IIIb), may comprise $R^4$ independently representing —H, -D, or a halogen radical, for example —H, -D, —F, or —Cl, such as —H, -D, or —F; $R^5$ independently representing —H, -D, or a halogen radical, for example —H, -D, —F, or —Cl, such as —H, -D, or —F; $R^6$ independently representing —H, -D, —F, —Cl, —Br, —CN, an unbranched C$_1$-C$_3$-alkyl radical, for example, —CH$_3$ or —CH$_2$CH$_3$, —CH(CH$_3$)$_2$, a cyclopropyl radical, a cyclobutyl radical, —CHF$_2$, —CH$_2$F, —CF$_3$, —CH$_2$CF$_3$, an unbranched —OC$_1$-C$_3$-alkyl, such as —OCH$_3$ or —OCH$_2$CH$_3$, —OCH(CH$_3$)$_2$, —O-cyclopropyl, —OCHF$_2$, —OCH$_2$F, —OCF$_3$, —OCH$_2$CF$_3$, —SO$_2$CH$_3$, a phenyl radical or a heteroaryl radical, such as an N-pyrazole radical or an oxadiazole radical; and $R^7$ independently representing —H, -D, —F, —Cl, —CN, an unbranched C$_1$-C$_3$-alkyl radical, for example, —CH$_3$ or —CH$_2$CH$_3$, —CH(CH$_3$)$_2$, a cyclopropyl radical, a cyclobutyl radical, —CHF$_2$, —CH$_2$F, —CF$_3$, —CH$_2$CF$_3$, an unbranched —OC$_1$-C$_3$-alkyl, such as —OCH$_3$ or —OCH$_2$CH$_3$, —OCH (CH$_3$)$_2$, —O-cyclopropyl, —OCHF$_2$, —OCH$_2$F, —OCF$_3$, —OCH$_2$CF$_3$; wherein the alkyl portion of the unbranched C$_1$-C$_3$-alkyl radical, —CH(CH$_3$)$_2$, unbranched —OC$_1$-C$_3$-alkyl, —OCH(CH$_3$)$_2$, or —O-cyclopropyl, may be independently substituted with up to 5 radical substituents, for example, up to 4 radical substituents or up to 3 radical substituents, comprising: -D, —F, —Cl, =O, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$; and wherein the phenyl radical or the heteroaryl radical may be independently substituted with up to 5 radical substituents, for example, up to 4 radical substituents or up to 3 radical substituents, comprising: -D, —F, —Cl, —Br, —CN, —OCH$_3$, —OCH$_2$CH$_3$, —OCH(CH$_3$)$_2$, —CH$_3$, —CH$_2$CH$_3$, cyclopropyl radical, —CHF$_2$, —CH$_2$F, —CF$_3$, —OCF$_3$, or —OCH$_2$CF$_3$.

In certain embodiments, the geminal substituted aminobenzisoxazole compound represented by Formula (Ia) or (Ib), Formula (IIa) or (IIb), or Formula (IIIa) or (IIIb), may comprise $R^4$ independently representing —H, -D, or a halogen radical, for example —H, -D, —F, or —Cl, such as —H, -D, or —F; $R^5$ independently representing —H, -D, or a halogen radical, for example —H, -D, —F, or —Cl, such as —H, -D, or —F; $R^6$ independently representing —H, -D, —F, —Cl, —Br, —CN, —CH$_3$, —CH$_2$CH$_3$, —CH(CH$_3$)$_2$, a cyclopropyl radical, a cyclobutyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$; and $R^7$ independently representing —H, -D, —F, —Cl, —CN, —CH$_3$, —CH$_2$CH$_3$, —CH(CH$_3$)$_2$, a cyclopropyl radical, a cyclobutyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$.

For example, in certain embodiments, R$^4$ may independently represent —H, -D, —F, or —Cl, such as —H, -D, or —F; R$^5$ may independently represent —H, -D, —F, or —Cl, such as —H, -D, or —F; R$^6$ may independently represent —F, —Cl, —Br, —CN, —CH$_3$, —CH$_2$CH$_3$, a cyclopropyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$, such as —F, —Cl, —Br, —CH$_3$, or —OCH$_3$, or such as —F, —Cl, —CH$_3$, or —OCH$_3$; and R$^7$ may independently represent —H, -D, —F, —Cl, —CN, —CH$_3$, —CH$_2$CH$_3$, —CH(CH$_3$)$_2$, a cyclopropyl radical, a cyclobutyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$, such as —H, -D, —F, —Cl, —CH$_3$, —OCH$_3$, —OCH$_2$CH$_3$, or —CF$_3$, for example, R$^7$ may independently represent —H, -D, —F, —Cl, —CH$_3$, or —OCH$_3$.

In certain embodiments, the geminal substituted aminobenzisoxazole compound represented by Formula (Ia) or (Ib), Formula (IIa) or (IIb), or Formula (IIIa) or (IIIb), at least one of R$^4$, R$^5$, R$^6$, and R$^7$ does not independently represent —H. For example, in certain embodiments, R$^4$ independently represents —H, and at least one of R$^5$, R$^6$, and R$^7$ does not independently represent —H; R$^5$ independently represents —H, and at least one of R$^4$, R$^6$, and R$^7$ does not independently represent —H; R$^6$ independently represents —H, and at least one of R$^4$, R$^5$, and R$^7$ does not independently represent —H; or R$^7$ independently represents —H, and at least one of R$^4$, R$^5$, and R$^6$ does not independently represent —H.

In certain embodiments, the geminal substituted aminobenzisoxazole compound represented by Formula (Ia) or (Ib), Formula (IIa) or (IIb), or Formula (IIIa) or (IIIb), may comprise R$^8$, R$^9$, or both R$^8$ and R$^9$, independently representing —H; an unbranched C$_1$-C$_6$-alkyl radical, such as —CH$_3$ or —CH$_2$CH$_3$, a branched C$_3$-C$_6$-alkyl radical, such as —CH(CH$_3$)$_2$; or a C$_3$-C$_6$-cycloalkyl radical, such as a cyclopropyl radical or a cyclobutyl radical. For example, R$^8$ and R$^9$ may independently represent —H, —CH$_3$, —CH$_2$CH$_3$, —CH(CH$_3$)$_2$, a cyclopropyl radical, or a cyclobutyl radical, such as independently represent —H, —CH$_3$, or —CH$_2$CH$_3$.

In certain embodiments, the geminal substituted aminobenzisoxazole compound represented by Formula (Ia) or (Ib), Formula (IIa) or (IIb), or Formula (IIIa) or (IIIb), may comprise an N(R$^8$)(R$^9$) moiety, wherein the N(R$^8$)(R$^9$) moiety forms a cycle, wherein R$^8$ and R$^9$ taken together represent a C$_2$-C$_6$-alkyl di-radical or a (3-6 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H, an unbranched C$_1$-C$_4$-alkyl radical, a branched C$_3$-C$_4$-alkyl radical, a C$_3$-C$_4$-cycloalkyl radical, —(CO)-unbranched C$_1$-C$_4$-alkyl, —(CO)-branched C$_3$-C$_4$-alkyl, —(SO$_2$)-unbranched C$_1$-C$_4$-alkyl, or —(SO$_2$)-branched C$_3$-C$_4$-alkyl, and with the further proviso that when the at least one ring atom is sulfur, the sulfur may be independently substituted with 0 to 2 =O; wherein the C$_2$-C$_6$-alkyl di-radical or the alky portion of said (3-6 membered)-heteroalkyl di-radical may be independently substituted with up to 5 radical substituents, for example, up to 4 radical substituents or up to 3 radical substituents, comprising: -D, halogen radical, =O, an unbranched C$_1$-C$_6$-alkyl radical, or a branched C$_3$-C$_6$-alkyl radical.

In certain embodiments, the N(R$^8$)(R$^9$) moiety may form a cycle, wherein R$^8$ and R$^9$ taken together represent a C$_2$-C$_6$-alkyl di-radical, such as a C$_2$-C$_5$-alkyl di-radical or C$_3$-C$_4$-alkyl di-radical; wherein the C$_2$-C$_6$-alkyl di-radical, such as a C$_2$-C$_5$-alkyl di-radical or C$_3$-C$_4$-alkyl di-radical, may be independently substituted with up to 5 radical substituents, for example, up to 4 radical substituents or up to 3 radical substituents, comprising: -D, halogen radical, =O, an unbranched C$_1$-C$_6$-alkyl radical, or a branched C$_3$-C$_6$-alkyl radical. For example, the N(R$^8$)(R$^9$) moiety may form a cycle, wherein R$^8$ and R$^9$ taken together represent a C$_2$-alkyl di-radical, a C$_3$-alkyl di-radical, C$_4$-alkyl di-radical, or C$_5$-alkyl di-radical, such as a C$_2$-alkyl di-radical.

In certain embodiments, the N(R$^8$)(R$^9$) moiety may, for example, form a cycle wherein the R$^8$ and R$^9$ taken together represent a (3-6 membered)-heteroalkyl di-radical, such as (4-5 membered)-heteroalkyl di-radical; wherein the (3-6 membered)-heteroalkyl di-radical comprises at least one ring atom selected from the group consisting of oxygen, nitrogen, and sulfur, with the proviso that when the at least one ring atom is nitrogen, the nitrogen is independently substituted with —H; an unbranched C$_1$-C$_4$-alkyl radical, such as —CH$_3$, —CH$_2$CH$_3$, or —CH$_2$CH$_2$CH$_3$, a branched C$_3$-C$_4$-alkyl radical, such as —CH(CH$_3$)$_2$; a C$_3$-C$_4$-cycloalkyl radical; —(CO)-unbranched C$_1$-C$_4$-alkyl; —(CO)-branched C$_3$-C$_4$-alkyl; —(SO$_2$)-unbranched C$_1$-C$_4$-alkyl; or —(SO$_2$)-branched C$_3$-C$_4$-alkyl; and with the further proviso that when the at least one ring atom is sulfur, the sulfur may be independently substituted with 0 to 2 =O; wherein the alky portion of said (3-6 membered)-heteroalkyl di-radical may be independently substituted with up to 5 radical substituents, for example, up to 4 radical substituents or up to 3 radical substituents, comprising: -D, halogen radical, =O, an unbranched C$_1$-C$_6$-alkyl radical, or a branched C$_3$-C$_6$-alkyl radical. For example, the N(R$^8$)(R$^9$) moiety may form a cycle, wherein R$^8$ and R$^9$ taken together represent a (4-5 membered)-heteroalkyl di-radical, wherein the (4-5 membered)-heteroalkyl di-radical comprises at least one ring atom selected from the group consisting of oxygen or nitrogen, with the proviso that when the at least one ring atom is nitrogen, the nitrogen is independently substituted with —H; —CH$_3$, —CH$_2$CH$_3$, —CH(CH$_3$)$_2$, a cyclopropyl radical. —(CO)CH$_3$, —(CO)CH$_2$CH$_3$, —(SO$_2$)CH$_3$, or —(SO$_2$)CH$_2$CH$_3$.

In certain embodiments, the geminal substituted aminobenzisoxazole compound represented by Formula (Ia) or (Ib), Formula (IIa) or (IIb), or Formula (IIIa) or (IIIb), may comprise racemic mixture of enantiomers, a mixture of diastereomers, a single enantiomer, or a single diastereomer, of the compound, or a pharmaceutically acceptable salt thereof. In certain embodiments, the geminal substituted aminobenzisoxazole compound represented by Formula (Ia) or (Ib), Formula (IIa) or (IIb), or Formula (IIIa) or (IIIb), may comprise a mixture of tautomers, substantially a single tautomer form, or a single tautomer form, such as a tautomer contained within the geminal substituted aminobenzisoxazole ring system or a tautomer resulting from one or more substitutents substituted on the geminal substituted aminobenzisoxazole ring system, for example, a tautomer may be contained within the geminal substituted aminobenzisoxazole ring system or one or more substituents substituted on the geminal substituted aminobenzisoxazole ring system containing a heteroaryl ring nitrogen adjacent to a heteroaryl ring carbon substituted with a hydroxyl group.

The chemical names and structure diagrams used herein to describe the compounds of the present invention, suprand infra, were created with the use of ChemBioDraw Ultra® Version 12.0 (available from CambridgeSoft Corp., Cambridge, Mass.).

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the compounds listed below, and single enantiomers and pharmaceutically acceptable salts thereof:

6-chloro-N-(2,2-dimethylquinuclidin-3-yl)benzo[d]isoxazol-3-amine;
6-chloro-N-(2,2-dimethylquinuclidin-3-yl)-7-fluorobenzo[d]isoxazol-3-amine;
N-(2,2-dimethylquinuclidin-3-yl)-6-methoxybenzo[d]isoxazol-3-amine;
6,7-dichloro-N-(2,2-dimethylquinuclidin-3-yl)benzo[d]isoxazol-3-amine;
6-chloro-N-(2,2-dimethylquinuclidin-3-yl)-7-methoxybenzo[d]isoxazol-3-amine;
N-(2,2-dimethylquinuclidin-3-yl)-6-methylbenzo[d]isoxazol-3-amine;
N-(2,2-dimethylquinuclidin-3-yl)-7-fluoro-6-methylbenzo[d]isoxazol-3-amine;
7-chloro-N-(2,2-dimethylquinuclidin-3-yl)-6-fluorobenzo[d]isoxazol-3-amine;
N-(2,2-dimethylquinuclidin-3-yl)-5-fluoro-6-methylbenzo[d]isoxazol-3-amine;
6-chloro-N-(2,2-dimethylquinuclidin-3-yl)-7-methylbenzo[d]isoxazol-3-amine;
6-chloro-N-(2,2-dimethylquinuclidin-3-yl)-5-fluorobenzo[d]isoxazol-3-amine;
6-chloro-N-(2,2-dimethylquinuclidin-3-yl)-7-ethoxybenzo[d]isoxazol-3-amine;
7-chloro-N-(2,2-dimethylquinuclidin-3-yl)-6-methylbenzo[d]isoxazol-3-amine;
6-chloro-N-(2,2-dimethylquinuclidin-3-yl)-7-(trifluoromethyl)benzo[d]isoxazol-3-amine;
6-chloro-N-(2,2-dimethylquinuclidin-3-yl)-7-isopropoxybenzo[d]isoxazol-3-amine;
6-chloro-N-(1'-azaspiro[cyclopropane-1,2'-bicyclo[2.2.2]octan]-3'-yl)benzo[d]isoxazol-3-amine;
6-chloro-7-fluoro-N-(1'-azaspiro[cyclopropane-1,2'-bicyclo[2.2.2]octan]-3'-yl)benzo[d]isoxazol-3-amine;
6-methoxy-N-(1'-azaspiro[cyclopropane-1,2'-bicyclo[2.2.2]octan]-3'-yl)benzo[d]isoxazol-3-amine;
6,7-dichloro-N-(1'-azaspiro[cyclopropane-1,2'-bicyclo[2.2.2]octan]-3'-yl)benzo[d]isoxazol-3-amine;
6-chloro-7-methoxy-N-(1'-azaspiro[cyclopropane-1,2'-bicyclo[2.2.2]octan]-3'-yl)benzo[d]isoxazol-3-amine;
6-methyl-N-(1'-azaspiro[cyclopropane-1,2'-bicyclo[2.2.2]octan]-3'-yl)benzo[d]isoxazol-3-amine;
7-fluoro-6-methyl-N-(1'-azaspiro[cyclopropane-1,2'-bicyclo[2.2.2]octan]-3'-yl)benzo[d]isoxazol-3-amine;
7-chloro-6-fluoro-N-(1'-azaspiro[cyclopropane-1,2'-bicyclo[2.2.2]octan]-3'-yl)benzo[d]isoxazol-3-amine;
5-fluoro-6-methyl-N-(1'-azaspiro[cyclopropane-1,2'-bicyclo[2.2.2]octan]-3'-yl)benzo[d]isoxazol-3-amine;
6-chloro-7-methyl-N-(1'-azaspiro[cyclopropane-1,2'-bicyclo[2.2.2]octan]-3'-yl)benzo[d]isoxazol-3-amine;
6-chloro-5-fluoro-N-(1'-azaspiro[cyclopropane-1,2'-bicyclo[2.2.2]octan]-3'-yl)benzo[d]isoxazol-3-amine;
6-chloro-7-ethoxy-N-(1'-azaspiro[cyclopropane-1,2'-bicyclo[2.2.2]octan]-3'-yl)benzo[d]isoxazol-3-amine;
7-chloro-6-methyl-N-(1'-azaspiro[cyclopropane-1,2'-bicyclo[2.2.2]octan]-3'-yl)benzo[d]isoxazol-3-amine;
6-chloro-N-(1'-azaspiro[cyclopropane-1,2'-bicyclo[2.2.2]octan]-3'-yl)-7-(trifluoromethyl)benzo[d]isoxazol-3-amine; and
6-chloro-7-isopropoxy-N-(1'-azaspiro[cyclopropane-1,2'-bicyclo[2.2.2]octan]-3'-yl)benzo[d]isoxazol-3-amine.

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the compounds listed below, and single enantiomers and pharmaceutically acceptable salts thereof:

6-chloro-7-(difluoromethyl)-N-(1'-azaspiro[cyclopropane-1,2'-bicyclo[2.2.2]octan]-3'-yl)benzo[d]isoxazol-3-amine;
6-chloro-7-(difluoromethyl)-N-(2,2-dimethylquinuclidin-3-yl)benzo[d]isoxazol-3-amine;
6-chloro-N-(1'-azaspiro[cyclopropane-1,2'-bicyclo[2.2.2]octan]-3'-yl)-7-(trifluoromethoxy)benzo[d]isoxazol-3-amine;
6-chloro-N-(2,2-dimethylquinuclidin-3-yl)-7-(trifluoromethoxy)benzo[d]isoxazol-3-amine;
6-chloro-7-cyclopropoxy-N-(1'-azaspiro[cyclopropane-1,2'-bicyclo[2.2.2]octan]-3'-yl)benzo[d]isoxazol-3-amine;
6-chloro-7-cyclopropoxy-N-(2,2-dimethylquinuclidin-3-yl)benzo[d]isoxazol-3-amine;
6-chloro-N-(1'-azaspiro[cyclopropane-1,2'-bicyclo[2.2.2]octan]-3'-yl)-7-(2,2,2-trifluoroethyl)benzo[d]isoxazol-3-amine;
6-chloro-N-(2,2-dimethylquinuclidin-3-yl)-7-(2,2,2-trifluoroethyl)benzo[d]isoxazol-3-amine;
6-chloro-N-(1'-azaspiro[cyclopropane-1,2'-bicyclo[2.2.2]octan]-3'-yl)-7-(2,2,2-trifluoroethoxy)benzo[d]isoxazol-3-amine;
6-chloro-N-(2,2-dimethylquinuclidin-3-yl)-7-(2,2,2-trifluoroethoxy)benzo[d]isoxazol-3-amine;
6-chloro-7-isopropyl-N-(1'-azaspiro[cyclopropane-1,2'-bicyclo[2.2.2]octan]-3'-yl)benzo[d]isoxazol-3-amine; and
6-chloro-N-(2,2-dimethylquinuclidin-3-yl)-7-isopropylbenzo[d]isoxazol-3-amine.

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the single enantiomers listed below, and pharmaceutically acceptable salts thereof:

(R)-6-chloro-N-(2,2-dimethylquinuclidin-3-yl)benzo[d]isoxazol-3-amine;
(S)-6-chloro-N-(2,2-dimethylquinuclidin-3-yl)benzo[d]isoxazol-3-amine;
(R)-6-chloro-N-(2,2-dimethylquinuclidin-3-yl)-7-fluorobenzo[d]isoxazol-3-amine;
(S)-6-chloro-N-(2,2-dimethylquinuclidin-3-yl)-7-fluorobenzo[d]isoxazol-3-amine;
(R)—N-(2,2-dimethylquinuclidin-3-yl)-6-methoxybenzo[d]isoxazol-3-amine;
(S)—N-(2,2-dimethylquinuclidin-3-yl)-6-methoxybenzo[d]isoxazol-3-amine;
(R)-6,7-dichloro-N-(2,2-dimethylquinuclidin-3-yl)benzo[d]isoxazol-3-amine;
(S)-6,7-dichloro-N-(2,2-dimethylquinuclidin-3-yl)benzo[d]isoxazol-3-amine;
(R)-6-chloro-N-(2,2-dimethylquinuclidin-3-yl)-7-methoxybenzo[d]isoxazol-3-amine;
(S)-6-chloro-N-(2,2-dimethylquinuclidin-3-yl)-7-methoxybenzo[d]isoxazol-3-amine;

(R)—N-(2,2-dimethylquinuclidin-3-yl)-6-methylbenzo[d]isoxazol-3-amine;
(S)—N-(2,2-dimethylquinuclidin-3-yl)-6-methylbenzo[d]isoxazol-3-amine;
(R)—N-(2,2-dimethylquinuclidin-3-yl)-7-fluoro-6-methylbenzo[d]isoxazol-3-amine;
(S)—N-(2,2-dimethylquinuclidin-3-yl)-7-fluoro-6-methylbenzo[d]isoxazol-3-amine;
(R)-7-chloro-N-(2,2-dimethylquinuclidin-3-yl)-6-fluorobenzo[d]isoxazol-3-amine;
(S)-7-chloro-N-(2,2-dimethylquinuclidin-3-yl)-6-fluorobenzo[d]isoxazol-3-amine;
(R)—N-(2,2-dimethylquinuclidin-3-yl)-5-fluoro-6-methylbenzo[d]isoxazol-3-amine;
(S)—N-(2,2-dimethylquinuclidin-3-yl)-5-fluoro-6-methylbenzo[d]isoxazol-3-amine;
(R)-6-chloro-N-(2,2-dimethylquinuclidin-3-yl)-7-methylbenzo[d]isoxazol-3-amine;
(S)-6-chloro-N-(2,2-dimethylquinuclidin-3-yl)-7-methylbenzo[d]isoxazol-3-amine;
(R)-6-chloro-N-(2,2-dimethylquinuclidin-3-yl)-5-fluorobenzo[d]isoxazol-3-amine;
(S)-6-chloro-N-(2,2-dimethylquinuclidin-3-yl)-5-fluorobenzo[d]isoxazol-3-amine;
(R)-6-chloro-N-(2,2-dimethylquinuclidin-3-yl)-7-ethoxybenzo[d]isoxazol-3-amine;
(S)-6-chloro-N-(2,2-dimethylquinuclidin-3-yl)-7-ethoxybenzo[d]isoxazol-3-amine;
(R)-7-chloro-N-(2,2-dimethylquinuclidin-3-yl)-6-methylbenzo[d]isoxazol-3-amine;
(S)-7-chloro-N-(2,2-dimethylquinuclidin-3-yl)-6-methylbenzo[d]isoxazol-3-amine;
(R)-6-chloro-N-(2,2-dimethylquinuclidin-3-yl)-7-(trifluoromethyl)benzo[d]isoxazol-3-amine;
(S)-6-chloro-N-(2,2-dimethylquinuclidin-3-yl)-7-(trifluoromethyl)benzo[d]isoxazol-3-amine;
(R)-6-chloro-N-(2,2-dimethylquinuclidin-3-yl)-7-isopropoxybenzo[d]isoxazol-3-amine;
(S)-6-chloro-N-(2,2-dimethylquinuclidin-3-yl)-7-isopropoxybenzo[d]isoxazol-3-amine;
(R)-6-chloro-N-(1'-azaspiro[cyclopropane-1,2'-bicyclo[2.2.2]octan]-3'-yl)benzo[d]isoxazol-3-amine;
(S)-6-chloro-N-(1'-azaspiro[cyclopropane-1,2'-bicyclo[2.2.2]octan]-3'-yl)benzo[d]isoxazol-3-amine;
(R)-6-chloro-7-fluoro-N-(1'-azaspiro[cyclopropane-1,2'-bicyclo[2.2.2]octan]-3'-yl)benzo[d]isoxazol-3-amine;
(S)-6-chloro-7-fluoro-N-(1'-azaspiro[cyclopropane-1,2'-bicyclo[2.2.2]octan]-3'-yl)benzo[d]isoxazol-3-amine;
(R)-6-methoxy-N-(1'-azaspiro[cyclopropane-1,2'-bicyclo[2.2.2]octan]-3'-yl)benzo[d]isoxazol-3-amine;
(S)-6-methoxy-N-(1'-azaspiro[cyclopropane-1,2'-bicyclo[2.2.2]octan]-3'-yl)benzo[d]isoxazol-3-amine;
(R)-6,7-dichloro-N-(1'-azaspiro[cyclopropane-1,2'-bicyclo[2.2.2]octan]-3'-yl)benzo[d]isoxazol-3-amine;
(S)-6,7-dichloro-N-(1'-azaspiro[cyclopropane-1,2'-bicyclo[2.2.2]octan]-3'-yl)benzo[d]isoxazol-3-amine;
(R)-6-chloro-7-methoxy-N-(1'-azaspiro[cyclopropane-1,2'-bicyclo[2.2.2]octan]-3'-yl)benzo[d]isoxazol-3-amine;
(S)-6-chloro-7-methoxy-N-(1'-azaspiro[cyclopropane-1,2'-bicyclo[2.2.2]octan]-3'-yl)benzo[d]isoxazol-3-amine;
(R)-6-methyl-N-(1'-azaspiro[cyclopropane-1,2'-bicyclo[2.2.2]octan]-3'-yl)benzo[d]isoxazol-3-amine;
(S)-6-methyl-N-(1'-azaspiro[cyclopropane-1,2'-bicyclo[2.2.2]octan]-3'-yl)benzo[d]isoxazol-3-amine;
(R)-7-fluoro-6-methyl-N-(1'-azaspiro[cyclopropane-1,2'-bicyclo[2.2.2]octan]-3'-yl)benzo[d]isoxazol-3-amine;
(S)-7-fluoro-6-methyl-N-(1'-azaspiro[cyclopropane-1,2'-bicyclo[2.2.2]octan]-3'-yl)benzo[d]isoxazol-3-amine;
(R)-7-chloro-6-fluoro-N-(1'-azaspiro[cyclopropane-1,2'-bicyclo[2.2.2]octan]-3'-yl)benzo[d]isoxazol-3-amine;
(S)-7-chloro-6-fluoro-N-(1'-azaspiro[cyclopropane-1,2'-bicyclo[2.2.2]octan]-3'-yl)benzo[d]isoxazol-3-amine;
(R)-5-fluoro-6-methyl-N-(1'-azaspiro[cyclopropane-1,2'-bicyclo[2.2.2]octan]-3'-yl)benzo[d]isoxazol-3-amine;
(S)-5-fluoro-6-methyl-N-(1'-azaspiro[cyclopropane-1,2'-bicyclo[2.2.2]octan]-3'-yl)benzo[d]isoxazol-3-amine;
(R)-6-chloro-7-methyl-N-(1'-azaspiro[cyclopropane-1,2'-bicyclo[2.2.2]octan]-3'-yl)benzo[d]isoxazol-3-amine;
(S)-6-chloro-7-methyl-N-(1'-azaspiro[cyclopropane-1,2'-bicyclo[2.2.2]octan]-3'-yl)benzo[d]isoxazol-3-amine;
(R)-6-chloro-5-fluoro-N-(1'-azaspiro[cyclopropane-1,2'-bicyclo[2.2.2]octan]-3'-yl)benzo[d]isoxazol-3-amine;
(S)-6-chloro-5-fluoro-N-(1'-azaspiro[cyclopropane-1,2'-bicyclo[2.2.2]octan]-3'-yl)benzo[d]isoxazol-3-amine;
(R)-6-chloro-7-ethoxy-N-(1'-azaspiro[cyclopropane-1,2'-bicyclo[2.2.2]octan]-3'-yl)benzo[d]isoxazol-3-amine;
(S)-6-chloro-7-ethoxy-N-(1'-azaspiro[cyclopropane-1,2'-bicyclo[2.2.2]octan]-3'-yl)benzo[d]isoxazol-3-amine;
(R)-7-chloro-6-methyl-N-(1'-azaspiro[cyclopropane-1,2'-bicyclo[2.2.2]octan]-3'-yl)benzo[d]isoxazol-3-amine;
(S)-7-chloro-6-methyl-N-(1'-azaspiro[cyclopropane-1,2'-bicyclo[2.2.2]octan]-3'-yl)benzo[d]isoxazol-3-amine;
(R)-6-chloro-N-(1'-azaspiro[cyclopropane-1,2'-bicyclo[2.2.2]octan]-3'-yl)-7-(trifluoromethyl)benzo[d]isoxazol-3-amine;
(S)-6-chloro-N-(1'-azaspiro[cyclopropane-1,2'-bicyclo[2.2.2]octan]-3'-yl)-7-(trifluoromethyl)benzo[d]isoxazol-3-amine;
(R)-6-chloro-7-isopropoxy-N-(1'-azaspiro[cyclopropane-1,2'-bicyclo[2.2.2]octan]-3'-yl)benzo[d]isoxazol-3-amine; and
(S)-6-chloro-7-isopropoxy-N-(1'-azaspiro[cyclopropane-1,2'-bicyclo[2.2.2]octan]-3'-yl)benzo[d]isoxazol-3-amine.

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the single enantiomers listed below, and pharmaceutically acceptable salts thereof:

(R)-6-chloro-7-(difluoromethyl)-N-(1'-azaspiro[cyclopropane-1,2'-bicyclo[2.2.2]octan]-3'-yl)benzo[d]isoxazol-3-amine;
(S)-6-chloro-7-(difluoromethyl)-N-(1'-azaspiro[cyclopropane-1,2'-bicyclo[2.2.2]octan]-3'-yl)benzo[d]isoxazol-3-amine;
(R)-6-chloro-7-(difluoromethyl)-N-(2,2-dimethylquinuclidin-3-yl)benzo[d]isoxazol-3-amine;
(S)-6-chloro-7-(difluoromethyl)-N-(2,2-dimethylquinuclidin-3-yl)benzo[d]isoxazol-3-amine;
(R)-6-chloro-N-(1'-azaspiro[cyclopropane-1,2'-bicyclo[2.2.2]octan]-3'-yl)-7-(trifluoromethoxy)benzo[d]isoxazol-3-amine;
(S)-6-chloro-N-(1'-azaspiro[cyclopropane-1,2'-bicyclo[2.2.2]octan]-3'-yl)-7-(trifluoromethoxy)benzo[d]isoxazol-3-amine;
(R)-6-chloro-N-(2,2-dimethylquinuclidin-3-yl)-7-(trifluoromethoxy)benzo[d]isoxazol-3-amine;
(S)-6-chloro-N-(2,2-dimethylquinuclidin-3-yl)-7-(trifluoromethoxy)benzo[d]isoxazol-3-amine;
(R)-6-chloro-7-cyclopropoxy-N-(1'-azaspiro[cyclopropane-1,2'-bicyclo[2.2.2]octan]-3'-yl)benzo[d]isoxazol-3-amine;

(S)-6-chloro-7-cyclopropoxy-N-(1'-azaspiro[cyclopropane-1,2'-bicyclo[2.2.2]octan]-3'-yl)benzo[d]isoxazol-3-amine;
(R)-6-chloro-7-cyclopropoxy-N-(2,2-dimethylquinuclidin-3-yl)benzo[d]isoxazol-3-amine;
(S)-6-chloro-7-cyclopropoxy-N-(2,2-dimethylquinuclidin-3-yl)benzo[d]isoxazol-3-amine;
(R)-6-chloro-N-(1'-azaspiro[cyclopropane-1,2'-bicyclo[2.2.2]octan]-3'-yl)-7-(2,2,2-trifluoroethyl)benzo[d]isoxazol-3-amine;
(S)-6-chloro-N-(1'-azaspiro[cyclopropane-1,2'-bicyclo[2.2.2]octan]-3'-yl)-7-(2,2,2-trifluoroethyl)benzo[d]isoxazol-3-amine;
(R)-6-chloro-N-(2,2-dimethylquinuclidin-3-yl)-7-(2,2,2-trifluoroethyl)benzo[d]isoxazol-3-amine;
(S)-6-chloro-N-(2,2-dimethylquinuclidin-3-yl)-7-(2,2,2-trifluoroethyl)benzo[d]isoxazol-3-amine;
(R)-6-chloro-N-(1'-azaspiro[cyclopropane-1,2'-bicyclo[2.2.2]octan]-3'-yl)-7-(2,2,2-trifluoroethoxy)benzo[d]isoxazol-3-amine;
(S)-6-chloro-N-(1'-azaspiro[cyclopropane-1,2'-bicyclo[2.2.2]octan]-3'-yl)-7-(2,2,2-trifluoroethoxy)benzo[d]isoxazol-3-amine;
(R)-6-chloro-N-(2,2-dimethylquinuclidin-3-yl)-7-(2,2,2-trifluoroethoxy)benzo[d]isoxazol-3-amine;
(S)-6-chloro-N-(2,2-dimethylquinuclidin-3-yl)-7-(2,2,2-trifluoroethoxy)benzo[d]isoxazol-3-amine;
(R)-6-chloro-7-isopropyl-N-(1'-azaspiro[cyclopropane-1,2'-bicyclo[2.2.2]octan]-3'-yl)benzo[d]isoxazol-3-amine;
(S)-6-chloro-7-isopropyl-N-(1'-azaspiro[cyclopropane-1,2'-bicyclo[2.2.2]octan]-3'-yl)benzo[d]isoxazol-3-amine;
(R)-6-chloro-N-(2,2-dimethylquinuclidin-3-yl)-7-isopropylbenzo[d]isoxazol-3-amine; and
(S)-6-chloro-N-(2,2-dimethylquinuclidin-3-yl)-7-isopropylbenzo[d]isoxazol-3-amine.

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the single enantiomers listed below, and pharmaceutically acceptable salts thereof:

(R)-6-chloro-N-(2,2-dimethylquinuclidin-3-yl)benzo[d]isoxazol-3-amine;
(R)-6-chloro-N-(2,2-dimethylquinuclidin-3-yl)-7-fluorobenzo[d]isoxazol-3-amine;
(R)-6,7-dichloro-N-(2,2-dimethylquinuclidin-3-yl)benzo[d]isoxazol-3-amine;
(R)-6-chloro-N-(2,2-dimethylquinuclidin-3-yl)-7-methoxybenzo[d]isoxazol-3-amine;
(R)—N-(2,2-dimethylquinuclidin-3-yl)-6-methylbenzo[d]isoxazol-3-amine;
(R)-7-chloro-N-(2,2-dimethylquinuclidin-3-yl)-6-fluorobenzo[d]isoxazol-3-amine;
(R)-6-chloro-N-(2,2-dimethylquinuclidin-3-yl)-7-methylbenzo[d]isoxazol-3-amine;
(R)-6-chloro-N-(1'-azaspiro[cyclopropane-1,2'-bicyclo[2.2.2]octan]-3'-yl)benzo[d]isoxazol-3-amine;
(R)-6-methoxy-N-(1'-azaspiro[cyclopropane-1,2'-bicyclo[2.2.2]octan]-3'-yl)benzo[d]isoxazol-3-amine; and
(R)-7-fluoro-6-methyl-N-(1'-azaspiro[cyclopropane-1,2'-bicyclo[2.2.2]octan]-3'-yl)benzo[d]isoxazol-3-amine.

In certain embodiments, specific examples of the geminal substituted aminobenzisoxazole compound represented by Formula (Ia) or (Ib), Formula (IIa) or (IIb), or Formula (IIIa) or (IIIb) may include, collectively or individually, the single enantiomers listed below, and pharmaceutically acceptable salts thereof:

(R)-6-chloro-N-(2,2-dimethylquinuclidin-3-yl)-7-fluorobenzo[d]isoxazol-3-amine;
(R)-6,7-dichloro-N-(2,2-dimethylquinuclidin-3-yl)benzo[d]isoxazol-3-amine;
(R)-6-chloro-N-(2,2-dimethylquinuclidin-3-yl)-7-methoxybenzo[d]isoxazol-3-amine; and
(R)-6-chloro-N-(1'-azaspiro[cyclopropane-1,2'-bicyclo[2.2.2]octan]-3'-yl)benzo[d]isoxazol-3-amine.

In certain embodiments, the geminal substituted aminobenzisoxazole compounds of the present invention represented by Formula (Ia) or (Ib), Formula (IIa) or (IIb), or Formula (IIIa) or (IIIb), or a pharmaceutically acceptable salt thereof, may be more potent against α7 nAChR (according to the α7 nAChR Binding Assay (Ki)) than against a 5-HT$_3$ serotonin receptor (according to the [$^3$H]BRL 43694 competition binding (Ki)). For example, the geminal substituted aminobenzisoxazole compounds of the present invention represented by Formula (Ia) or (Ib), Formula (IIa) or (IIb), or Formula (IIIa) or (IIIb), or a pharmaceutically acceptable salt thereof, may be at least 1.5 times more potent against α7 nAChR than against a 5-HT$_3$ serotonin receptor, as determined by the α7 nAChR Binding Assay and the [$^3$H]BRL 43694 competition binding assay, respectively, such as at least 2 times more potent, at least 3 times more potent, at least 4 times more potent, at least 5 times more potent, at least 6 times more potent, at least 7 times more potent, at least 8 times more potent, at least 9 times more potent, at least 10 times more potent, at least 15 times more potent, at least 20 times more potent, or at least 25 times more potent against α7 nAChR than against a 5-HT$_3$ serotonin receptor, as determined by the α7 nAChR Binding Assay and the [$^3$H]BRL 43694 competition binding assay, respectively.

As used herein, the term "treating" (or "treat" or "treatment"), unless otherwise specified, includes the generally accepted meaning which encompasses improving, modifying, decreasing, prohibiting, preventing, restraining, minimizing, slowing, halting, stopping, curing, and/or reversing a symptom associated with a disease and/or a disease. Treatment may include both therapeutic and prophylactic administration. For example, treatment of a cognitive impairment, in a patient diagnosed as having a cognitive impairment, may include, but is not limited to, curing the cognitive impairment, preventing the deterioration of one or more symptoms associated with the cognitive impairment; improving cognition in a patient suffering from the cognitive impairment, slowing the progression of the cognitive impairment and/or modifying the cognitive impairment.

As used herein, the term "effective dose" (or "dose"), unless otherwise specified, is understood to include a therapeutically acceptable dose, a therapeutically acceptable amount, a therapeutically effective dose, a therapeutically effective amount, a pharmaceutically acceptable dose, a pharmaceutically acceptable amount, a pharmaceutically effective dose, or a pharmaceutically effective amount.

As used herein, the term "cognitive impairment," unless otherwise specified, includes at least one of the following: Limited Cognitive Impairment (LCI), Mild Cognitive Impairment (MCI), Alzheimer's disease (or dementia of an Alzheimer's-type) or a particular stage of Alzheimer's disease, inclusive of pre-Alzheimer's disease, early Alzheimer's disease, mild Alzheimer's disease, moderate Alzheimer's disease, severe Alzheimer's disease, pre-Alzheimer's-to-mild Alzheimer's disease, mild-to-moderate Alzheimer's disease, moderate-to-severe Alzheimer's disease, schizophrenia (for example, paranoid type schizophrenia, disorganized type schizophrenia, catatonic type schizophrenia, undifferentiated type schizophrenia), cognitive impairment associated with schizophrenia, schizophreniform disorder, schizoaffective disorder, delusional disorder, positive symptoms of schizophrenia, negative symptoms of schizophrenia, or schizophrenia with dementia.

Alzheimer's disease may include, unless otherwise specified, any of the sub-diagnostic categories used to characterize the type or degree of cognitive impairment in a patient for treatment purposes. A commonly referenced diagnostic scale for characterizing the degree of cognitive impairment for a patient with Alzheimer's disease includes the 3-stage Alzheimer Disease Model. The 3-stages consist of: mild stage (also referred to as "early Alzheimer's disease" or "mild Alzheimer's disease" or "early stage Alzheimer's disease" or "mild dementia of an Alzheimer's-type"), moderate stage (also referred to as "middle Alzheimer's disease" or "moderate Alzheimer's disease" or "middle stage Alzheimer's disease" or "moderate dementia of an Alzheimer's-type"), and severe stage (also referred to as "late Alzheimer's disease" or "severe Alzheimer's disease" or "late stage Alzheimer's disease" or "severe dementia of an Alzheimer's-type"). For patients with a condition that has not progressed to the point of mild stage Alzheimer's disease, they may be diagnosed as having pre-Alzheimer's disease. It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. Another useful diagnostic scale that is used in characterizing the degree of cognitive impairment for a patient having Alzheimer's disease is the Seven Stage Alzheimer's Disease Model (sometimes known as the "Seven Stage Global Deterioration Scale" or the "Reisberg Scale"). This diagnostic scale divides the progression of the cognitive disorder associated with Alzheimer's disease as follows: Stage 1-no Alzheimer's disease (generally characterized by absence of impairment, no impairment, or normal function), Stage 2-pre-Alzheimer's disease (generally characterized by minimal impairment, normal forgetfulness, or very mild cognitive decline), Stage 3-early-stage Alzheimer's disease (generally characterized by a noticeable cognitive decline, early confusional/mild cognitive impairment, or mild cognitive decline), Stage 4-early-stage/mild Alzheimer's disease (also referred to as late confusional/mild Alzheimer's, and generally characterized by moderate cognitive decline), Stage 5-middle-stage/moderate Alzheimer's (also referred to as early dementia/moderate Alzheimer's disease and generally characterized by moderately severe cognitive decline), Stage 6-middle dementia/moderately severe Alzheimer's disease (also referred to as middle-stage/moderate to late-stage/severe Alzheimer's disease and generally characterized by severe cognitive decline), and Stage 7-late-stage/severe Alzheimer's disease (also referred to as severe dementia or failure-to-thrive, and generally characterized by very severe cognitive decline). It is also not uncommon for treatment purposes to characterize stages together, such as pre-Alzheimer's disease-to-mild stage Alzheimer's disease, mild-to-moderate Alzheimer's disease, or moderate-to-severe Alzheimer's disease. As used herein, unless otherwise specified, Alzheimer's disease includes all of the above named diagnostic categories or disease characterizations. It is also not uncommon for a physician to categorize any one or more of the above noted states of Alzheimer's disease as being probable, for example, probable mild-to-moderate Alzheimer's disease or probable severe Alzheimer's disease, when their diagnosis does not include, for example a physical biopsy or other definitive analysis.

Mild Cognitive Impairment (MCI) is considered by some to be an intermediate stage between normal aging and the onset of Alzheimer's disease. For example, MCI may be characterized by persistent forgetfulness, but may lack some or many of the more debilitating symptoms of Alzheimer's disease. Another set of criteria that may characterize a patient as having mild cognitive impairment suitable for treatment includes a patient that meets the following: 1) memory complaints corroborated by an informant, 2) objective memory impairment for age and education, 3) normal general cognitive function, 4) intact activities of daily living, and 5) the patient does not meet criteria for dementia. In general, a patient characterized as having mild cognitive impairment may not yet have a clinical cognitive deficit. Mild cognitive impairment may also be distinguished from senile dementia in that mild cognitive impairment involves a more persistent and troublesome problem of memory loss for the age of the patient. On the clinical diagnostic scale, mild cognitive impairment is followed, in increased severity, by Alzheimer's disease.

Limited Cognitive Impairment (LCI) describes a cognitive impairment (i.e., symptoms or conditions), which precedes mild cognitive impairment on a clinical diagnostic scale, and includes any chronic or temporary impairment in cognition, learning or memory that prevents or reduces the ability of a patient from achieving their individual potential in these areas. For example, LCIs may include minor impairments to memory associated with focus and concentration (e.g., accuracy and speed of learning and recalling information), working memory (e.g., used in decision making and problem solving), cognition, focus, mental quickness, and mental clarity.

The term "stereoisomer" refers to a molecule capable of existing in more than one spatial atomic arrangement for a given atomic connectivity (e.g., enantiomers, meso compounds, and diastereomers). As used herein, the term "stereoisomer" means either or both enantiomers and diastereomers.

The geminal substituted aminobenzisoxazole compounds of the present invention represented by Formula (Ia) or (Ib), Formula (IIa) or (IIb), or Formula (IIIa) or (IIIb), or a pharmaceutically acceptable salt thereof, may contain one or more stereogenic centers. Accordingly, compounds of this invention can exist as either individual stereoisomers or mixtures of two or more stereoisomers. A compound of the present invention will include both mixtures (e.g., racemic mixtures) and also individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, less than 2% of other stereoisomers, or less than "X"% of other stereoisomers (wherein X is a number between 0 and 100, inclusive) are present.

The geminal substituted aminobenzisoxazole compounds of the present invention represented by Formula (Ia) or (Ib), Formula (IIa) or (IIb), or Formula (IIIa) or (IIIb), or a pharmaceutically acceptable salt thereof, may contain one or more tautomeric forms. Accordingly, compounds of this invention can exist as either individual tautomers or mixtures of tautomeric forms. A compound of the present invention will include both mixtures (e.g., mixtures of tautomeric forms) and also individual respective tautomers that are substantially free from another possible tautomer.

The geminal substituted aminobenzisoxazole compounds of the present invention represented by Formula (Ia) or (Ib), Formula (IIa) or (IIb), or Formula (IIIa) or (IIIb), or a pharmaceutically acceptable salt thereof, may contain one or more geometric isomers. Accordingly, compounds of this invention can exist as either geometric isomers or mixtures of geometric isomers. A compound of the present invention will include both mixtures (e.g., mixtures of geometric isomers) and also individual respective geometric isomers that are substantially free from another possible geometric isomer.

The term "haloalkyl" refers to an alky group having from 1 to 5 halogen substituents independently selected from —F, —Cl, —Br, and —I. For example, a haloalkyl may represent a —$CF_3$ group, a —$CCl_3$ group, a —$CH_2CF_3$ group, or a —$CF_2CF_3$ group.

The term "heteroaryl" refers to an aromatic ring system comprising at least one or more hetero-ring atoms, such as two, three, four, or five hetero-ring atoms, independently selected from N, O, and S. Suitable heteroaryl groups may include a single ring, for example, thienyl, pyridyl, thiazolyl, pyrazinyl, pyrimidyl, imidazolyl, furanyl, isothiazolyl, pyrazolyl, triazolyl, tetrazolyl, isoxazolyl, oxazolyl, pyrrolyl, pyridazinyl, triazinyl, oxadiazolyl, and furazanyl. Suitable heteroaryl groups may include a fused ring system, for example, a six-six fused ring system, a six-five fused ring system, or a five-six fused ring system, such as benzothienyl, quinolyl, benzofuranyl, benzothiazolyl, benzisothiazolyl, benzisoxazolyl, benzimidazolyl, indolyl, benzoxazolyl, isoquinolinyl, cinnolinyl, indazolyl, indolizinyl, phthalazinyl, isoindolyl, purinyl, benzofurazanyl, benzothiophenyl, benzothiazolyl, quinazolinyl, quinoxalinyl, naphthridinyl, and furopyridinyl.

Suitable "heterocycloalkyl" groups include those having at least one or more hetero-ring atoms, such as two or three hetero-ring atoms, independently selected from at least one ring atom selected from the group consisting of oxygen, nitrogen, and sulfur, with the proviso that when the at least one ring atom is nitrogen, the nitrogen is independently substituted with —H, an unbranched $C_1$-$C_4$-alkyl radical, a branched $C_3$-$C_4$-alkyl radical, a $C_3$-$C_4$-cycloalkyl radical, —(CO)-unbranched $C_1$-$C_4$-alkyl, —(CO)-branched $C_3$-$C_4$-alkyl, —($SO_2$)-unbranched $C_1$-$C_4$-alkyl, or —($SO_2$)-branched $C_3$-$C_4$-alkyl, and with the further proviso that when the at least one ring atom is sulfur, the sulfur may be independently substituted with 0 to 2 =O. Suitable heterocycloalkyl groups may include, for example, tetrahydrofurano, tetrahydropyrano, morpholino, pyrrolidino, piperidino, piperazino, azetidino, azetidinono, oxindolo, oxetano, dihydroimidazolo, and pyrrolidinono.

The pharmaceutically acceptable salt of the geminal substituted aminobenzisoxazole compounds represented by Formula (Ia) or (Ib), Formula (IIa) or (IIb), or Formula (IIIa) or (IIIb), according to the present invention may be acid addition salts with inorganic or organic acids. Specific examples of these salts include acid addition salts with, for instance, mineral acids such as hydrochloric acid, hydrobromic acid, hydriodic acid, sulfuric acid, nitric acid or phosphoric acid; organic acids, for example carboxylic acids or sulfonic acids, such as formic acid, acetic acid, propionic acid, oxalic acid, malonic acid, succinic acid, fumaric acid, maleic acid, lactic acid, malic acid, tartaric acid, citric acid, benzoic acid, p-toluenesulfonic acid, benzenesulfonic acid, naphthalenedisulfonic acid, isethionic acid, glucuronic acid, gluconic acid, methanesulfonic acid or ethanesulfonic acid; or acidic amino acids such as aspartic acid or glutamic acid.

In certain embodiments, a pharmaceutical composition may comprise a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

In certain embodiments, the geminal substituted aminobenzisoxazole compounds represented by Formula (Ia) or (Ib), Formula (IIa) or (IIb), or Formula (IIIa) or (IIIb), or a pharmaceutically acceptable salt thereof, are suitable for use as medicaments for the treatment and/or prophylaxis of diseases in humans and/or animals.

In certain embodiments, the invention relates to a method comprising administering to a patient in need thereof an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

In certain embodiments, the geminal substituted aminobenzisoxazole compound represented by Formula (Ia) or (Ib), Formula (IIa) or (IIb), or Formula (IIIa) or (IIIb), or a pharmaceutically acceptable salt thereof, act as ligands, in particular as α7-nAChR agonists.

In certain embodiments, a method of treating a patient in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. In certain embodiments, a method of treating a patient in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof. For example, the patient may suffer from a cognitive impairment or suffers from one or more symptoms associated with a cognitive impairment, such as Limited Cognitive Impairment (LCI), Mild Cognitive Impairment (MCI), Alzheimer's disease, dementia of an Alzheimer's-type, schizophrenia, schizophreniform disorder, schizoaffective disorder, delusional disorder, positive symptoms of schizophrenia, negative symptoms of schizophrenia, schizophrenia with dementia, or major depressive disorder.

In certain embodiments, a method of treating Alzheimer's disease, such as preventing the progression or disease modification of the Alzheimer's disease, in a patient in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. For example, in certain embodiments, a method of treating Alzheimer's disease, such as preventing the progression or disease modification of the Alzheimer's disease, in a patient in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof. In certain embodiments, a method of treating cognitive impairment associated with Alzheimer's disease, such as preventing the progression or disease modification of the Alzheimer's disease, in a patient in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. For example, in certain embodiments, a method of treating cognitive impairment associated with Alzheimer's disease, such as preventing the progression or disease modification of the Alzheimer's disease, in a patient in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof.

In certain embodiments, a method of treating dementia of an Alzheimer's-type in a patient, such as preventing the progression or disease modification of the dementia of an Alzheimer's-type, in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. For example, in certain embodiments, a method of treating dementia of an Alzheimer's-type in a patient, such as preventing the progression or disease modification of the dementia of an Alzheimer's-type, in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof. In certain embodiments, a method of treating cognitive impairment associated with dementia of an Alzheimer's-type in a patient, such as preventing the progression or disease modification of the dementia of an Alzheimer's-type, in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. For example, in certain embodiments, a method of treating cognitive impairment associated with dementia of an Alzheimer's-type in a patient, such as preventing the progression or disease modification of the dementia of an Alzheimer's-type, in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof.

In certain embodiments, a method of treating cognitive impairment associated with schizophrenia in a patient in need thereof, comprising administering a geminal substituted aminobenzisoxazole compound represented by Formula (Ia) or (Ib), Formula (IIa) or (IIb), or Formula (IIIa) or (IIIb), or a pharmaceutically acceptable salt thereof. In certain embodiments, a method of treating cognitive impairment associated with schizophrenia in a patient in need thereof, comprising administering a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof.

In certain embodiments, the geminal substituted aminobenzisoxazole compounds represented by Formula (Ia) or (Ib), Formula (IIa) or (IIb), or Formula (IIIa) or (IIIb), or a pharmaceutically acceptable salt thereof, can, because of their pharmacological properties, be employed, alone or in combination with other active ingredients, for the treatment and/or prevention of cognitive impairments, for example, Alzheimer's disease, dementia of an Alzheimer's-type, or schizophrenia. Because of their selective effect as α7-nAChR agonists, the geminal substituted aminobenzisoxazole compounds represented by Formula (Ia) or (Ib), Formula (IIa) or (IIb), or Formula (IIIa) or (IIIb), or a pharmaceutically acceptable salt thereof, are particularly suitable for improving cognition, providing procognitive effects, improving perception, improving concentration, improving learning or memory, improving one or more aspects of cognition, e.g., one or more of: executive function, memory (e.g., working memory), social cognition, visual learning, verbal learning and speed of processing, especially after or associated with cognitive impairments like those occurring for example in situations/diseases/syndromes such as mild cognitive impairment, age-associated learning and memory impairments, age-associated memory loss, vascular dementia, craniocerebral trauma, stroke, dementia occurring after strokes (post-stroke dementia), post-traumatic brain syndrome, post-traumatic stress disorder, general concentration impairments, concentration impairments in children with learning and memory problems, attention deficit hyperactivity disorder, autism spectrum disorder, Fragile X syndrome, Alzheimer's disease, Lewy body dementia, dementia with degeneration of the frontal lobes, including Pick's syndrome, frontotemporal dementia, Parkinson's disease, dyskinesias associated with dopamine agonist therapy in Parkinson's Disease, progressive nuclear palsy, dementia with corticobasal degeneration, amyotrophic lateral sclerosis (ALS), Huntington's disease, multiple sclerosis, thalamic degeneration, Creutzfeld-Jakob dementia, HIV dementia, schizophrenia (e.g., paranoid type, disorganized type, catatonic type, and undifferentiated type), schizophreniform disorder, schizoaffective disorder, delusional disorder, positive symptoms of schizophrenia, negative symptoms of schizophrenia, schizophrenia with dementia, Korsakoff's psychosis, depression, anxiety, mood and affective disorders, bipolar disorder, major depressive disorder, traumatic brain injury, chronic traumatic encephalopathy, withdrawal symptoms associated with smoking cessation and dependent drug cessation, Gilles de la Tourette's Syndrome, age-related macular degeneration, glaucoma, neurodegeneration associated with glaucoma, treatment of cognitive deficits following coronary artery bypass graft surgery, treatment (including amelioration, prevention or delay of progression) of sleep disorders (e.g., narcolepsy, excessive daytime sleepiness, nocturnal sleep disruption and/or cataplexy), cognitive deficits associated with sleep disorders, treatment (including amelioration, prevention or delay) of progression of fatigue, or use for facilitation of emergence from general anesthesia.

In certain embodiments, the geminal substituted aminobenzisoxazole compounds represented by Formula (Ia) or (Ib), Formula (IIa) or (IIb), or Formula (IIIa) or (IIIb), or a pharmaceutically acceptable salt thereof, can be employed alone or in combination with other active ingredients for the prophylaxis and treatment of acute and/or chronic pain (for a classification, see "Classification of Chronic Pain, Descriptions of Chronic Pain Syndromes and Definitions of Pain Terms", $2^{nd}$ edition, Meskey and Begduk, editors; IASP Press, Seattle, 1994), especially for the treatment of cancer-induced pain and chronic neuropathic pain like, for example, that associated with diabetic neuropathy, postherpetic neuralgia, peripheral nerve damage, central pain (for example as a consequence of cerebral ischaemia) and trigeminal neuralgia, and other chronic pain such as, for example, lumbago, backache, or rheumatic pain. In addition, these active ingredients are also suitable for the therapy of primary acute pain of any origin and of secondary states of pain resulting therefrom, and for the therapy of states of pain which were formerly acute and have become chronic.

In certain embodiments, the invention relates to a method comprising administering to a patient in need thereof, such as a patient suffering from, or diagnosed as having, a cognitive impairment or having one or more symptoms associated with a cognitive impairment, an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent. For example, the method may treat and/or improve the one or more symptoms associated with a cognitive impairment and/or the cognitive impairment. For example, in certain embodiments, the cognitive impairment is Alzheimer's disease, dementia of an Alzheimer's type, or schizophrenia.

A certain embodiment of the present invention provides a method of improving one or more cognitive symptoms, improving one or more behavioral symptoms, or both, associated with a cognitive impairment, comprising: administering to a patient in need thereof an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent. For example, in certain embodiments, the cognitive impairment is Alzheimer's disease, dementia of an Alzheimer's type, or schizophrenia.

In a certain embodiment of the present invention, the method provides a pro-cognitive effect in a patient suffering from, or diagnosed as having, a cognitive disease or dementia, comprising: administering to a patient in need thereof an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, or administering to the patient a pharmaceutical composition comprising an effective dose of the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

A certain embodiment of the present invention provides a method of treating a patient with a cognitive disease, comprising: administering to the patient a daily dose of a pharmaceutical composition comprising a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

In a certain embodiment of the present invention, the method provides a pro-cognitive effect in a patient suffering from, or diagnosed as having, schizophrenia, for example, paranoid type schizophrenia, disorganized type schizophrenia, catatonic type schizophrenia, undifferentiated type schizophrenia, schizophreniform disorder, schizoaffective disorder, delusional disorder, positive symptoms of schizophrenia, negative symptoms of schizophrenia, or schizophrenia with dementia, comprising: administering to a patient in need thereof an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, or administering to a patient in need thereof, a pharmaceutical composition comprising an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluents; wherein the method provides at least one of the following: visual motor, learning, delayed memory, or executive function; for example provides a pro-cognitive effect, exclusive of attention, in said patient; for example provides a pro-cognitive effect in at least one of the following: visual motor, learning, delayed memory, or executive function.

In an embodiment of the present invention, any one of the above-noted embodiments, includes wherein the daily dose is an initial daily dose.

In a certain embodiment of the present invention provides a method of improving cognition of a patient in need thereof, comprising: administering to the patient a geminal substituted aminobenzisoxazole compound represented by Formula (Ia) or (Ib), Formula (IIa) or (IIb), or Formula (IIIa) or (IIIb), or a pharmaceutically acceptable salt thereof, or administering to the patient a pharmaceutical composition comprising an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluents. For example, in certain embodiments, the present invention provides a method of improving cognition in a patient suffering from Alzheimer's disease, dementia of an Alzheimer's type, or schizophrenia, comprises: administering to the patient a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluents.

In a certain embodiment of the present invention provides a method of treating or improving one or more symptoms associated with a cognitive disease and/or a cognitive impairment in a patient in need thereof, comprising: administering to the patient an effective dose of a geminal substituted aminobenzisoxazole compound represented by Formula (Ia) or (Ib), Formula (IIa) or (IIb), or Formula (IIIa) or (IIIb), or a pharmaceutically acceptable salt thereof; or administering to the patient a pharmaceutical composition comprising the geminal substituted aminobenzisoxazole compound represented by Formula (Ia) or (Ib), Formula (IIa) or (IIb), or Formula (IIIa) or (IIIb), or a pharmaceutically acceptable salt thereof, and at least one pharmaceutically acceptable carrier, excipient or diluent.

In an embodiment of the present invention, any one of the above-noted embodiments, wherein the method specifically includes treating a symptom associated with a cognitive disease.

In an embodiment of the present invention, any one of the above-noted embodiments, wherein the method specifically includes improving a symptom associated with a cognitive disease.

In an embodiment of the present invention, any one of the above-noted embodiments, wherein the method specifically includes preventing progression of a cognitive disease.

In an embodiment of the present invention, any one of the above-noted embodiments, wherein the patient has been diagnosed as having a cognitive disease.

In an embodiment of the present invention, any one of the above-noted embodiments, wherein the patient has been diagnosed as having Alzheimer's disease.

In an embodiment of the present invention, any one of the above-noted embodiments, wherein the method specifically includes treating a symptom associated with Alzheimer's disease.

In an embodiment of the present invention, any one of the above-noted embodiments, wherein the method specifically includes improving a symptom associated with Alzheimer's disease.

In an embodiment of the present invention, any one of the above-noted embodiments, wherein the method specifically includes preventing progression of Alzheimer's disease.

In an embodiment of the present invention, any one of the above-noted embodiments, wherein the method specifically includes disease modification of Alzheimer's disease.

In an embodiment of the present invention, any one of the above-noted embodiments, wherein the patient has been diagnosed as having mild-to-moderate Alzheimer's disease.

In an embodiment of the present invention, any one of the above-noted embodiments, wherein the patient has been diagnosed as having dementia of an Alzheimer's type.

In an embodiment of the present invention, any one of the above-noted embodiments, wherein the method specifically includes treating a symptom associated with schizophrenia.

In an embodiment of the present invention, any one of the above-noted embodiments, wherein the method specifically includes improving a symptom associated with schizophrenia.

In an embodiment of the present invention, any one of the above-noted embodiments, wherein the method specifically includes preventing progression of schizophrenia.

In an embodiment of the present invention, any one of the above-noted embodiments, wherein the patient has been diagnosed as having schizophrenia.

In an embodiment of the present invention, any one of the above-noted embodiments, wherein the method specifically includes treating a symptom associated with positive symptoms of schizophrenia.

In an embodiment of the present invention, any one of the above-noted embodiments, wherein the method specifically includes improving a symptom associated with positive symptoms of schizophrenia.

In an embodiment of the present invention, any one of the above-noted embodiments, wherein the method specifically includes preventing progression of positive symptoms of schizophrenia.

In an embodiment of the present invention, any one of the above-noted embodiments, wherein the method specifically includes the patient has been diagnosed as having positive symptoms of schizophrenia.

In an embodiment of the present invention, any one of the above-noted embodiments, wherein the method specifically includes treating a symptom associated with negative symptoms of schizophrenia.

In an embodiment of the present invention, any one of the above-noted embodiments, wherein the method specifically includes improving a symptom associated with negative symptoms of schizophrenia.

In an embodiment of the present invention, any one of the above-noted embodiments, wherein the method specifically includes preventing progression of negative symptoms of schizophrenia.

In an embodiment of the present invention, any one of the above-noted embodiments, wherein the method specifically includes the patient has been diagnosed as having negative symptoms of schizophrenia.

In an embodiment of the present invention, any one of the above-noted embodiments, wherein the method specifically includes treating a symptom associated with schizophrenia with dementia.

In an embodiment of the present invention, any one of the above-noted embodiments, wherein the method specifically includes improving a symptom associated with schizophrenia with dementia.

In an embodiment of the present invention, any one of the above-noted embodiments, wherein the method specifically includes preventing progression of schizophrenia with dementia.

In an embodiment of the present invention, any one of the above-noted embodiments, wherein the method specifically includes the patient has been diagnosed as having schizophrenia with dementia.

In an embodiment of the present invention, any one of the above-noted embodiments, wherein the method specifically includes treating a symptom associated with major depressive disorder.

In an embodiment of the present invention, any one of the above-noted embodiments, wherein the method specifically includes improving a symptom associated with major depressive disorder.

In an embodiment of the present invention, any one of the above-noted embodiments, wherein the method specifically includes preventing progression of major depressive disorder.

In an embodiment of the present invention, any one of the above-noted embodiments, wherein the method specifically includes the patient has been diagnosed as having major depressive disorder.

In an embodiment of the present invention, any one of the above-noted embodiments, wherein the method specifically includes the patient has been diagnosed as having a disease associated with chronic inflammation, including atherosclerosis, rheumatoid arthritis and inflammatory bowel diseases.

In an embodiment of the present invention, any one of the above-noted embodiments, wherein the pharmaceutical composition is in the form of a tablet.

Pharmaceutical Compositions

In certain embodiments, the invention also includes pharmaceutical preparations which, besides inert, nontoxic, pharmaceutically suitable excipients, adjuvants and carriers, contain one or more geminal substituted aminobenzisoxazole compounds represented by Formula (Ia) or (Ib), Formula (IIa) or (IIb), or Formula (IIIa) or (IIIb), or a pharmaceutically acceptable salt thereof, or consist of one or more geminal substituted aminobenzisoxazole compounds represented by Formula (Ia) or (Ib), Formula (IIa) or (IIb), or Formula (IIIa) or (IIIb), or a pharmaceutically acceptable salt thereof, and processes for producing these preparations.

A geminal substituted aminobenzisoxazole compound represented by Formula (Ia) or (Ib), Formula (IIa) or (IIb), or Formula (IIIa) or (IIIb), or a pharmaceutically acceptable salt thereof, may be formulated for administration in solid or liquid form. For example, a geminal substituted aminobenzisoxazole compound represented by Formula (Ia) or (Ib), Formula (IIa) or (IIb), or Formula (IIIa) or (IIIb), or a pharmaceutically acceptable salt thereof, may be formulated for administration in a capsule, a tablet, or a powder form. For example, a geminal substituted aminobenzisoxazole compound represented by Formula (Ia) or (Ib), Formula (IIa) or (IIb), or Formula (IIIa) or (IIIb), or a pharmaceutically acceptable salt thereof, may be formulated alone or as part of a pharmaceutical composition, suitable for oral administration, such as in a capsule or tablet, intravenous administration, parenteral administration, topical administration, or transdermal administration, such as in a patch, to a patient in need thereof.

A geminal substituted aminobenzisoxazole compound represented by Formula (Ia) or (Ib), Formula (IIa) or (IIb), or Formula (IIIa) or (IIIb), or a pharmaceutically acceptable salt thereof, may be administered as a pharmaceutical composition, for example, in the presence of carriers, adjuvants, excipients, diluents, fillers, buffers, stabilizers, preservatives, lubricants, and the like, for example, administered as a pharmaceutical composition (e.g., formulation) comprising at least a geminal substituted aminobenzisoxazole compound represented by Formula (Ia) or (Ib), Formula (IIa) or (IIb), or Formula (IIIa) or (IIIb), or a pharmaceutically acceptable salt thereof, together with one or more pharmaceutically acceptable carriers, adjuvants, excipients, diluents, or other materials well known to those skilled in the art. As used herein, the term "pharmaceutically acceptable", unless otherwise specified, includes the generally accepted meaning which encompasses combinations, compounds, materials, compositions, and/or dosage forms which are, within the scope of sound medical judgment, suitable for consumption by humans without excessive toxicity, irritation, allergic response, or other problem or complication, commensurate with a reasonable benefit/risk ratio.

Suitable pharmaceutically acceptable carriers, adjuvants, excipients, and diluents, can include, but are not limited to, lactose, dextrose, sucrose, sorbitol, mannitol, starches, gum, acacia, calcium phosphate, alginates, tragacanth, gelatin, calcium silicate, microcrystalline cellulose, polyvinylpyrrolidone, cellulose, water syrup, methyl cellulose, methyl and propyl hydroxybenzoates, talc, magnesium stearate, and mineral oil. Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The formulations can additionally include, but are not limited to, pharmaceutically acceptable lubricating agents, glidants, wetting agents, emulsifying and suspending agents, preserving agents, sweetening agents, and/or flavoring agents. The pharmaceutical compositions of the present invention may be formulated so as to provide quick release, immediate release, sustained release, or delayed release of a geminal substituted aminobenzisoxazole compound represented by Formula (Ia) or (Ib), Formula (IIa) or (IIb), or Formula (IIIa) or (IIIb), or a pharmaceutically acceptable salt thereof, after administration to the patient by employing procedures well-known in the art.

Another embodiment of the invention further comprises methods of making Pharmaceutical Composition, comprising admixing at least a geminal substituted aminobenzisoxazole compound represented by Formula (Ia) or (Ib), Formula (IIa) or (IIb), or Formula (IIIa) or (IIIb), or a pharmaceutically acceptable salt thereof, together with one or more pharmaceutically acceptable carriers, excipients, buffers, adjuvants, stabilizers, or other materials.

In certain embodiments, the geminal substituted aminobenzisoxazole compounds represented by Formula (Ia) or (Ib), Formula (IIa) or (IIb), or Formula (IIIa) or (IIIb), or a pharmaceutically acceptable salt thereof, are to be present in these preparations in a concentration of from 0.1 to 99.5% by weight, preferably from 0.5 to 95% by weight, of the complete mixture. Besides the geminal substituted aminobenzisoxazole compounds represented by Formula (Ia) or (Ib), Formula (IIa) or (IIb), or Formula (IIIa) or (IIIb), or a pharmaceutically acceptable salt thereof, the pharmaceutical preparations may also contain other active pharmaceutical ingredients.

In certain embodiments, the novel active ingredients can be converted in a known manner into conventional formulations such as tablets, coated tablets, pills, granules, aerosols, syrups, emulsions, suspensions and solutions, using inert, nontoxic, pharmaceutically suitable excipients or solvents. In these cases, the therapeutically active compound should in each case be present in a concentration of about 0.5 to 90% by weight of the entire mixture, i.e., in amounts which are sufficient to reach the stated dose range.

In certain embodiments, the formulations are produced, for example, by extending the active ingredients with solvents and/or excipients, where appropriate with use of emulsifiers and/or dispersants, it being possible for example when water is used as diluent where appropriate to use organic solvents as auxiliary solvents.

In certain embodiments, administration may take place in a conventional way, for example, orally, transdermally or parenterally, especially perlingually or intravenously. In certain embodiments, administration may also take place by inhalation through the mouth or nose, for example, with the aid of a spray, or topically via the skin.

In certain embodiments, the geminal substituted aminobenzisoxazole compounds represented by Formula (Ia) or (Ib), Formula (IIa) or (IIb), or Formula (IIIa) or (IIIb), or a pharmaceutically acceptable salt thereof, may be administered in amounts of about 0.01 to 10 mg/kg, on oral administration, for example, about 0.05 to 5 mg/kg, of body weight to achieve effective results.

EXAMPLES

Analytical Instrument Model:

TABLE 1

| | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| | Agilent Technologies 1100 |
| | Agilent Technologies 1260 |
| NMR | BRUKER ADVANCE III/400 (400 MHz) |
| | BRUKER ADVANCE 400 (400 MHz) |
| | BRUKER DMX300 (300 MHz) |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

LCMS:

LCMS Conditions A ("LCMS (A)"): Instrument: Shimadzu LCMS 2020; Mobile phase A: 4 L H2O†1.5 mL TFA, Mobile phase B: 4 L ACN†0.75 mL TFA; Method name: 10-80AB_4MIN_2W; Flow Rate: 0.8 mL/min.; Gradient: 10%-80%; Column: Boston Green ODS 2.1×30 mm, 3 μm; Column temperature: 50° C.; Wavelength: 220 nm & 254 nm.

LCMS Conditions B ("LCMS (B)"): Instrument: Agilent 1200 Series; Mobile phase A: 4 L H2O†1.5 ml TFA, Mobile phase B: 4 L ACN†0.75 mL TFA; Method name: 5-95AB_R_2W; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions C ("LCMS (C)"): Instrument: Agilent 1200 Series; Mobile phase A: 4 L H2O†2 mL NH3H2O; Mobile phase B: Acetonitrile; Method name: 5-95CD_4.5MIN_2W; Flow Rate: 0.8 mL/min.; Gradient: 5%-95%; Column: Chromolith@Flash RP-18e 25×2 mm; Column temperature 50° C.; Wavelength: 220 nm & 254 nm.

LCMS Conditions D ("LCMS (D)"): Instrument: Agilent 1200 Series; Mobile phase A: 4 L H2O†1.5 mL TFA, Mobile phase B: 4 L ACN†0.75 mL TFA; Method name: 5-95AB_R_4MIN2W; Flow Rate: 0.8 mL/min.; Gradient: 5%-95%; Column: Chromolith@Flash RP-18e 25×2 mm; Column temperature: 50° C.; Wavelength: 220 nm & 254 nm.

LCMS Conditions E ("LCMS (E)"): Instrument: Agilent 1200 Series; Mobile phase A: 4 L H2O†1.5 ml TFA, Mobile phase B: 4 L ACN†0.75 mL TFA; Method name: 5-95AB_R; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions F ("LCMS (F)"): Instrument: Agilent 1200 Series; Mobile phase A: 4 L H2O†2 ml NH3H2O, Mobile phase B: Acetonitrile; Method name: 5-95CD_2MIN_2W; Flow Rate: 1.2 mL/min.; Gradient: 5%-95%; Column: XBridge Shield RP-18 2.1×50 mm, 5 μm; Column temperature: 30° C.; Wavelength: 220 nm & 254 nm.

LCMS Conditions G ("LCMS (G)"): Instrument: Agilent 1200 Series; Mobile phase A: 4 L H2O†2 mL NH3H2O, Mobile phase B: Acetonitrile; Method name: 10-80CD_4MIN_2W; Flow Rate: 0.8 mL/min.; Gradient: 10%-80%; Column: XBridge C-18 2.1×50 mm, 5 μm; Column temperature: 40° C.; Wavelength: 220 nm & 254 nm.

LCMS Conditions H ("LCMS (H)"): Instrument: Agilent 1200 Series; Mobile phase A: 4 L H2O†1.5 mL TFA, Mobile phase B: 4 L ACN†0.75 mL TFA; Method name: 10-80AB_4MIN_2W; Flow Rate: 0.8 mL/min.; Gradient: 10%-80%; Column: Xtimate C-18, 2.1×30 mm, 3 μm; Column temperature: 50° C.; Wavelength: 220 nm & 254 nm.

LCMS Conditions I ("LCMS (I)"): Instrument: Agilent 1200 Series; Mobile phase A: 4 L H2O†2 mL NH3H2O, Mobile phase B:Acetonitrile; Method name: 0-60CD_4.5MIN_2W; Flow Rate: 0.8 ml/min.; Gradient: 0%-60%; Column: XBrige Shield RP-18 2.1×50 mm, 5 μm; Column temperature 50° C.; Wavelength: 220 nm & 254 nm.

LCMS Conditions J ("LCMS (J)"): Instrument: Agilent 1200 Series; Mobile phase A: 4 L H2O†2 mL NH3H2O, Mobile phase B: Acetonitrile; Method name: 10-80CD_2MIN_POS_2W; Flow Rate: 1.2 ml/min.; Gradient: 10%-80%; Column: Xbridge C-18 2.1×50 mm, 5 μm; Column temperature: 40° C.; Wavelength: 220 nm & 254 nm.

LCMS Conditions K ("LCMS (K)"): Instrument: Shimadzu LCMS 2020; Mobile phase A: 4 L H2O†1.5 mL TFA, Mobile phase B: 4 L ACN†0.75 mL TFA; Method name: 0-30AB_2MIN_2W; Flow Rate: 1.2 mL/min.; Gradient: 0%-30%; Column: Chromolith@Flash RP-18E 25×2 mm; Column temperature: 50° C.; Wavelength: 220 nm & 254 nm.

LCMS Conditions L ("LCMS (L)"): Instrument: Shimadzu LCMS 2020; Mobile phase A: 4 L H2O†1.5 mL TFA, Mobile phase B: 4 L ACN†0.75 mL TFA; Method name: 0-30AB_4MIN_2W; Flow Rate: 0.8 mL/min.; Gradient: 0%-30%; Column: Chromolith@Flash RP-18E 25×2 mm; Column temperature: 50° C.; Wavelength: 220 nm & 254 nm.

LCMS Conditions M ("LCMS (M)"): Instrument: Shimadzu LCMS 2020; Mobile phase A: 4 L H2O†1.5 mL TFA, Mobile phase B: 4 L ACN†0.75 mL TFA; Method name: 0-60AB_2MIN_2W; Flow Rate: 1.2 mL/min.; Gradient: 0%-60%; Column: Chromolith@Flash RP-18E 25×2 mm; Column temperature: 50° C.; Wavelength: 220 nm & 254 nm.

LCMS Conditions N ("LCMS (N)"): Instrument: Shimadzu LCMS 2020; Mobile phase A: 4 L H2O†1.5 mL TFA, Mobile phase B: 4 L ACN†0.75 mL TFA; Method name: 0-60AB_4MIN_2W; Flow Rate: 0.8 mL/min.; Gradient: 0%-60%; Column: Chromolith@Flash RP-18E 25×2 mm; Column temperature: 50° C.; Wavelength: 220 nm & 254 nm.

LCMS Conditions O ("LCMS (O)"): Instrument: Agilent 1200 Series LCMS; Mobile phase A: 4 L H2O†2 mL NH3H2O, Mobile phase B: CAN; Method name: 0-30CD_2MIN_POS_2W; Flow Rate: 1.0 mL/min.; Gradient: 0%-30%; Column: Xbridge C18 2.1×50 mm, 5 um; Column temperature: 40° C.; Wavelength: 220 nm & 254 nm.

LCMS Conditions P ("LCMS (P)"): Instrument: Agilent 1200 Series LCMS; Mobile phase A: 4 L H2O†2 mL NH3H2O, Mobile phase B: CAN; Method name: 0-60CD_2MIN_POS_2W; Flow Rate: 1.0 mL/min.; Gradient: 0%-60%; Column: Xbridge C18 2.1×50 mm, 5 um; Column temperature: 40° C.; Wavelength: 220 nm & 254 nm.

LCMS Conditions Q ("LCMS (Q)"): Instrument: Agilent 1200 Series LCMS; Mobile phase A: 4 L H2O†2 mL NH3H2O, Mobile phase B: CAN; Method name: 0-60CD_4MIN_2W; Flow Rate: 0.8 mL/min.; Gradient:

0%-60%; Column: Xbridge C18 2.1×50 mm, 5 um; Column temperature: 40° C.; Wavelength: 220 nm & 254 nm.

LCMS Conditions R ("LCMS (R)"): Instrument: Agilent 1200 Series LCMS; Mobile phase A: 4 L H2O†1.5 mL TFA, Mobile phase B: 4 L ACN†0.75 mL TFA; Method name: 10-80AB_2MIN_2W; Flow Rate: 1.2 mL/min.; Gradient: 10%-80%; Column: Xtimate C18, 2.1×30 mm, 3 um; Column temperature: 50° C.; Wavelength: 220 nm & 254 nm.

LCMS Conditions S ("LCMS (S)"): Instrument: Agilent 1200 Series LCMS; Mobile phase A: 4 L H2O†2 mL NH3H2O, Mobile phase B: CAN; Method name: 30-90CD_4MIN_POS2W; Flow Rate: 0.8 mL/min.; Gradient: 30%-90%; Column: Xbridge C18 2.1×50 mm, 5 um; Column temperature: 40° C.; Wavelength: 220 nm & 254 nm.

LCMS Conditions T ("LCMS (T)"): Instrument: Agilent 1200 Series LCMS; Mobile phase A: 4 L H2O†1.5 mL TFA, Mobile phase B: 4 L ACN†0.75 mL TFA; Method name: 5-95AB_15MIN_YMC; Flow Rate: 1.0 mL/min.; Gradient: 5%-95%; Column: YMC-Pack ODS-A 5 μm 150×4.6 mm; Column temperature: 50° C.; Wavelength: 220 nm & 254 nm.

LCMS Conditions U ("LCMS (U)"): Instrument: Agilent 1200 Series LCMS; Mobile phase A: 4 L H2O†1.5 mL TFA, Mobile phase B: 4 L ACN†0.75 mL TFA; Method name: 0-30AB_2MIN_2W; Flow Rate: 1.2 mL/min.; Gradient: 0%-30%; Column: Chromolith@Flash RP-18E 25×2 mm; Column temperature: 50° C.; Wavelength: 220 nm & 254 nm.

LCMS Conditions V ("LCMS (V)"): Instrument: Agilent 1200 Series LCMS; Mobile phase A: 4 L H2O†1.5 mL TFA, Mobile phase B: 4 L ACN†0.75 mL TFA; Method name: 0-30AB_4MIN_2W; Flow Rate: 0.8 mL/min.; Gradient: 0%-30%; Column: Chromolith@Flash RP-18E 25×2 mm; Column temperature: 50° C.; Wavelength: 220 nm & 254 nm.

LCMS Conditions W ("LCMS (W)"): Instrument: Agilent 1200 Series LCMS; Mobile phase A: 4 L H2O†1.5 mL TFA, Mobile phase B: 4 L ACN†0.75 mL TFA; Method name: 0-60AB_2MIN_2W; Flow Rate: 1.2 mL/min.; Gradient: 0%-60%; Column: Chromolith@Flash RP-18E 25×2 mm; Column temperature: 50° C.; Wavelength: 220 nm & 254 nm.

LCMS Conditions X ("LCMS (X)"): Instrument: Agilent 1200 Series LCMS; Mobile phase A: 4 L H2O†1.5 mL TFA, Mobile phase B: 4 L ACN†0.75 mL TFA; Method name: 0-60AB_4MIN_2W; Flow Rate: 0.8 mL/min.; Gradient: 0%-60%; Column: Chromolith@Flash RP-18E 25×2 mm; Column temperature: 50° C.; Wavelength: 220 nm & 254 nm.

LCMS Conditions Y ("LCMS (Y)"): Instrument: Shimadzu LCMS 2020; Mobile phase A: 4 L H2O†1.5 ml TFA, Mobile phase B: 4 L ACN†0.75 mL TFA; Method name: 5-95AB_R_2W; Flow Rate: 1.5 mL/min.; Gradient: 5%-95%; Column: Chromolith@Flash RP-18e 25×2 mm; Column temperature: 50° C.; Wavelength: 220 nm & 254 nm.

LCMS Conditions Z ("LCMS (Z)"): Instrument: Shimadzu LCMS 2020; Mobile phase A: 4 L H2O†1.5 mL TFA, Mobile phase B: 4 L ACN†0.75 mL TFA; Method name: 5-95AB_R_4MIN2W; Flow Rate: 0.8 mL/min.; Gradient: 5%-95%; Column: Chromolith@Flash RP-18e 25×2 mm; Column temperature: 50° C.; Wavelength: 220 nm & 254 nm.

LCMS Conditions AA ("LCMS (AA)"): Instrument: Agilent 1200 Series LCMS; Mobile phase A: 4 L H2O†2 mL NH3H$_2$O, Mobile phase B: ACN; Method name: 10-80CD_2MIN_NEG; Flow Rate: 1.2 mL/min.; Gradient: 10%-80%; Column: Xbridge C18 2.1×50 mm, 5 m; Column temperature: 40° C.; Wavelength: 220 nm & 254 nm.

LCMS Conditions BB ("LCMS (BB)"): Instrument: Agilent 1200 Series LCMS; Mobile phase A: 4 L H2O†1.5 mL TFA, Mobile phase B: 4 L ACN†0.75 mL TFA; Method name: 0-60AB_R_2W; Flow Rate: 1.5 mL/min.; Gradient: 0%-60%; Column: Chromolith@Flash RP-18E 25×2 mm; Column temperature: 50° C.; Wavelength: 220 nm & 254 nm.

LCMS Conditions CC ("LCMS (CC)"): Instrument: Agilent 1200 Series LCMS; Mobile phase A: 4 L H2O†1.5 mL TFA, Mobile phase B: 4 L ACN†0.75 mL TFA; Method name: 0-30AB_R_2W; Flow Rate: 1.5 mL/min.; Gradient: 0%-30%; Column: Chromolith@Flash RP-18E 25×2 mm; Column temperature: 50° C.; Wavelength: 220 nm & 254 nm.

LCMS Conditions DD ("LCMS (DD)"): Instrument: Agilent 1200 Series LCMS; Mobile phase A: 4 L H2O†1.5 mL TFA, Mobile phase B: 4 L ACN†0.75 mL TFA; Method name: 10-80AB_R_2W; Flow Rate: 1.5 mL/min.; Gradient: 10%-80%; Column: Chromolith@Flash RP-18E 25×2 mm; Column temperature: 50° C.; Wavelength: 220 nm & 254 nm.

LCMS Conditions EE ("LCMS (EE)"): Instrument: Agilent 1200 Series; Mobile phase A: 1 L H2O†0.375 mL TFA, Mobile phase B: 4 L ACN†0.75 mL TFA; Method name: WUXIAB00; Flow Rate: 0.6-1.0 mL/min; Gradient: 0%-80%-100%; Column: Agilent 5 TC-C18 50×2.1 mm; Column temperature: 50° C.; Wavelength: 220 nm & 254 nm.

LCMS Conditions FF ("LCMS (FF)"): Instrument: Agilent 1200 Series; Mobile phase A: 1 L H2O†0.375 mL TFA, Mobile phase B: 4 L ACN†0.75 mL TFA; Method name: WUXIAB01; Flow Rate: 0.8-1.0 mL/min; Gradient: 1%-90%-100%; Column: Agilent 5 TC-C18 50×2.1 mm; Column temperature: 50° C.; Wavelength: 220 nm & 254 nm.

LCMS Conditions GG ("LCMS (GG)"): Instrument: Agilent 1200 Series; Mobile phase A: 1 L H2O†0.375 mL TFA, Mobile phase B: 4 L ACN†0.75 mL TFA; Method name: WUXIAB10; Flow Rate: 0.8-1.0 mL/min; Gradient: 10%-100%; Column: Agilent 5 TC-C18 50×2.1 mm; Column temperature: 50° C.; Wavelength: 220 nm & 254 nm.

LCMS Conditions 1 ("LCMS (1)"): Instrument: Agilent 1100 Bin. Pump: G1312A, degasser; autosampler, ColCom, DAD: Agilent G1315B, 210 nm, MSD: Agilent LC/MSD G1956B ESI, pos/neg 100-800; MS parameters: Source: ESI, Capillary voltage: 3000V, Drying gas flow: 12 L/min., Nebulizer Pressure 60 psig, Drying Gas Temperature: 350° C., Fragmentor 70, MS scan: MS range 100-800 (positive and negative mode), Flow into MS 0.4 mL/min.; Mobile phase A: 95% acetonitrile+5% 10 mM ammonium bicarbonate in water; Mobile phase B: 10 mM ammonium bicarbonate in water pH=9.0; Flow Rate: 0.8 mL/min; Linear Gradient: t=0 min 5% A, t=3.5 min 98% A, t=6 min 98% A; Column: Phenomenex Gemini NX (C18, 50×2.0 mm, particle size: 3 μm); Column temperature: 25° C.; Detection DAD: Wavelength 220-320 nm.

LCMS Conditions 2 ("LCMS (2)"): Instrument Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-800, ELSD Alltech 3300 gas flow 1.5 mL/min., Gas Temperature: 40° C.; MS parameters: Source: ESI, Capillary voltage: 3000V, Drying gas flow: 12 L/min., Nebulizer Pressure 60 psig, Drying Gas Temperature: 350° C., Fragmentor 70, MS scan:

MS range 100-800 (positive and negative mode), Flow into MS 0.4 mL/min.; Mobile phase A: 0.1% formic acid in acetonitrile; Mobile phase B: 0.1% formic acid in water; Flow Rate: 1 mL/min; Linear gradient: t=0 min 5% A, t=1.6 min 98% A, t=3 min 98% A; Column: Waters XSelect (C18, 30×2.1 mm, particle size 3.5 µm); Column temperature: 35° C.; Detection DAD: Wavelength 220-320 nm.

LCMS (3): Instrument Apparatus: Agilent 1260 Bin. Pump: G1312B, degasser; autosampler, ColCom, DAD: Agilent G1315D, 220-320 nm, MSD: Agilent LC/MSD G6130B ESI, pos/neg 100-800, ELSD Alltech 3300 gas flow 1.5 mL/min., Gas Temperature: 40° C.; MS parameters: Source: ESI, Capillary voltage: 3000V, Drying gas flow: 12 L/min., Nebulizer Pressure 60 psig, Drying Gas Temperature: 350° C., Fragmentor 70, MS scan: MS range 100-800 (positive and negative mode), Flow into MS 0.4 mL/min.; Mobile phase A: 0.1% formic acid in acetonitrile; Mobile phase B: 0.1% formic acid in water; Flow: 0.8 mL/min; Linear Gradient: t=0 min 5% A, t=3.5 min 98% A, t=6 min 98% A; Water XSelect (C18, 50×2.1 mm, particle size: 3.5 µm); Column temperature: 35° C.; Detection: DAD: Wavelength 220-320 nm.

Preparative HPLC (1): MS instrument type: Agilent Technologies G1956B Quadrupole LC-MS; HPLC instrument type: Agilent Technologies 1200 preparative LC; column: Phenomenex Gemini-NX(C18, 100×21.2 mm, 10µ); flow: 25 ml/min; column temp: RT; eluent A: 99% acetonitrile+ 1% 10 mM ammonium bicarbonate in water pH=9.0, eluent B: 10 mM ammonium bicarbonate in water pH=9.0; detection: DAD (220-320 nm); detection: MSD (ESI pos/neg) mass range: 100-800; fraction collection based on MS and DAD.

GCMS:

GCMS Conditions Instrument: SHIMADZU GCMS-QP2010 Ultra; Carrier gas: He; Column Flow: 1.5 mL/min; Injector: 250° C.; Split Ratio: 100:1; Column: HP-5MS 15 m×0.25 mm×0.25 um; FILM From: 40° C. (holding 3 min) to 250° C. (holding 3 min) at the rate of 25° C./min.

cSFC Analytical:

cSFC Analytical Conditions: Flow rate: 3 mL/min; Wavelength: 220 nm; and Column temperature: 35° C., were used for each of the specified conditions below:

cSFC Analytical Conditions A ("cSFC analytical (A)"): Column: Chiralpak OD-3 100×4.6 mm I.D., 3 um; Mobile phase: ethanol (0.05% diethylamine ("DEA") in $CO_2$ from 5% to 40%.

cSFC Analytical Conditions B ("cSFC analytical (B)"): Column: Chiralpak OD-3 100×4.6 mm I.D., 3 um; Mobile phase: methanol (0.05% DEA) in $CO_2$ from 5% to 40%.

cSFC Analytical Conditions C ("cSFC analytical (C)"): Column: Chiralpak OD-3 100×4.6 mm I.D., 3 um; Mobile phase: 40% ethanol (0.05% DEA) in $CO_2$.

cSFC Analytical Conditions D ("cSFC analytical (D)"): Column: Chiralpak AY-3 100×4.6 mm I.D., 3 um; Mobile phase: ethanol (0.05% DEA) in $CO_2$ from 5% to 40%.

cSFC Analytical Conditions E ("cSFC analytical (E)"): Column: Chiralpak OJ-3 100×4.6 mm I.D., 3 um; Mobile phase: ethanol (0.05% DEA) in $CO_2$ from 5% to 40%.

cSFC Analytical Conditions F ("cSFC analytical (F)"): Column: Chiralpak OJ-3 100×4.6 mm I.D., 3 um; Mobile phase: methanol (0.05% DEA) in $CO_2$ from 5% to 40%.

cSFC Analytical Conditions G ("cSFC analytical (G)"): Column: Chiralpak AD-3 100×4.6 mm I.D., 3 um; Mobile phase: ethanol (0.05% DEA) in $CO_2$ from 5% to 40%.

cSFC Analytical Conditions H ("cSFC analytical (H)"): Column: Chiralpak AD-3 100×4.6 mm I.D., 3 um; Mobile phase: methanol (0.05% DEA) in $CO_2$ from 5% to 40%.

For each final compound prepared below that indicates the presence of a salt associated with the final compound (i.e., a salt complex), the specific molar equivalence of salt included in the final compound, unless specified, was not determined.

Example 1A: quinuclidin (N-borane)-3-one (A-1)

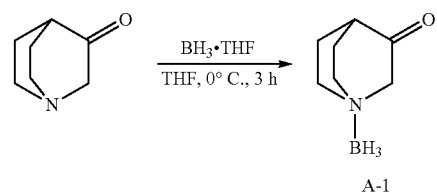

To a mixture of quinuclidin-3-one (0.20 kg, 1.6 mol) in tetrahydrofuran (1 L) at 0° C. was added dropwise 1 M borane in tetrahydrofuran (1.8 L, 1.8 mol). The mixture was stirred at 0° C. for 3 hours. On completion, the solution was quenched by methanol, evaporated and purified by silica gel chromatography (petroleum ether: ethyl acetate=10:1) to give compound A-1 (0.19 kg, 86% yield) as a white solid.

Example 2A: 2,2-dimethylquinuclidin (N-borane)-3-one (A-2)

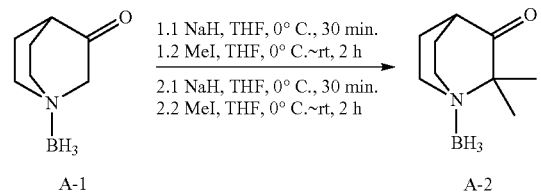

To a mixture of compound A-1 (20 g, 0.14 mol) in tetrahydrofuran (200 mL) at 0° C. was added sodium hydride (8.6 g, 60%, 0.22 mol) in portions. The reaction was stirred for 30 minutes. Iodomethane (31 g, 0.22 mol) in tetrahydrofuran (30 mL) was added dropwise to the mixture at 0° C., and the reaction was stirred at room temperature for 2 hours, and then cooled to 0° C. Sodium hydride (8.6 g, 60%, 0.22 mol) was added in portions, and stirring was continued for 30 minutes. Iodomethane (31 g, 0.22 mol) in tetrahydrofuran (30 mL) was again added dropwise to the mixture at 0° C., and the reaction was stirred at room temperature for another 2 hours. On completion, the reaction was quenched with saturated ammonium chloride aqueous solution and concentrated in vacuo. The residue was purified by silica gel chromatography (petroleum ether: ethyl acetate=10:1) to give compound A-2 (14 g, 58% yield) as a white solid.

Example 3A: 2,2-dimethylquinuclidin-3-one oxime (A-3)

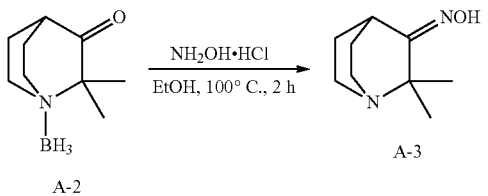

To a mixture of compound A-2 (0.50 g, 3.0 mmol) in anhydrous ethanol (2 mL) was added hydroxylamine hydrochloride (0.21 g, 3.0 mmol) at room temperature. The mixture was stirred at 100° C. for 2 hours. On completion, the solution was cooled to room temperature, resulting in formation of a precipitate. The precipitation was collected by filtration to give compound A-3 (0.48 g, 96% yield) as a white solid. LCMS (K): tR=1.093 min., (ES$^+$) m/z (M+H)$^+$= 169.1.

Example 4A: (+/−)-2,2-dimethylquinuclidin-3-amine (rac-A-4)

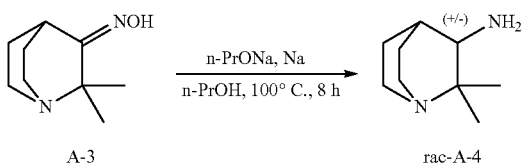

To a mixture of compound A-3 (0.60 g, 2.9 mmol) in n-propyl alcohol (6 mL) was added sodium n-propoxide (67 mg, 2.9 mmol sodium in 1 mL n-propyl alcohol) at room temperature. The solution was heated to 100° C., and sodium (0.67 g, 29 mmol) was added in portions. The mixture was stirred at this temperature for 8 hours. On completion, the mixture was poured into water (1 mL), concentrated in vacuo, diluted with dichloromethane and filtered. The resulting filtrate was concentrated in vacuo to give rac-A-4 (0.40 g, 89% yield) as a yellow oil. LCMS (K): tR=0.988 min., (ES$^+$) m/z (M+H)$^+$=155.1.

Example 5A: 2,2-dimethylquinuclidin-3-one (A-5)

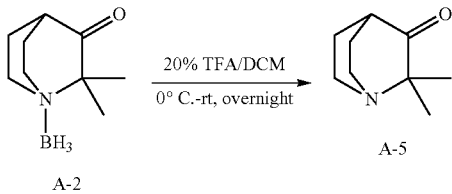

To a solution of 20% trifluoroacetic acid/dichloromethane (150 mL, v/v) at 0° C. was added portionwise compound A-2 (45 g, 0.27 mol). The mixture was stirred at room temperature overnight. On completion, the pH was adjusted to 8 by addition of saturated aqueous potassium carbonate solution at 0° C. The mixture was extracted with dichloromethane (2×200 mL). The combined organic layers were dried with sodium sulfate and concentrated in vacuo to give compound A-5 (40 g, 98% yield) as a white solid. $^1$H-NMR (CD$_3$OD, 400 MHz): 3.37-3.36 (m, 2H), 2.98-2.97 (m, 2H), 2.39-2.38 (m, 1H), 2.10-2.09 (m, 4H), 1.34 (s, 6H).

Example 6A: (R)—N-(2,2-dimethylquinuclidin-3-ylidene)-1-phenylethanamine ((R)-A-6)

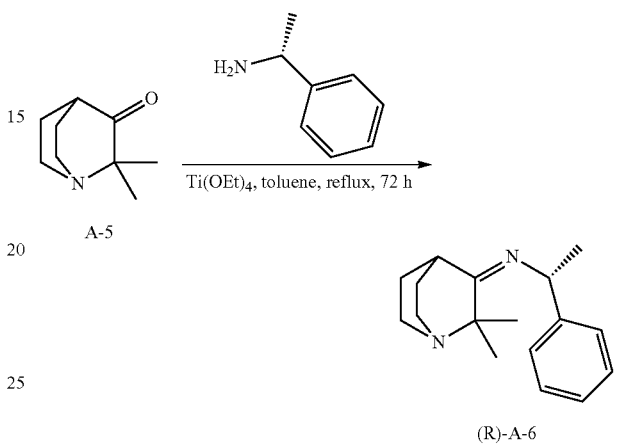

To a solution of compound A-5 (7.2 g, 47 mmol) and (R)-1-phenylethanamine (6.8 g, 56 mmol) in toluene (140 ml) was added titanium tetraethoxide (32 g, 0.14 mol), and the mixture was heated at reflux for 72 hours. On completion, the mixture was cooled to room temperature and poured into saturated aqueous potassium carbonate solution (500 mL). Ethyl acetate (500 mL) was added, and the mixture was stirred vigorously for 10 minutes and filtered over celite. The layers were separated, and the water layer was extracted with ethyl acetate (3×500 mL). The combined organic layers were dried with sodium sulfate and concentrated in vacuo to give compound (R)-A-6 (13 g, crude, 52% purity by LCMS) as a yellow oil. The material was used for the next step without further purification. LCMS (J): tR=1.337, (ES$^+$) m/z (M+H)$^+$=257.1.

Example 7A: (R)-2,2-dimethyl-N—((R)-1-phenylethyl)quinuclidin-3-amine ((R,R)-A-7)

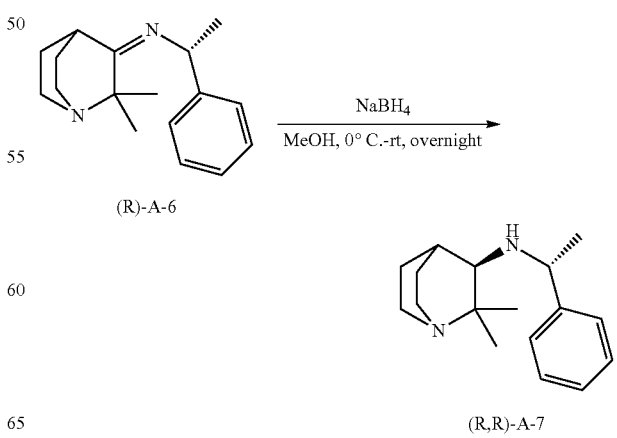

To a solution of compound (R)-A-6 (13 g, 26 mmol, 52% purity) in methanol (130 mL) at 0° C. was added sodium borohydride (5.0 g, 0.13 mol). The mixture was stirred for 30 minutes at 0° C., then allowed to warm to room temperature and stirred overnight. On completion, the reaction was poured into saturated aqueous potassium carbonate (500 mL), and the mixture was extracted with ethyl acetate (2×500 mL). The combined organic layers were dried over sodium sulfate and concentrated in vacuo to give 11 g of a clear oil. The crude product was purified by silica gel chromatography (petroleum ether: ethyl acetate=5:1) to give compound (R,R)-A-7 (7.3 g, 58% yield for two steps) as a clear oil. $^1$H-NMR (CD$_3$OD, 400 MHz): δ 7.34-7.26 (m, 4H), 7.22-7.18 (m, 1H), 3.78-3.73 (m, 1H), 3.35-3.18 (m, 1H), 3.06-3.01 (m, 1H), 2.61-2.53 (m, 2H), 2.32 (s, 1H), 1.81-1.78 (m, 1H), 1.63-1.54 (m, 2H), 1.44-1.42 (m, 1H), 1.41 (s, 3H), 1.31 (d, J=6.8 Hz, 3H), 1.30-1.26 (m, 1H), 1.21 (s, 3H).

Example 8A: (R)-2,2-dimethylquinuclidin-3-amine ((R)-A-4)

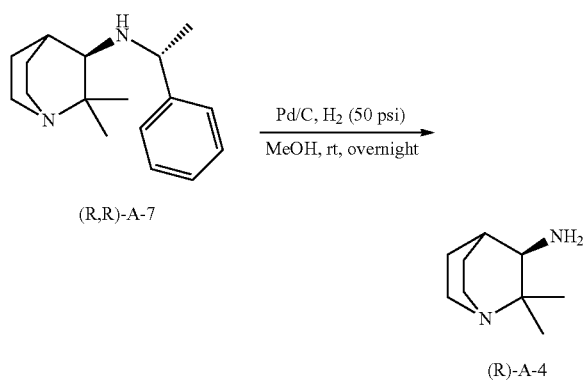

To a solution of compound (R,R)-A-7 (5.3 g, 21 mmol) in methanol (100 mL) was added 10% palladium/carbon, 50% wet (1.5 g) under nitrogen. The suspension was degassed in vacuo and purged with hydrogen several times. The resulting mixture was stirred at room temperature overnight under hydrogen (50 psi). On completion, the reaction mixture was filtered, and the filtrate was concentrated in vacuo to give freebase compound (R)-A-4 (3.0 g, 93% yield) as a white semi-solid. $^1$H-NMR (CD$_3$OD, 400 MHz): 3.28-3.24 (m, 2H), 2.79-2.73 (m, 3H), 1.92-1.90 (m, 1H), 1.76-1.73 (m, 3H), 1.45-1.44 (m, 1H), 1.31 (s, 3H), 1.29 (s, 3H).

The dihydrochloride salt of compound (R)-A-4 can be also obtained either by adding HCl to accelerate the reaction, or directly from the isolated freebase, to give compound (R)-A-4 dihydrochloride as a white solid. 1H-NMR (CD3OD, 400 MHz): 3.72-3.64 (m, 2H), 3.60 (s, 1H), 3.42-3.33 (m, 2H), 2.40-2.39 (m, 1H), 2.25-2.11 (m, 3H), 2.03-1.97 (m, 1H), 1.71 (s, 3H), 1.69 (s, 3H).

The A ditosylate salt form of compound (R)-A-4 can also be prepared by dissolving compound (R)-A-4 (20 g, 130 mmol) in anhydrous dichloromethane (200 mL), followed by addition of 4-methylbenzenesulfonic acid (49 g, 260 mmol). The mixture was stirred at 25° C. for 12 hours and then concentrated in vacuo. Anhydrous ethanol (40 mL) and anhydrous methanol (4 mL) were added, and the mixture was stirred at 25° C. for 12 hours. The solids were collected by filtration and dried in vacuo to give compound (R)-A-4 ditosylate (45 g, 70% yield) as a white solid. 1H-NMR (CD3OD, 400 MHz): 7.71-7.69 (d, J=8.0 Hz, 4H), 7.26-7.24 (d, J=7.6 Hz, 4H), 3.66-3.58 (m, 3H), 3.39-3.34 (m, 2H), 2.37-2.34 (m, 7H), 2.09 (s, 3H), 1.99-1.93 (m, 1H), 1.64 (s, 3H), 1.60 (s, 3H).

Example 9A: (S)—N-(2,2-dimethylquinuclidin-3-ylidene)-1-phenylethanamine ((S)-A-6)

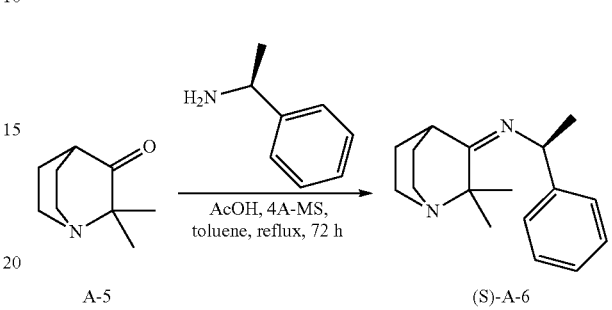

To a solution of compound A-5 (4.1 g, 27 mmol) and (S)-1-phenylethanamine (3.9 g, 32 mmol) in toluene (40 mL) were added acetic acid (1.6 g, 27 mmol) and 4A-molecular sieve (1.0 g). The mixture was heated at reflux for 72 hours. On completion, the mixture was cooled to room temperature and concentrated in vacuo to give compound (S)-A-6 (8.5 g, crude) as a yellow oil. LCMS showed 38% purity. This material was used for the next step directly without further purification. LCMS (J): tR=1.228, (ES$^+$) m/z (M+H)$^+$=257.2.

Example 10A: (S)-2,2-dimethyl-N—((S)-1-phenylethyl)quinuclidin-3-amine ((S,S)-A-7)

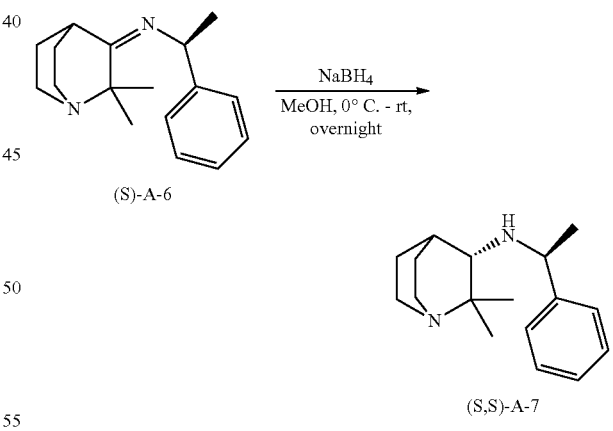

To a solution of compound (S)-A-6 (8.5 g, 13 mmol, 38% purity) in methanol (80 mL) at 0° C. was added sodium borohydride (2.4 g, 63 mmol). The reaction was stirred for 30 minutes at 0° C., then allowed to warm to room temperature and stirred overnight. On completion, the mixture was poured into saturated aqueous potassium carbonate (100 mL) and extracted with ethyl acetate (2×100 mL). The combined organic layers were dried over sodium sulfate and concentrated in vacuo to give 8.0 g of a clear oil. The crude product was purified by silica gel chromatography (petroleum ether: ethyl acetate=5:1) to give compound (S,S)-A-7

(1.8 g, 26% yield for two steps) as a clear oil. ¹H-NMR (CD₃OD, 400 MHz): δ 7.34-7.28 (m, 4H), 7.22-7.19 (m, 1H), 3.78-3.73 (m, 1H), 3.27-3.21 (m, 1H), 3.08-3.04 (m, 1H), 2.65-2.58 (m, 2H), 2.34 (s, 1H), 1.84-1.82 (m, 1H), 1.65-1.56 (m, 2H), 1.45-1.43 (m, 1H), 1.36 (s, 3H), 1.31 (d, J=6.8 Hz, 3H), 1.23 (s, 3H), 1.15-1.14 (m, 1H).

Example 11A: (S)-2,2-dimethylquinuclidin-3-amine ((S)-A-4)

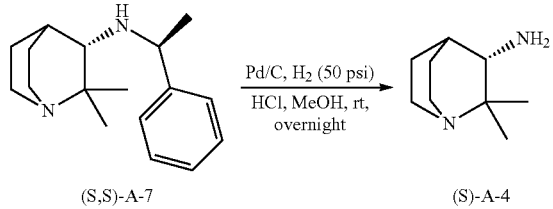

To a solution of compound (S,S)-A-7 (1.8 g, 7.0 mmol) in methanol (40 mL) was added 10% palladium/carbon, 50% wet (0.4 g) under nitrogen. The suspension was degassed in vacuo and purged with hydrogen several times. The resulting mixture was stirred under hydrogen (50 psi) at room temperature overnight. On completion, the reaction mixture was filtered, and the filtrate was concentrated in vacuo to give compound (S)-A-4 (1.0 g, 93% yield) as a white semi-solid. ¹H-NMR (CD₃OD, 400 MHz): 3.44-3.36 (m, 2H), 3.03-2.93 (m, 2H), 2.90 (s, 1H), 2.07-2.02 (m, 1H), 1.92-1.85 (m, 3H), 1.65-1.58 (m, 1H), 1.43 (s, 3H), 1.39 (s, 3H).

Example 12A: 2-methylenequinuclidin-3-one (A-8)

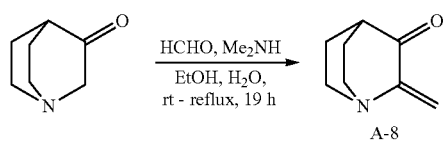

To a mixture of quinuclidin-3-one (30 g, 0.24 mol) in ethanol/water (0.65 L, 2.5:1) was added dimethylamine (49 g, 0.36 mol) in one portion, followed by formaldehyde (28 g, 0.36 mol) in one portion at room temperature. After stirring at room temperature for 10 min, the reaction mixture was heated to reflux for 3 hours, and then stirred at 70° C. for 16 hours. TLC showed the starting material was consumed completely. The reaction mixture was cooled to room temperature and concentrated in vacuo. The residue was purified by distillation to give compound A-8 (14 g, 43% yield) as yellow oil. GCMS: tR=5.629, (EI⁺) m/z (M)=137.2.

Example 13A: 1'-azaspiro[cyclopropane-1,2'-bicyclo [2.2.2]octan]-3'-one (A-9)

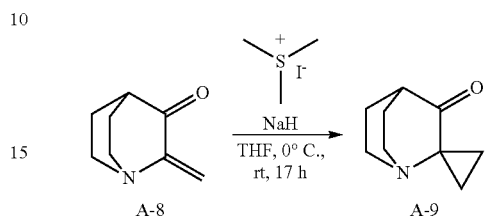

To a solution of trimethylsulfoxonium iodide (42 g, 0.19 mol) in anhydrous tetrahydrofuran (500 mL) at 0° C. was added sodium hydride (7.6 g, 0.19 mol). The reaction mixture was stirred at 0° C. for 1 hour, and compound A-8 (20 g, 0.15 mol) was added dropwise. The mixture was allowed to warm to room temperature and stirred for 16 hours. GCMS showed the reaction was completed. The reaction was quenched with saturated aqueous ammonium chloride solution and filtered. The filtrate was concentrated in vacuo, diluted with dichloromethane (200 mL) and water (200 mL) and extracted with dichloromethane (3×600 mL). The combined organic layers were washed with brine (2×400 mL), dried over anhydrous sodium sulfate, filtered and concentrated in vacuo. The residue was purified by aluminum oxide column chromatography [petroleum ether: ethyl acetate=5:1] to give compound A-9 (4.8 g, 22% yield) as a white solid. GCMS: tR=7.253, (EI⁺) m/z (M+H)⁺= 151.1, ¹H-NMR (CDCl₃, 400 MHz): δ 3.09-3.03 (m, 4H), 2.56-2.55 (m, 1H), 2.05-2.00 (m, 4H), 1.40-1.39 (m, 2H), 1.14-1.12 (m, 2H).

Example 14A: 1'-azaspiro[cyclopropane-1,2'-bicyclo [2.2.2]octan]-3'-one oxime hydrochloride (A-10)

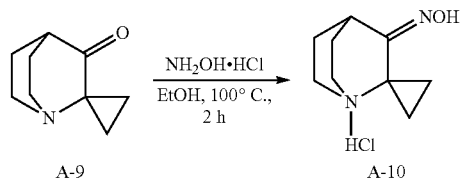

To a mixture of compound A-9 (1.0 g, 6.6 mmol) in anhydrous ethanol (5 mL) was added hydroxylamine hydrochloride (0.48 g, 7.0 mmol) at room temperature. The mixture was stirred at 100° C. for 2 hours. On completion, the solution was cooled to room temperature, resulting in formation of a precipitate. The precipitation was collected by filtration to give compound A-10 (0.80 g, 60% yield) as a white solid.

Example 15A: (+/−)-1'-azaspiro[cyclopropane-1,2'-bicyclo[2.2.2]octan]-3'-amine (rac-A-11)

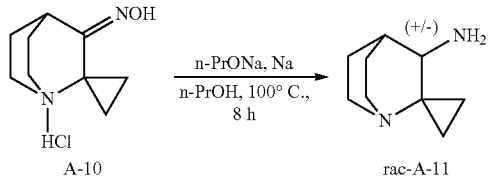

To a mixture of compound A-10 (1.0 g, 4.9 mmol) in n-propyl alcohol (10 mL) was added sodium propoxide (0.40 g, 4.9 mmol sodium in 2 mL n-propyl alcohol) at room temperature. The solution was heated to 100° C., and sodium (1.1 g, 49 mmol) was added in portions. The mixture was stirred at this temperature for 8 hours. On completion, the mixture was poured into water (2 mL), concentrated in vacuo, diluted with dichloromethane and filtered. The resulting filtrate was concentrated in vacuo to give rac-A-11 (0.50 g, 67% yield) as a yellow oil.

Example 16A: (R)-1-phenyl-N-(1'-azaspiro[cyclopropane-1,2'-bicyclo[2.2.2]octan]-3'-ylidene)ethanamine ((R)-A-12)

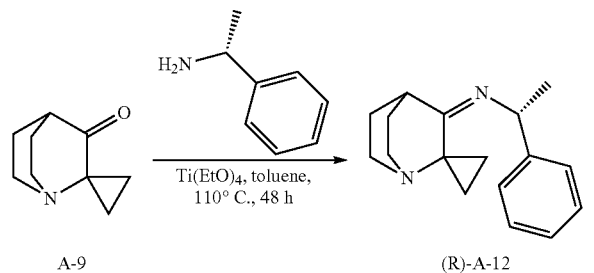

To a solution of compound A-9 (2.0 g, 13 mmol) in anhydrous toluene (30 mL) was added (R)-1-phenylethanamine (1.6 g, 13 mmol) and ethyl titanate (9.1 g, 40 mmol). The resulting mixture was stirred at 110° C. for 48 hours. On completion, the reaction was quenched with saturated aqueous potassium carbonate (100 mL) and extracted with ethyl acetate (3×100 mL). The combined organic layers were washed with brine, dried over sodium sulfate and concentrated in vacuo to give compound (R)-A-12 (3.2 g, crude) as a yellow oil, which was used for next step without further purification. LCMS (J): tR=1.594, (ES$^+$) m/z (M+H)$^+$= 255.1.

Example 17A: (R)—N—((R)-1-phenylethyl)-1'-azaspiro[cyclopropane-1,2'-bicyclo[2.2.2]octan]-3'-amine ((R,R)-A-13)

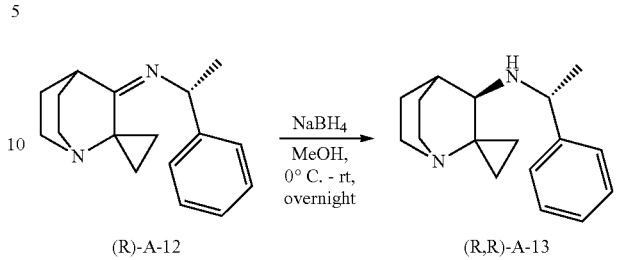

To a mixture of compound (R)-A-12 (3.2 g, 13 mmol) in anhydrous methanol (30 mL) was added sodium borohydride (1.0 g, 25 mmol) slowly at 0° C. The resulting mixture was stirred at room temperature overnight. On completion, the reaction was quenched with water (10 mL) and extracted with ethyl acetate (3×30 mL). The combined organic layers were washed with brine, dried over sodium sulfate, concentrated in vacuo and purified by silica gel chromatography [dichloromethane: methanol=5:1] to give compound (R,R)-A-13 (1.1 g, 41% yield for two steps) as a yellow oil. $^1$H-NMR (CD$_3$OD, 400 MHz): 7.34-7.28 (m, 4H), 7.24-7.22 (m, 1H), 3.66-3.63 (m, 1H), 3.01-2.89 (m, 1H), 2.74-2.73 (m, 1H), 2.72-2.65 (m, 3H), 1.90-1.79 (m, 2H), 1.70-1.65 (m, 1H), 1.55-1.51 (m, 1H), 1.37-1.35 (m, 1H), 1.29 (d, J=6.4 Hz, 3H), 1.12-1.07 (m, 1H), 0.85-0.80 (m, 1H), 0.59-0.47 (m, 2H).

Example 18A: (R)-1'-azaspiro[cyclopropane-1,2'-bicyclo[2.2.2]octan]-3'-amine ((R)-A-11)

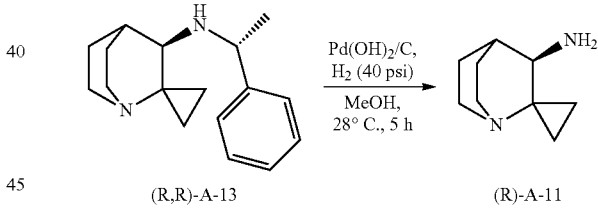

To a mixture of compound (R,R)-A-13 (1.4 g, 5.5 mmol) in anhydrous methanol (15 mL) was added 10% palladium hydroxide/carbon, 50% wet (600 mg) under nitrogen. The suspension was degassed in vacuo and purged with hydrogen several times. The resulting mixture was stirred under hydrogen (40 psi) at 28° C. for 5 hours. On completion, the reaction mixture was filtered, and the filtrate was concentrated in vacuo to give compound (R)-A-11 (0.75 g, 90% yield) as a light yellow oil. $^1$H-NMR (CD$_3$OD, 400 MHz): 3.04-2.94 (m, 2H), 2.82-2.76 (m, 3H), 1.92-1.84 (m, 2H), 1.79-1.70 (m, 2H), 1.46-1.43 (m, 1H), 1.00-0.95 (m, 1H), 0.82-0.77 (m, 1H), 0.58-0.49 (m, 2H).

The ditosylate salt form of compound (R)-A-11 can also be prepared by dissolving compound (R)-A-11 (18 g, 112 mmol) in anhydrous dichloromethane (180 mL) followed by addition of 4-methylbenzenesulfonic acid (39 g, 225 mmol). The mixture was stirred at 25° C. for 4 hours and then concentrated in vacuo. Anhydrous ethanol (500 mL) and anhydrous methanol (5 mL) were added, and the mixture was stirred for 12 hours. The solid was collected by filtration and dried in vacuo to give compound (R)-A-11 ditosylate (47 g, 84% yield) as a white solid. 1H-NMR (CD3OD, 400 MHz): 7.71-7.69 (d, J=8.0 Hz, 4H), 7.26-7.24 (d, J=8.0 Hz, 4H), 3.82-3.81 (m, 1H), 3.58-3.50 (m, 3H), 3.48-3.38 (m, 1H), 2.53-2.52 (m, 1H), 2.38 (s, 6H), 2.18-2.06 (m, 4H), 1.46-1.43 (m, 1H), 1.38-1.29 (m, 2H), 1.23-1.20 (m, 1H).

Example 19A: (S)-1-phenyl-N-(1'-azaspiro[cyclopropane-1,2'-bicyclo[2.2.2]octan]-3'-ylidene)ethanamine ((S)-A-12)

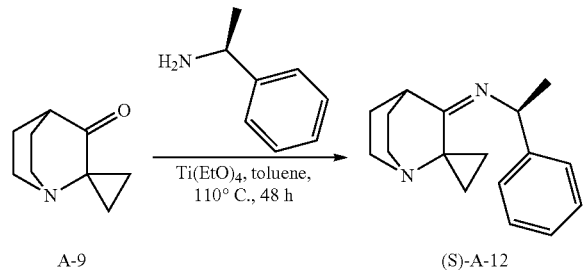

To a solution of compound A-9 (2.0 g, 13 mmol) in anhydrous toluene (30 mL) was added (S)-1-phenylethanamine (1.6 g, 13 mmol) and ethyl titanate (9.1 g, 40 mmol). The resulting mixture was stirred at 110° C. for 48 hours. On completion, the reaction was quenched with saturated aqueous potassium carbonate (100 mL) and extracted with ethyl acetate (5×30 mL). The combined organic layers were washed with brine, dried over sodium sulfate and concentrated in vacuo to give compound (S)-A-12 (2.3 g, crude) as a yellow oil, which was used for the next step without further purification. LCMS (J): tR=1.295, (ES$^+$) m/z (M+H)$^+$= 255.1.

Example 20A: (S)—N—((S)-1-phenylethyl)-1'-azaspiro[cyclopropane-1,2'-bicyclo[2.2.2]octan]-3'-amine ((S,S)-A-13)

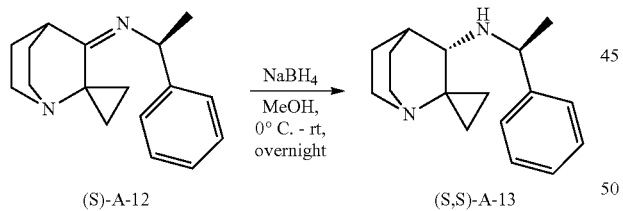

To a mixture of compound (S)-A-12 (2.3 g, crude) in anhydrous methanol (25 mL) was added sodium borohydride (1.0 g, 25 mmol) slowly at 0° C. The resulting mixture was stirred at room temperature overnight. On completion, the reaction was quenched by water (8 mL) and extracted with ethyl acetate (3×25 mL). The combined organic layers were concentrated in vacuo and purified by silica gel chromatography [dichloromethane: methanol=5:1] to give compound (S,S)-A-13 (1.0 g, 37%) yield for two steps) as a yellow oil. $^1$H-NMR (CD$_3$OD, 400 MHz): 7.32-7.25 (m, 4H), 7.22-7.18 (m, 1H), 3.64-3.58 (m, 1H), 3.02-2.99 (m, 1H), 2.89-2.86 (m, 1H), 2.76-2.64 (m, 3H), 1.85-1.76 (m, 2H), 1.67-1.65 (m, 1H), 1.52-1.50 (m, 1H), 1.34-1.32 (m, 1H), 1.26 (d, J=6.4 Hz, 3H), 1.08-1.04 (m, 1H), 0.82-0.78 (m, 1H), 0.56-0.46 (m, 2H).

Example 21A: (S)-1'-azaspiro[cyclopropane-1,2'-bicyclo[2.2.2]octan]-3'-amine ((S)-A-11)

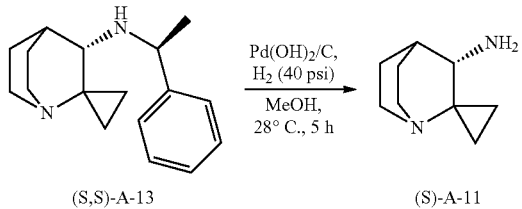 [SMILES: C[C@H](N[C@H]1C2CCN(CC2)C12CC2)c1ccccc1 ; "Pd(OH)2/C,H2 (40 psi)" ; N[C@H]1C2CCN(CC2)C12CC2]

To a mixture of compound (S,S)-A-13 (1.0 g, 3.9 mmol) in anhydrous methanol (10 mL) was added 10% palladium hydroxide/carbon, 50% wet (400 mg) under nitrogen. The suspension was degassed in vacuo and purged with hydrogen several times. The mixture was stirred under hydrogen (40 psi) at 28° C. for 5 hours. On completion, the reaction mixture was filtered, and the filtrate was concentrated in vacuo to give compound (S)-A-11 (0.55 g, 92% yield) as a light yellow oil. $^1$H-NMR (CD$_3$OD, 400 MHz): 3.04-2.94 (m, 2H), 2.82-2.75 (m, 3H), 1.97-1.84 (m, 2H), 1.79-1.74 (m, 2H), 1.47-1.43 (m, 1H), 1.00-0.95 (m, 1H), 0.81-0.76 (m, 1H), 0.58-0.49 (m, 2H).

General Procedure A1: Synthesis of N-hydroxyimidoyl chloride.

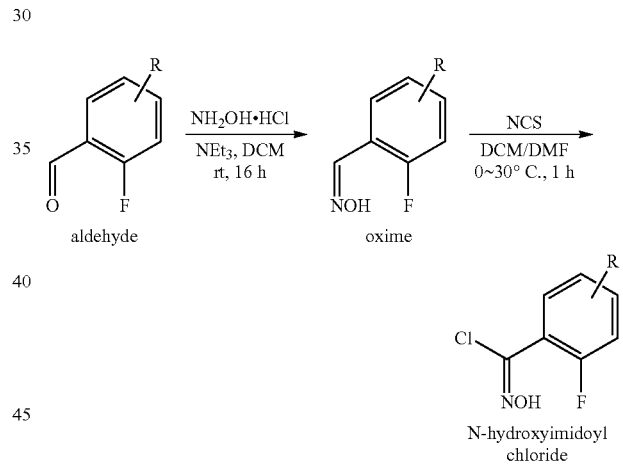

A mixture of aldehyde (1 eq.), hydroxylamine hydrochloride (1.3-2 eq.) and triethylamine (2 eq.) in dichloromethane (1.2-2.5 mL/mmol aldehyde) was stirred at room temperature for 16 hours. On completion, the reaction mixture was diluted with water and extracted with dichloromethane (3×20 mL). The combined organic layers were washed with water and brine, dried over anhydrous sodium sulfate and concentrated in vacuo to give the oxime intermediate. This intermediate was either purified by silica gel chromatography or used without further purification in the next step.

To a solution of oxime intermediate (1 eq.) in dichloromethane (10 mL) at 0° C. was added a solution of N-chlorosuccinimide (1.2 eq.) in N,N-dimethylformamide (0.5 mL). The mixture was stirred at 30° C. for 1 hour. On completion, the reaction mixture was diluted with water and extracted with dichloromethane (3×10 mL). The combined organic layers were washed with water and brine, dried over anhydrous sodium sulfate, filtered and concentrated in vacuo to give N-hydroxyimidoyl chloride intermediate, which was used crude in the next reaction without further purification.

Example 1B: 6-chlorobenzo[d]isoxazol-3-amine (B-1)

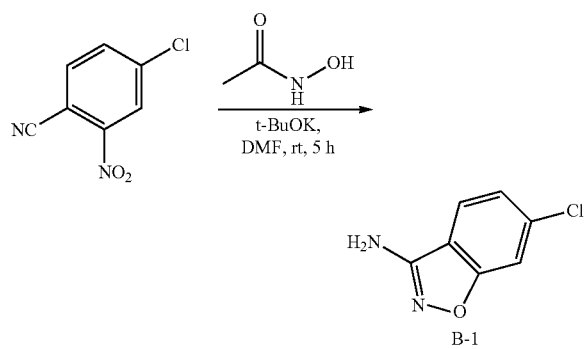

To a solution of N-hydroxyacetamide (3.1 g, 41 mmol) in dry N,N-dimethylformamide (60 mL) at room temperature was added potassium t-butoxide (4.6 g, 41 mmol). After stirring for 30 minutes, 4-chloro-2-nitrobenzonitrile (5.0 g, 27 mmol) was added, and stirring was continued for another 4.5 hours. On completion, the reaction mixture was poured into a mixture of brine (60 mL) and ethyl acetate (60 mL). The organic phase was separated, dried over anhydrous sodium sulfate, filtered and concentrated to dryness. The residue was purified by silica gel chromatography [petroleum ether: ethyl acetate=3:1] to afford compound B-1 (3.1 g, 66% yield) as a pale yellow solid. $^1$H-NMR (DMSO-$d_6$, 400 MHz): δ 7.84-7.82 (d, J=8.8 Hz, 1H), 7.65-7.64 (d, J=1.2 Hz, 1H), 7.33-7.31 (dd, J=1.2 Hz, J=8.8 Hz, 1H), 6.52 (s, 2H).

Example 2B: 4-chloro-2-fluoro-N-hydroxybenzimidoyl chloride (compound-B-3)

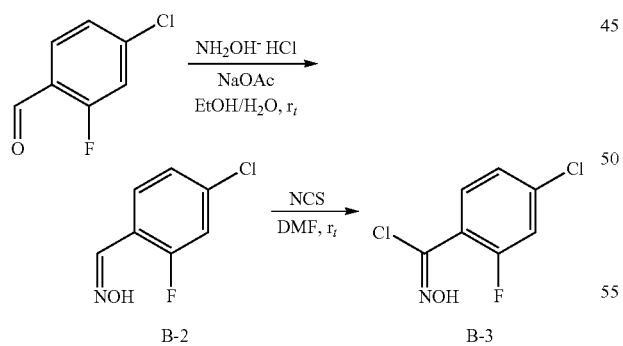

To a solution of 4-chloro-2-fluorobenzaldehyde (2.6 g, 16.4 mmol) in ethanol/water (45 mL, 8/1, v/v) at room temperature was added hydroxylamine hydrochloride (2.3 g, 32.8 mmol) and sodium acetate (4.0 g, 49.2 mmol). The reaction was stirred for 1 hour until TLC showed the reaction was complete. The mixture was concentrated in vacuo, and the residue was triturated from water, collected by filtration, washed with water and dried in vacuo to afford compound B-2 (2.7 g, white solid, 96% yield), which was used as such in the next step. LCMS (2): tR=1.856 min., (ES$^+$) m/z (M+H)$^+$=174.0. $^1$H NMR (300 MHz, DMSO-$d_6$) δ 11.83 (s, 1H), 8.16 (s, 1H), 7.87-7.63 (m, 1H), 7.62-7.41 (m, 1H), 7.31 (d, J=7.9 Hz, 1H).

To a solution of compound B-2 (2.7 g, 15.6 mmol) in N,N-dimethylformamide (25 mL) at room temperature was added N-chlorosuccinimide (2.1 g, 15.6 mmol). The reaction was stirred for 1.5 hours until TLC showed the reaction was complete. The solution was diluted with ethyl acetate and water and filtered through Celite to remove particles. The layers were separated, and the organic layer was washed with water and brine (2×), dried with sodium sulfate, filtered, and concentrated in vacuo to afford compound B-3 (2.7 g, white solid, 84% yield), which was used as such in the next step. 1H NMR (300 MHz, DMSO-$d_6$) δ 12.73 (s, 1H), 7.75-7.65 (m, 1H), 7.65-7.57 (m, 1H), 7.47-7.37 (m, 1H).

Example 3B: (4,5-dichloro-2-fluorophenyl)methanol (B-4)

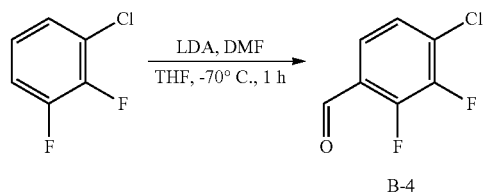

To a solution of 1-chloro-2,3-difluorobenzene (1.0 g, 6.7 mmol) in dry tetrahydrofuran (15 mL) under nitrogen at −70° C. was added dropwise lithium diisopropylamide (2 M in tetrahydrofuran, 4.0 mL, 8.1 mmol). The reaction was stirred at −70° C. for 0.5 hour, then N,N-dimethyl formamide (1.5 g, 20 mmol) was added dropwise, and stirring was continued at −70° C. for another 0.5 hour. On completion, the reaction mixture was quenched with saturated aqueous ammonium chloride (15 mL) and extracted with ethyl acetate (3×15 mL). The combined organic layers were washed with brine, dried over anhydrous sodium sulfate, filtered and concentrated in vacuo. The residue was purified by silica gel chromatography [petroleum ether: ethyl acetate=10:1] to give compound B-4 (1.0 g, 85% yield) as a white solid. $^1$H-NMR (CDCl$_3$, 400 MHz): δ 10.31 (s, 1H), δ 7.65-7.63 (m, 1H), 7.38-7.32 (m, 1H).

Example 4B: 4-chloro-2,3-difluoro-N-hydroxybenzimidoyl chloride (B-6)

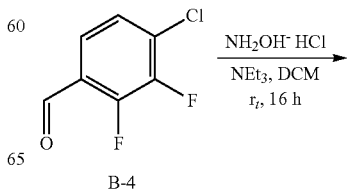

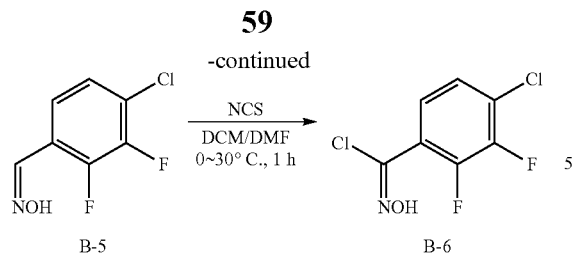

Following general procedure A1, compound B-6 was prepared from compound B-4:

Compound B-5 (0.29 g, white solid, 89% yield) was prepared from compound B-4 (0.30 g, 1.7 mmol) and purified by silica gel chromatography [petroleum ether: ethyl acetate=10:1]. LCMS (B): (ES$^+$) m/z (M+H)$^+$=192.1, tR=0.742.

Compound B-6 (0.28 g, white solid, crude) was prepared from compound B-5 (0.29 g, 1.5 mmol). TLC [petroleum ether: ethyl acetate=3:1]: Rf=0.4.

Example 5B:
2-fluoro-N-hydroxy-4-methoxybenzimidoyl chloride (B-8)

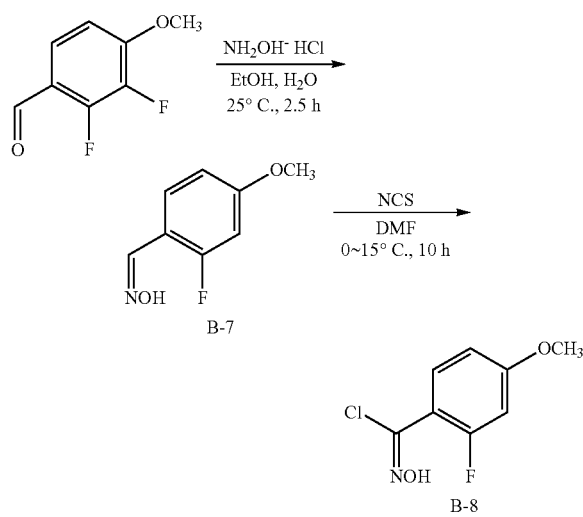

Following general procedure A1, compound B-8 was prepared from 2-fluoro-4-methoxybenzaldehyde:

Compound B-7 (3.0 g, white solid, 90% yield) was prepared from 2-fluoro-4-methoxybenzaldehyde (3.0 g, 19 mmol) and hydroxylamine hydrochloride (4.1 g, 58 mmol), using ethanol and water as the solvent without triethylamine with a reaction time of 2.5 hours at 25° C. The product was purified by column chromatography [petroleum ether: ethyl acetate=10:1]. TLC [petroleum ether: ethyl acetate=5:1]: Rf=0.29. $^1$H-NMR (CDCl$_3$, 400 MHz): δ 8.51-8.47 (m, 1H), 8.30 (s, 1H), 7.67-7.62 (m, 1H), 6.76-6.72 (m, 1H), 6.67-6.62 (m, 1H), 3.83 (s, 3H).

Compound B-8 (0.77 g, yellow gum, crude) was prepared from compound B-7 (0.5 g, 3.0 mmol) and N-chlorosuccinimide (0.40 g, 3.0 mmol) with a reaction time of 10 hours at 0-15° C. LCMS (B): tR=0.684 min, (ES$^+$) m/z (M+H)$^+$=204.1.

Example 6B: 3,4-dichloro-2-fluorobenzaldehyde (B-9)

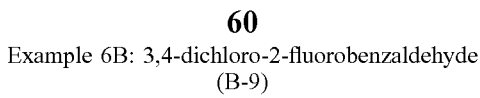
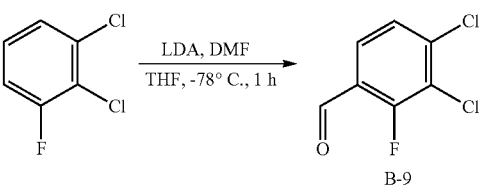

To a solution of 1,2-dichloro-3-fluorobenzene (2.5 g, 15.2 mmol) in tetrahydrofuran (15 mL) at −78° C. was added lithium diisopropylamide (2 M in tetrahydrofuran/n-heptane, 11.5 mL, 23 mmol). The reaction was stirred for 0.5 hour. Then N,N-dimethylformamide (3.33 g, 45 mmol) was added, and the reaction was stirred at −78° C. for another 0.5 hour. On completion, the reaction was quenched with water and extracted with ethyl acetate (3×15 mL). The combined organic layers were washed with water and brine, dried over anhydrous sodium sulfate and concentrated in vacuo to give compound B-9 (2.8 g, crude) as yellow oil.

Example 7B:
3,4-dichloro-2-fluoro-N-hydroxybenzimidoyl chloride (B-11)

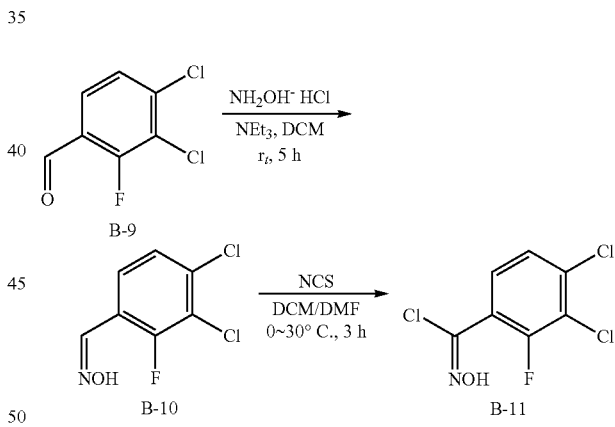

Following general procedure A1, compound B-11 was prepared from compound B-9.

Compound B-10 (2.3 g, white solid, crude) was prepared from compound B-9 (2.8 g, 15 mmol) with a reaction time of 5 hours and purified by silica gel chromatography [petroleum ether: ethyl acetate=10:1]. LCMS (J): (ES$^+$) m/z (M+H)$^+$=208.0, tR=0.786.

Compound B-11 (2.2 g, white solid, crude) was prepared from compound B-10 (2.3 g, 11 mmol) with a reaction time of 3 hours. TLC [petroleum ether: ethyl acetate=8:1]: Rf=0.5.

Example 8B:
4-chloro-2-fluoro-N-hydroxy-3-methoxybenzimidoyl chloride (B-13)

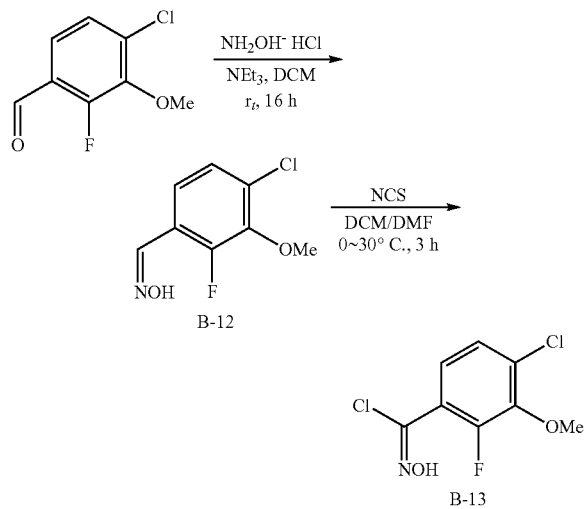

Following general procedure A1, compound B-13 was prepared from 4-chloro-2-fluoro-3-methoxybenzaldehyde:

Compound B-12 (2.0 g, white solid, crude) was prepared from 4-chloro-2-fluoro-3-methoxybenzaldehyde (2.5 g, 13 mmol) and purified by silica gel chromatography [petroleum ether: ethyl acetate=10:1].

Compound B-13 (2.5 g, white solid, crude) was prepared from compound B-12 (2.5 g, 12 mmol) with a reaction time of 3 hours. TLC [petroleum ether: ethyl acetate=5:1]: Rf=0.7.

Example 9B:
2-fluoro-N-hydroxy-4-methylbenzimidoyl chloride (B-15)

Following general procedure A1, compound B-15 was prepared from 2-fluoro-4-methyl benzaldehyde:

Compound B-14 (1.8 g, white solid, crude) was prepared from 2-fluoro-4-methyl benzaldehyde (2.0 g, 14.5 mmol) with a reaction time of 2 hours and purified by silica gel chromatography [petroleum ether: ethyl acetate=15:1]. 1H-NMR (CDCl$_3$, 400 MHz): δ 8.55-8.35 (m, 2H), 7.62-7.61 (m, 1H), 6.99-6.92 (m, 2H), 2.38 (s, 3H).

Compound B-15 (2.5 g, white solid, crude) was prepared from compound B-14 (2.0 g, 13 mmol) with a reaction time of 1.5 hours. TLC [petroleum ether: ethyl acetate=5:1]: Rf=0.7.

Example 10B:
2,3-difluoro-N-hydroxy-4-methylbenzimidoyl chloride (B-17)

Following general procedure A1, compound B-17 was prepared from 2,3-difluoro-4-methylbenzaldehyde:

Compound B-16 (1.0 g, white solid, 91% yield) was prepared from 2,3-difluoro-4-methylbenz aldehyde (1.0 g, 6.4 mmol) and purified by silica gel chromatography [petroleum ether: ethyl acetate=10:1]. LCMS (J): (ES$^+$) m/z (M+H)$^+$=172.1, tR=1.279.

Compound B-17 (0.60 g, white solid, crude) was prepared from compound B-16 (0.50 g, 3.2 mmol) with a reaction of 16 hours. TLC [petroleum ether:ethyl acetate=5:1]: Rf=0.5.

Example 11B:
3-chloro-2,4-difluoro-N-hydroxybenzimidoyl chloride (B-19)

Following general procedure A1, compound B-19 was prepared from 3-chloro-2,4-difluorobenzaldehyde:

Compound B-18 (0.90 g, white solid, 83% yield) was prepared from 3-chloro-2,4-difluorobenzaldehyde (1.0 g, 5.7 mmol) and used in next step without further purification.

Compound B-19 (0.80 g, white solid, crude) was prepared from compound B-18 (0.90 g, 4.7 mmol) with a reaction time of 16 hours at room temperature. TLC [petroleum ether: ethyl acetate=8:1]: Rf=0.75.

Example 12B:
(2,5-difluoro-4-methylphenyl)methanol (B-20)

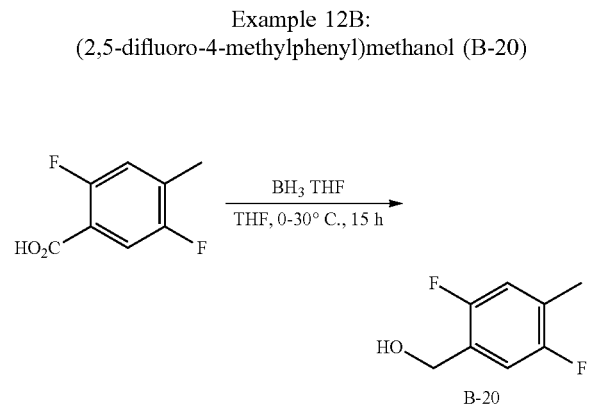

To a solution of compound 2,5-difluoro-4-methyl-benzoic acid (2.00 g, 11.6 mmol, 1.00 eq) in tetrahydrofuran (30 mL) at 0° C. was added dropwise BH$_3$.THF (1 M, 29.1 mL, 2.50 eq). The reaction was stirred at 30° C. for 15 hours. On completion, the reaction was quenched with methanol (60 mL) and concentrated in vacuo to give compound B-20 (1.8 g, yellow solid, crude). 1H-NMR (CD$_3$OD, 400 MHz): δ 7.15-7.10 (m, 1H), 7.00-6.94 (m, 1H), 4.61 (s, 2H), 2.26 (s, 3H).

Example 13B: 2,5-difluoro-4-methylbenzaldehyde (B-21)

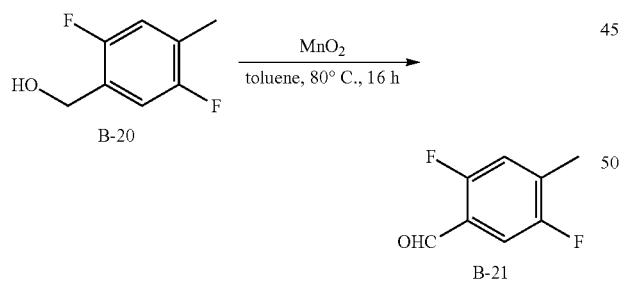

To a solution of compound B-20 (1.80 g, 11.4 mmol, 1.00 eq) in toluene (15.00 mL) was added manganese dioxide (9.90 g, 114 mmol, 10.0 eq). The mixture was stirred at 80° C. for 16 hours. The reaction mixture was filtered and the filtrate was concentrated in vacuo to give compound B-21 (1.5 g, 84% yield) as a yellow solid. 1H-NMR (CDCl$_3$, 400 MHz): δ 10.29 (m, 1H), 7.54-7.48 (m, 1H), 7.07-7.03 (m, 1H), 2.38-2.34 (m, 3H).

Example 14B:
2,5-difluoro-N-hydroxy-4-methylbenzimidoyl chloride (B-23)

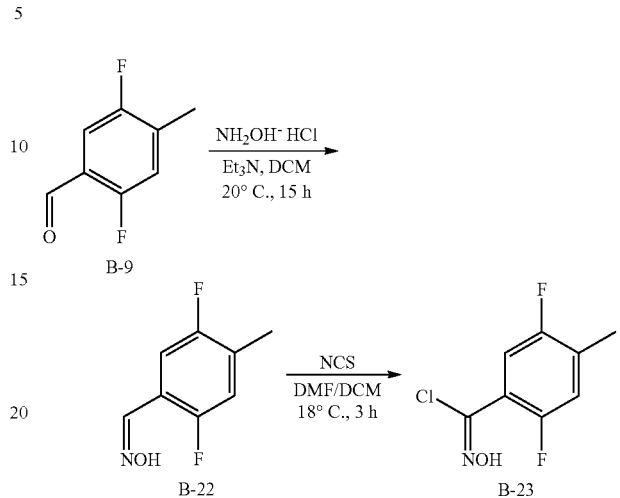

Following general procedure A1, compound B-23 was prepared from compound B-21:

Compound B-22 (1.6 g crude) was prepared from compound B-21 (1.4 g, 8.9 mmol) with a reaction temperature of 20° C. and a reaction time of 15 hours and purified by silica gel chromatography [petroleum ether: ethyl acetate=20:1]. 1H-NMR (CDCl$_3$, 400 MHz): δ 8.30 (s, 1H), 7.65 (s, 1H), 7.45-7.38 (m, 1H), 7.02-6.91 (m, 1H), 2.30 (s, 3H).

Compound B-23 (1.6 g, crude) was prepared from compound B-22 (1.6 g, 9.35 mmol) with a reaction temperature of 18° C. and a reaction time of 3 hours. TLC [petroleum ether: ethyl acetate=10:1]: Rf=0.5.

Example 15B:
4-chloro-2-fluoro-3-methylbenzaldehyde (B-24)

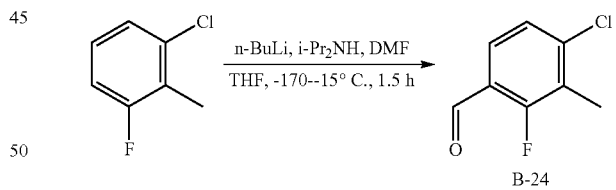

To a solution of diisopropylamine (1.5 eq) in tetrahydrofuran (80 mL) at −70° C. was added n-butyllithium (2.5 M in n-hexane, 21 mL, 52 mmol) at −70° C. under nitrogen and the reaction was stirred at −15° C. for 0.5 hour. Then the reaction solution was cooled to −70° C. and 1-chloro-3-fluoro-2-methylbenzene was added. The mixture was stirred for another 0.5 hour at −70° C. Finally N, N-dimethylformamide (12.6 g, 173 mmol) was added slowly and the mixture was stirred at −70° C. for another 0.5 hour. One completion, the reaction was quenched with aqueous ammonium chloride (250 mL) and extracted with ethyl acetate (3×250 mL). The combined organic extracts were concentrated in vacuo to give compound B-24 (6 g, crude) as a yellow oil.

Example 16B:
4-chloro-2-fluoro-N-hydroxy-3-methylbenzimidoyl chloride (B-26)

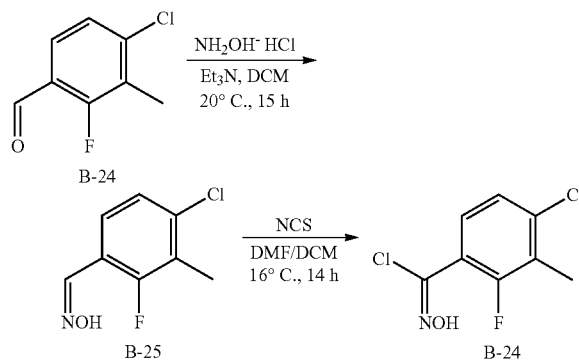

Following general procedure A1, compound B-26 was prepared from compound B-24:

Compound B-25 (0.4 g crude) was prepared from compound B-24 (5.0 g, 29 mmol) with a reaction temperature of 20° C. and a reaction time of 15 hours and purified by silica gel chromatography [petroleum ether: ethyl acetate=20:1]. 1H-NMR (CDCl$_3$, 400 MHz): δ 8.34 (s, 1H), 7.89 (s, 1H), 7.56-7.53 (m, 1H), 7.20-7.18 (m, 1H), 2.34 (s, 3H).

Compound B-26 (0.52 g, crude) was prepared from compound B-25 (0.5 g, 2.67 mmol) with a reaction temperature of 16° C. and a reaction time of 14 hours. TLC [petroleum ether: ethyl acetate=9:1]: Rf=0.5.

Example 17B:
4-chloro-2,5-difluoro-N-hydroxybenzimidoyl chloride (B-28)

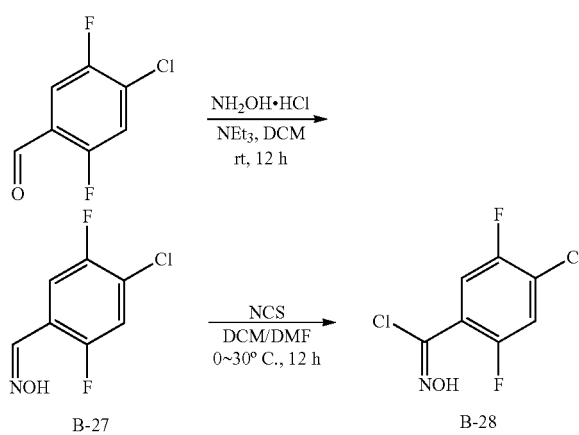

Following general procedure A1, compound B-28 was prepared from 4-chloro-2,5-difluorobenzaldehyde:

Compound B-27 (1.5 g, white solid, 92% yield) was prepared from 4-chloro-2,5-difluorobenzaldehyde (1.5 g, 8.5 mmol) with a reaction time of 12 hours and purified by silica gel chromatography [petroleum ether: ethyl acetate=50:1-5:1]. 1H-NMR (DMSO, 400 MHz): δ 11.90 (s, 1H), 8.16 (t, J=8.0 Hz, 1H), 7.76-7.66 (m, 2H).

Compound B-28 (0.60 g, yellow oil, crude) was prepared from compound B-27 (0.50 g, 2.6 mmol) with a reaction time of 12 hours. TLC [petroleum ether: ethyl acetate=10:1]: Rf=0.40.

Example 18B:
4-chloro-3-ethoxy-2-fluoro-N-hydroxybenzimidoyl chloride (B-30)

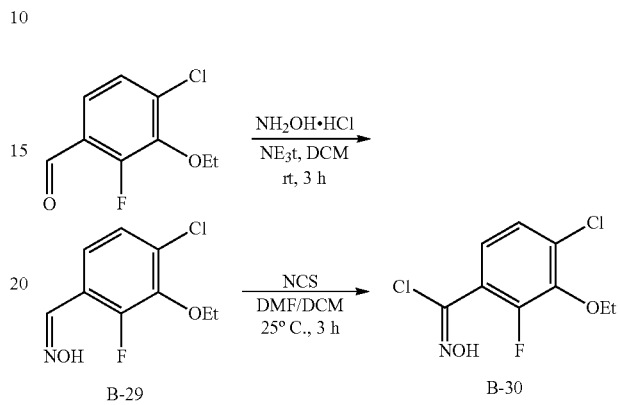

Following general procedure A1, compound B-30 was prepared from 4-chloro-3-ethoxy-2-fluorobenzaldehyde:

Compound B-29 (0.80 g, white solid, 74% yield) was prepared from 4-chloro-3-ethoxy-2-fluorobenzaldehyde (1.0 g, 4.9 mmol) with a reaction time of 3 hours and purified by silica gel chromatography [petroleum ether: ethyl acetate=5:1].

Compound B-30 (1.0 g, yellow oil, crude) was prepared from compound B-29 (0.80 g, 3.5 mmol) with a reaction temperature of 25° C. and a reaction time of 3 hours. TLC [petroleum ether: ethyl acetate=8:1]: Rf=0.7.

Example 19B:
3-chloro-2-fluoro-4-methylbenzaldehyde (B-31)

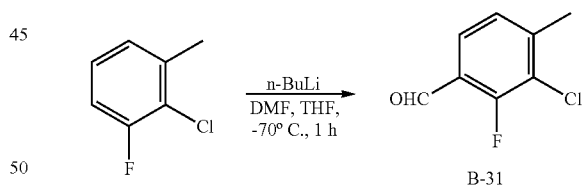

To a mixture of compound 2-chloro-1-fluoro-3-methylbenzene (2.0 g, 14 mmol) in anhydrous tetrahydrofuran (20 mL) at −70° C. under nitrogen was added dropwise n-butyllithium (2.5 M in n-hexane, 8.3 mL, 21 mmol). The mixture was stirred at −70° C. for 0.5 hour, and N,N-dimethylformamide (0.14 g, 1.9 mmol) was added dropwise. The reaction was stirred at −70° C. for another 0.5 hour. Then the reaction was quenched with saturated ammonium chloride solution (30 mL) at 0° C. and extracted with ethyl acetate (2×30 mL). The combined organic layers were washed with brine (2×20 mL), dried with anhydrous sodium sulfate, filtered and concentrated in vacuo to give compound B-31 (2.0 g, crude) as a yellow solid. 1H-NMR (CDCl$_3$, 400 MHz): δ 10.31 (s, 1H), 7.67 (t, J=7.2 Hz, 1H), 7.17 (dd, J=8.0 Hz, 1H), 2.48 (s, 3H).

Example 20B:
3-chloro-2-fluoro-N-hydroxy-4-methylbenzimidoyl chloride (B-33)

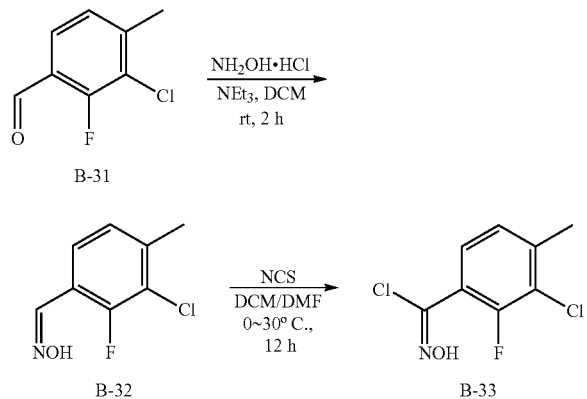

Following general procedure A1, compound B-33 was prepared from compound B-31:

Compound B-32 (0.80 g, white solid, 74% yield) was prepared from compound B-31 (1.0 g, 5.8 mmol) with a reaction time of 2 hours and purified by silica gel chromatography [petroleum ether: ethyl acetate=50:1-10:1]. 1H-NMR (CDCl$_3$, 400 MHz): δ 8.34 (s, 1H), 7.87 (s, 1H), 7.55 (t, J=7.6 Hz, 1H), 7.05 (d, J=8.0 Hz, 1H), 2.42 (s, 3H).

Compound B-33 (0.90 g, yellow solid, crude) was prepared from compound B-32 (0.80 g, 4.3 mmol) with a reaction time of 12 hours. TLC [petroleum ether: ethyl acetate=10:1]: Rf=0.75.

Example 21B:
4-chloro-2-fluoro-3-(trifluoromethyl)benzaldehyde (B-34)

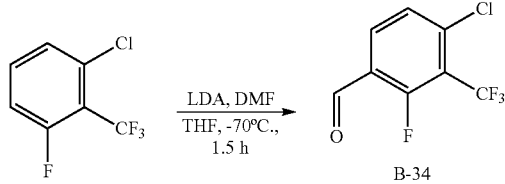

To a solution of 1-chloro-3-fluoro-2-(trifluoromethyl) benzene (0.50 g, 2.5 mmol) at −70° C. was added dropwise lithium diisopropylamide (2 M in tetrahydrofuran, 3.8 mmol, 1.9 mL). The reaction was stirred at −70° C. for 0.5 hour, then N,N-dimethylformamide (0.55 g, 7.6 mmol) was added slowly, and stirring was continued at −70° C. for another hour. The reaction was quenched with water (10 mL) and extracted with ethyl acetate (3×10 mL). The combined organic layers were concentrated in vacuo, and the residue was purified by silica gel chromatography [petroleum ether: ethyl acetate=10:1] to give B-34 (0.40 g, 70% yield) as a yellow solid. 1H-NMR (CDCl$_3$, 400 MHz): δ10.28 (s, 1H), 7.95-7.90 (t, J=10.0 Hz, 1H), 7.40-7.37 (d, J=11.2 Hz, 1H).

Example 22B: 4-chloro-2-fluoro-N-hydroxy-3-(trifluoromethyl)benzimidoyl chloride (B-36)

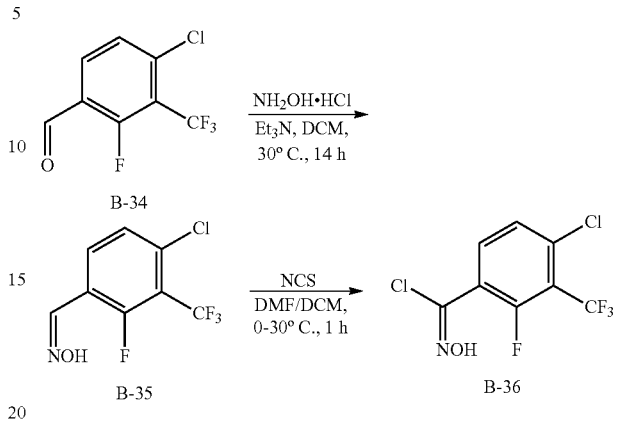

Following general procedure A1, compound B-36 was prepared from compound B-34:

Compound B-35 (0.40 g, yellow solid, 62% yield) was prepared from compound B-34 (0.60 g, 2.7 mmol) with a reaction time of 14 hours and used in next step without further purification.

Compound B-36 (0.40 g, white solid, crude) was prepared from compound B-35 (0.38 g, 1.6 mmol). TLC [petroleum ether: ethyl acetate=8:1]. Rf=0.6.

Example 23B:
1-chloro-3-fluoro-2-isopropoxybenzene (B-37)

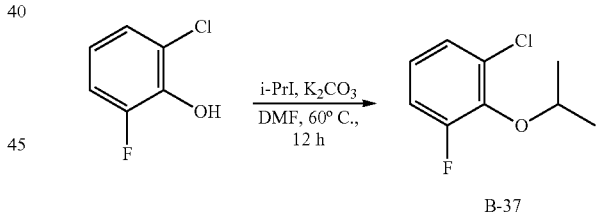

A mixture of 2-chloro-6-fluoro-phenol (5.0 g, 34 mmol), isopropyl iodide (12 g, 68 mmol) and potassium carbonate (19 g, 0.14 mol) in N,N-dimethylformamide (30 mL) was stirred at 60° C. for 12 hours. On completion, the reaction was diluted with water (30 mL) and extracted with ethyl acetate (2×30 mL). The combined organic phases were washed with brine (3×20 mL), dried with anhydrous sodium sulfate and concentrated in vacuo. The residue was purified by silica gel chromatography [petroleum ether: ethyl acetate=1:0] to give compound B-37 (5.0 g, 78% yield) as a colorless oil. $^1$H-NMR (CDCl$_3$, 400 MHz): δ 7.17-7.15 (m, 1H), 7.04-6.93 (m, 2H), 4.55-4.46 (m, 1H), 1.38-1.36 (d, J=6.4 Hz, 6H).

Example 24B:
4-chloro-2-fluoro-3-isopropoxybenzaldehyde (B-38)

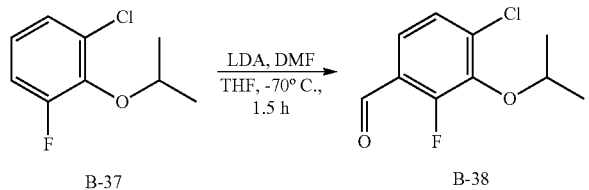

To a solution of compound B-37 (2.0 g, 11 mmol) at −70° C. under nitrogen was added dropwise lithium diisopropylamide (2 M in tetrahydrofuran, 8.0 mL, 16 mmol). The reaction was stirred at −70° C. for 1 hour. Then N,N-dimethylformamide (1.7 g, 23 mmol) was added slowly, and stirring was continued at −70° C. for another 0.5 hour. The reaction was quenched with saturated ammonium chloride solution (30 mL) and extracted with ethyl acetate (2×30 mL). The combined organic extracts were washed with water (20 mL), dried with anhydrous sodium sulfate and concentrated in vacuo to give compound B-38 (3.0 g, 27% purity, 35% yield) as a yellow solid. GCMS: m/z=216.0, tR=5.600 min.

Example 25B: 4-chloro-2-fluoro-N-hydroxy-3-isopropoxybenzimidoyl chloride (B-40)

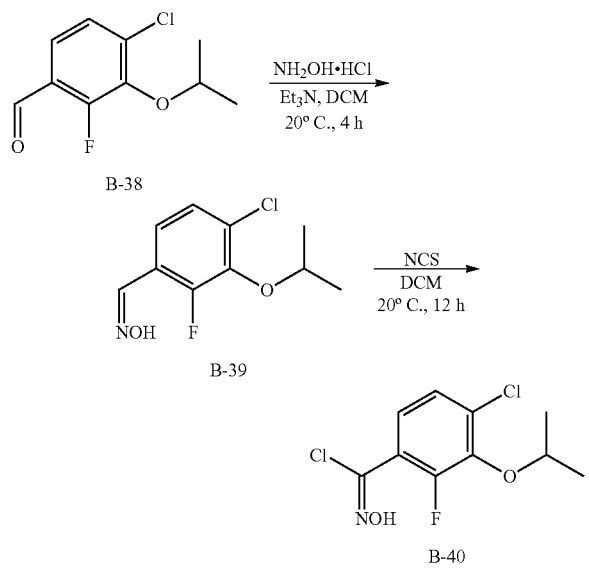

Following general procedure A1, compound B-40 was prepared from compound B-38:

Compound B-39 (600 mg, yellow solid, 69% yield) was prepared from compound B-38 (3.0 g, 27% purity) with a reaction temperature of 20° C. and a reaction time of 4 hours and purified by silica gel chromatography [petroleum ether: ethyl acetate=50:1-10:1]. 1H-NMR (CDCl$_3$, 400 MHz): δ 8.31 (s, 1H), 8.00 (s, 1H), 7.40 (t, J=8.0 Hz, 1H), 7.17 (dd, J=8.4 Hz, J=1.6 Hz, 1H), 4.56-4.47 (m, 1H), 1.38 (d, J=6.4 Hz, 6H).

Compound B-40 (0.70 g, yellow oil, crude) was prepared from compound B-39 (0.60 g, 2.6 mmol) using dichloromthane as solvent with a reaction temperature of 20° C. and a reaction time of 12 hours. TLC [petroleum ether: ethyl acetate=10:1]: Rf=0.61.

General Procedure B1: Synthesis of Aminobenzoisoxazoles.

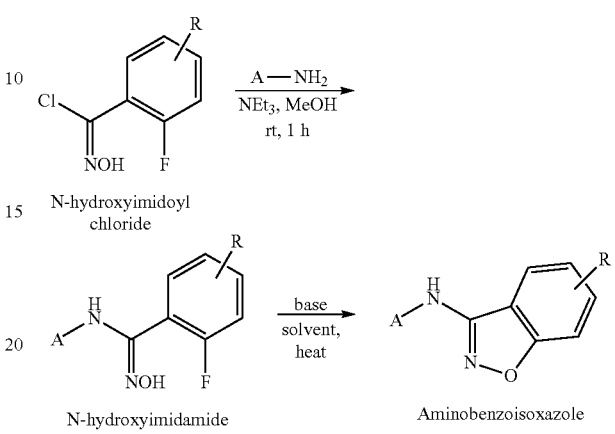

N-hydroxybenzimidoyl chloride intermediate (1 eq.) in methanol (7 mL/mmol imidoyl chloride intermediate) was added dropwise over 30 min. to a solution of amine A-NH$_2$ (1.2-2 eq.) and triethylamine (2 eq) in methanol (5-10 mL/mmol imidoyl chloride intermediate) at room temperature. The resulting mixture was stirred at room temperature for 30 min. On completion, the reaction mixture was concentrated in vacuo and purified by prep-HPLC to give the N-hydroxyimidamide intermediate.

A mixture of N-hydroxyimidamide intermediate and base, in an appropriate solvent, was heated until the reaction was judged complete by LCMS. The mixture was filtered, concentrated in vacuum and purified by prep-HPLC to give the the aminobenzoisoxazole product.

Example 1

Preparation of 6-chloro-N-(2,2-dimethylquinuclidin-3-yl)benzo[d]isoxazol-3-amine hydrochloride (rac-1)

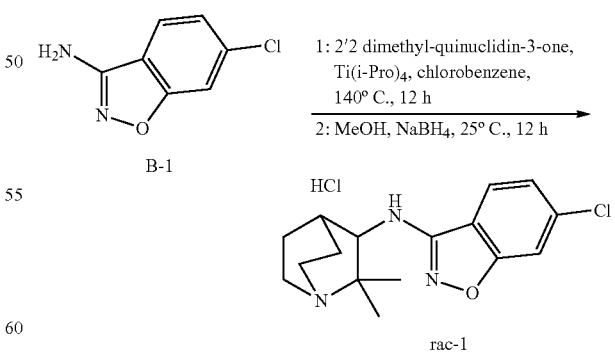

To a solution of compound B-1 (0.10 g, 0.6 mmol) and 2,2-dimethyl-quinuclidin-3-one (0.18 g, 1.2 mmol) in chlorobenzene (10 mL) at 25° C. was added portion-wise titanium (IV) isopropoxide (1.7 g, 6.0 mmol). The resulting solution was stirred at 140° C. for 12 hours. On completion, the mixture was cooled to 0° C., and methanol (2.0 mL) was added via, followed by sodium borohydride (0.23 g, 6.0 mmol) in portions. The reaction was stirred at 25° C. for 12 hours, then quenched with saturated aqueous potassium carbonate solution, resulting in the formation of a solid. The mixture was filtered, and the filtrate was extracted with dichloromethane (3×10 mL). The combined organic layers were washed with brine, dried over anhydrous sodium sulfate, filtered and concentrated in vacuo. The residue was purified by prep-HPLC [Instrument: GX-I; Column: Xtimate C18 150×25 mm, particle size: 5 μm; Mobile phase: 21-55% acetonitrile in H$_2$O (add 0.1% TFA, v/v)]. The resulting solid was dissolved in 0.2 N hydrochloric acid and again lyophilized to give rac-1 (10 mg, 2.0% yield) as a white solid. LCMS (B): tR=0.677 min., (ES$^+$) m/z (M+H)$^+$= 306.1. $^1$H-NMR (CD$_3$OD, 400 MHz): δ7.91 (d, J=8.4 Hz, 1H), 7.51 (d, J=1.6 Hz, 1H), 7.30 (dd, J=1.6 Hz, J=8.4 Hz, 1H), 3.93 (m, 1H), 3.72-3.67 (m, 2H), 3.36-3.31 (m, 2H), 2.42-2.41 (m, 1H), 2.37-2.36 (m, 1H), 2.17-2.10 (m, 2H), 1.92 (m, 1H), 1.78 (s, 3H), 1.52 (s, 3H).

Example Preparation of (R)-6-chloro-N-(2,2-dimethylquinuclidin-3-yl)benzo[d]isoxazol-3-amine ((R)-1)

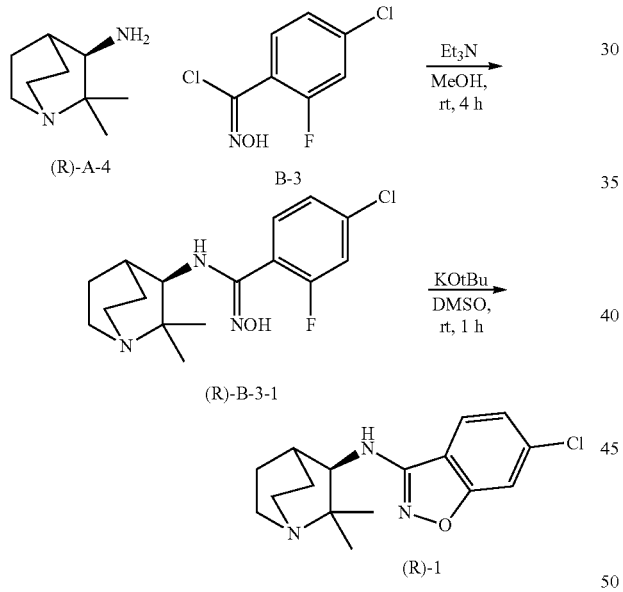

To a solution of (R)-A-4 (202 mg, 1.3 mmol) and triethylamine (139 mg, 1.4 mmol) in methanol (5 mL) at room temperature was added a solution of compound B-3 (286 mg, 1.4 mmol) in methanol (10 mL) over 4 hours using a syringe pump. Upon complete addition, the mixture was filtered and concentrated in vacuo, and the residue was purified by silica gel column chromatography [chloroform: 7M NH$_3$ in methanol=1:0 to 9:1] to afford (R)—B-3-1 (147 mg, 46% yield) as a white solid. LCMS (1): tR=2.847 min., (ES$^+$) m/z (M+H)$^+$=326.2.

To a solution of (R)-4-chloro-N-(2,2-dimethylquinuclidin-3-yl)-2-fluoro-N'-hydroxybenzimidamide (R)—B-3-1 (197 mg, 0.6 mmol) in dimethylsulfoxide (5 mL) was added potassium tertbutoxide (100 mg, 0.9 mmol). The mixture was stirred at room temperature for 1 hour. The solution was put on an SCX column and eluted with methanol. The product was eluted from the column using 3.5M ammonia in methanol, concentrated and purified by silica gel column chromatography [chloroform: 7M NH$_3$ in methanol=1/0 to 9/1]. The resulting product was further purified by preparative HPLC (1) and lyophilized to afford (R)-1 (70 mg, 38% yield) as a white solid: LCMS (3): tR=2.444 min., (ES+) m/z (M+H)+=306.0; 1H NMR (300 MHz, Chloroform-d) δ 7.45-7.39 (m, 2H), 7.21 (dd, J=8.4, 1.6 Hz, 1H), 4.46 (d, J=8.2 Hz, 1H), 3.70-3.63 (m, 1H), 3.33-3.19 (m, 2H), 2.82-2.67 (m, 2H), 2.08 (h, J=3.0 Hz, 1H), 1.82-1.61 (m, 3H), 1.49-1.40 (m, 4H), 1.31 (s, 3H).

Example 2: (R)-6-chloro-N-(2,2-dimethylquinuclidin-3-yl)-7-fluorobenzo[d]isoxazol-3-amine hydrochloride ((R)-2)

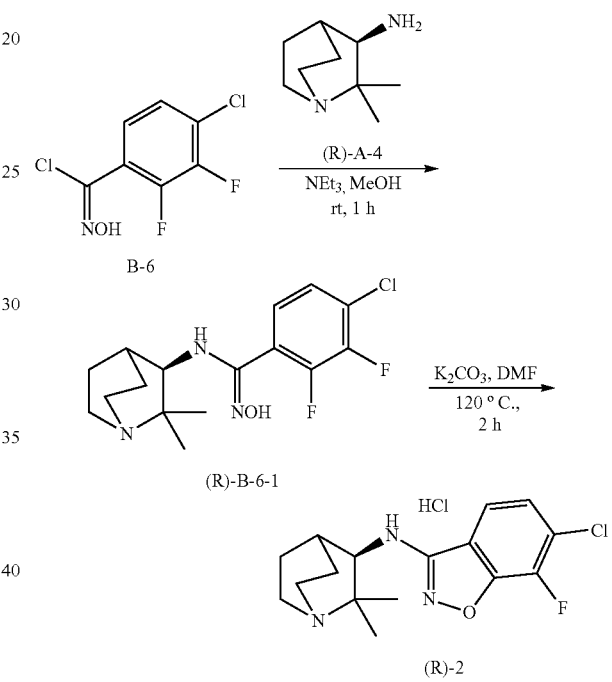

Following general procedure B1, compound (R)-2 was prepared from compound B-6:

Compound (R)-B-6-1 (71 mg, yellow solid, crude) was prepared from compound B-6 (50 mg, 0.22 mmol) and (R)-A-4 (34 mg, 0.22 mmol). The product was used in the next step without further purification. LCMS (G): (ES$^+$) m/z (M+H)$^+$=344.1, tR=2.36.

A mixture of compound (R)-B-6-1 (71 mg, 0.20 mmol) and potassium carbonate (85 mg, 0.60 mmol) in N,N-dimethylformamide (3.0 mL) was stirred at 120° C. for 2 hours. On completion, the reaction mixture was filtered, concentrated in vacuo and purified by prep-HPLC [Instrument: GX-I; Column: Xtimate C18 150×25 mm, particle size: 5 μm; Mobile phase: 20-50% acetonitrile in H$_2$O (add 0.1% TFA, v/v)]. The resulting solid was dissolved in 0.2 N hydrochloric acid and again lyophilized to give:

Compound (R)-2 (17 mg, 21% yield) as a white solid: cSFC analytical tR=2.10 min., purity: 97.05%; LCMS (FF): tR=2.40 min., 322.1 m/z (M+1); 1H-NMR (CD$_3$OD, 400 MHz): δ 7.76-7.74 (d, J=8.4 Hz 1H), 7.38-7.36 (m, 1H), 3.93 (m, 1H), 3.71-3.66 (m, 2H), 3.36-3.32 (m, 2H), 2.42 (m, 1H), 2.37-2.36 (m, 1H), 2.17-2.11 (m, 2H), 1.94-1.93 (m, 1H), 1.79 (s, 3H), 1.52 (s, 3H).

Example 3: (R)—N-(2,2-dimethylquinuclidin-3-yl)-6-methoxybenzo[d]isoxazol-3-amine hydrochloride ((R)-3)

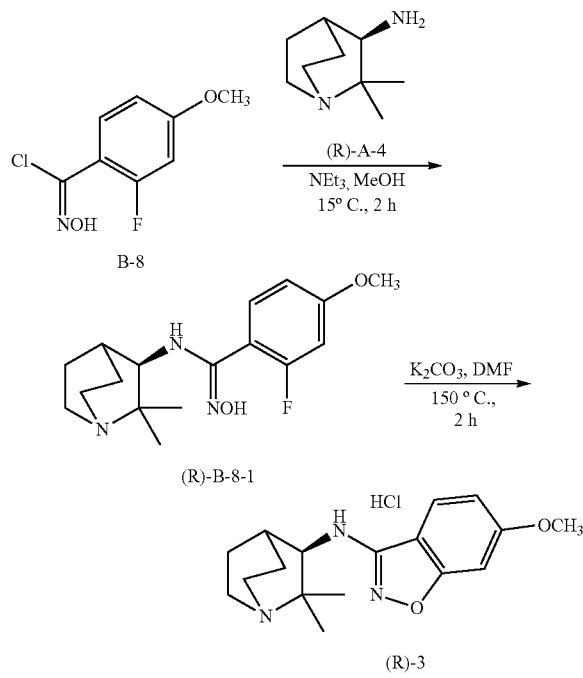

Following general procedure B1, compound (R)-3 was prepared from compound B-8:

Compound (R)-B-8-1 (0.22 g, white solid, 39% yield) was prepared from compound B-8 (0.4 g, 1.7 mmol), triethylamine (0.35 g, 3.4 mmol) and (R)-A-4 (0.26 g, 1.7 mmol) with a reaction time of 2 hours. The product was purified by prep-HPLC [Instrument: GX-A; Column: Phenomenex Gemini C18 250×50 mm, particle size: 10 μm; Mobile phase: 24-54% acetonitrile in $H_2O$ (add 0.05% $NH_3.H2O$, v/v)]. $^1$H-NMR (CDCl$_3$, 400 MHz): δ 7.29 (t, J=8.4 Hz, 1H), 6.85-6.78 (m, 2H), 3.84 (s, 3H), 3.30-3.26 (m, 1H), 3.04 (m, 1H), 2.90 (s, 1H), 2.72-2.62 (m, 2H), 1.86-1.85 (m, 1H), 1.74 (s, 1H), 1.68-1.63 (m, 1H), 1.51-1.45 (m, 2H), 1.28 (s, 3H), 0.99 (s, 3H).

A mixture of compound (R)-B-8-1 (0.10 g, 0.31 mmol) and potassium carbonate (129 mg, 0.93 mmol) in N,N-dimethylformamide (4 mL) was degassed and purged with nitrogen 3 times at 15° C., and then stirred at 150° C. for 2 hours under nitrogen atmosphere. The reaction mixture was filtered, concentrated in vacuo, and purified by prep-HPLC [Instrument: GX-B; Column: Phenomenex Synergi C18 150×30 mm, particle size: 4 μm; Mobile phase: 17-47% acetonitrile in $H_2O$ (add 0.1% TFA, v/v)]. The resulting solid was dissolved in 0.2 M hydrochloric acid and lyophilized to give compound (R)-3 (46 mg, 43% yield) as a white solid: cSFC analytical (D) tR=2.51 min., chiral purity: 88%.

A solution of compound (R)-3 at 88% chiral purity (0.10 g) in 3 mL of methanol was purified by cSFC (Instrument: SFC A; Column: Chiralpak AY-H-250×30 mm, I.D., 10 μm; Mobile phase: ethanol (0.05% DEA) in CO2) at room temperature. The collected fractions were concentrated at room temperature and lyophilized. The resulting solid was dissolved in 0.2 M hydrochloric acid and again lyophilized to give:

Compound (R)-3 (28 mg, 61% yield) as a white solid: cSFC analytical (D) tR=2.51 min., purity: 100%; LCMS (FF): tR=2.199 min., (ES+) m/z (M+H)+=302.1; 1H-NMR (CD$_3$OD, 400 MHz): δ 7.75 (d, J=8.4 Hz, 1H), 6.94 (d, J=1.6 Hz, 1H), 6.87 (dd, J=2.0 Hz, J=8.8 Hz, 1H), 3.90 (s, 1H), 3.87 (s, 3H), 3.73-3.66 (m, 2H), 3.35-3.27 (m, 2H), 2.41-2.35 (m, 2H), 2.16-2.09 (m, 2H), 1.95-1.91 (m, 1H), 1.77 (s, 3H), 1.52 (m, 3H).

Example 4: (R)-6,7-dichloro-N-(2,2-dimethylquinuclidin-3-yl)benzo[d]isoxazol-3-amine hydrochloride ((R)-4)

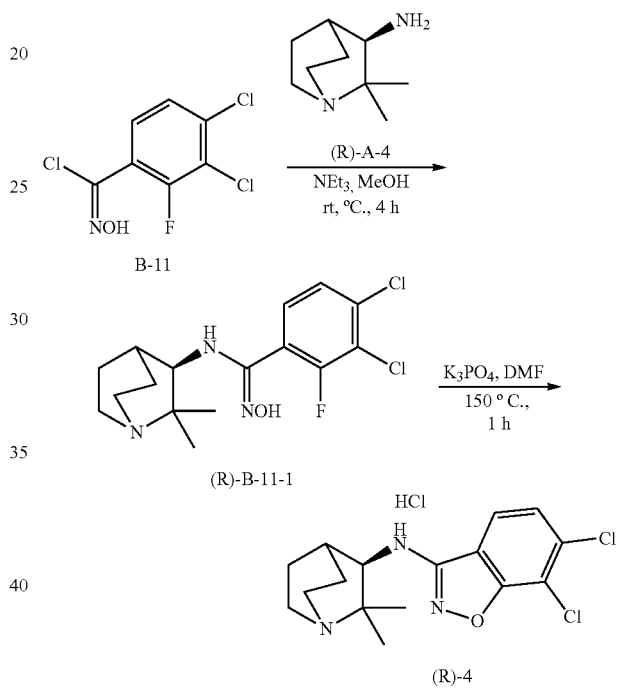

Following general procedure B1, compound (R)-4 was prepared from compound B-11:

Compound (R)-B-11-1 (96 mg, white solid, 43% yield) was prepared from compound B-11 (0.15 g, 0.62 mmol) and (R)-A-4 (94 mg, 0.62 mmol) with a reaction time of 4 hours. The product was purified by prep-HPLC [Instrument: GX-C; Column: Phenomenex Gemini C18 250×50 mm, particle size: 10 μm; Mobile phase: 32-62% acetonitrile in $H_2O$ (add 0.05% ammonia-ACN, v/v)]. LCMS (J): (ES$^+$) m/z (M+H)$^+$= 360.1, tR=1.28.

A solution of compound (R)-B-11-1 (70 mg, 0.19 mmol) and potassium phosphate (0.12 g, 0.58 mmol) in N,N-dimethylformamide (3.0 mL) was stirred at 150° C. for 1 hour. On completion, the reaction mixture was filtered and concentrated in vacuo. The residue was purified by prep-HPLC [Instrument: GX-I; Column: Xtimate C18 150×25 mm, particle size: 5 μm; Mobile phase: 18-48% acetonitrile in $H_2O$ (add 0.1% TFA-ACN, v/v)]. The resulting product was lyophilized, dissolved in 0.2 N hydrochloric acid and again lyophilized to give:

Compound (R)-4 (30 mg, 45% yield) as a white solid: cSFC analytical(D) tR=2.39 min., purity: 98.65%; LCMS (FF): tR=2.53 min., 340.1 m/z (M+1); 1H-NMR (CD₃OD, 400 MHz): δ 7.92 (d, J=8.4 Hz, 1H), 7.47 (d, J=8.4 Hz, 1H), 3.95 (m, 1H), 3.76-3.69 (m, 2H), 3.39-3.37 (m, 2H), 2.45-2.38 (m, 2H), 2.19-2.13 (m, 2H), 1.98-1.92 (m, 2H), 1.81 (m, 1H), 1.44-1.40 (S, 3H), 1.55 (m, 3H).

Example 5: (R)-6-chloro-N-(2,2-dimethylquinuclidin-3-yl)-7-methoxybenzo[d]isoxazol-3-amine hydrochloride ((R)-5)

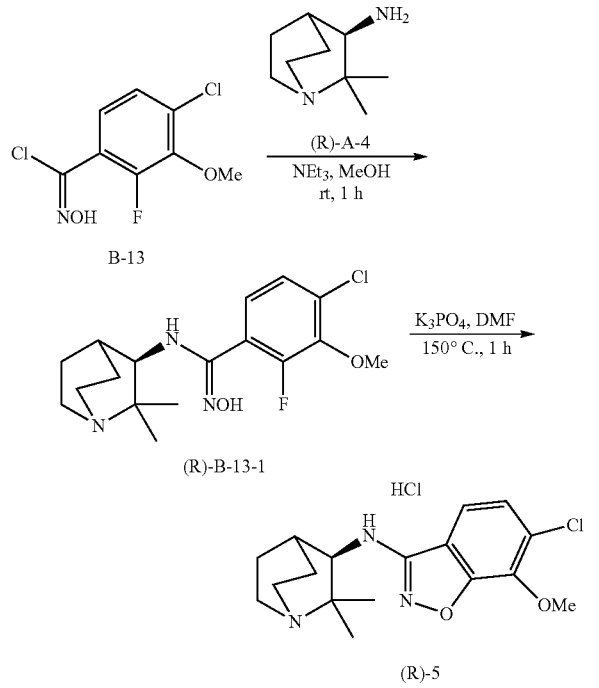

Following general procedure B1, compound (R)-5 was prepared from compound B-13:

Compound (R)-B-13-1 (75 mg, white solid, 17% yield) was prepared from compound B-13 (0.30 g, 1.26 mmol) and (R)-A-4 (0.19 g, 1.3 mmol). The product was purified by prep-HPLC [Instrument: GX-C; Column: Phenomenex Gemini 250×50 mm, particle size: 10 μm; Mobile phase: 24-54% acetonitrile in H₂O (add 0.5% NH₃H2O, v/v)]. LCMS (J): (ES⁺) m/z (M+H)⁺=354.1, tR=1.17.

A solution of compound (R)-B-13-1 (65 mg, 0.18 mmol) and potassium phosphate (0.12 g, 0.55 mmol) in N,N-dimethylformamide (1.5 mL) was stirred at 150° C. for 1 hours. On completion, the reaction mixture was filtered and concentrated in vacuo. The residue was purified by prep-HPLC [Instrument: GX-B; Column: Welch Ultimate AQ-C18 150×30 mm, particle size: 5 μm; Mobile phase: 37-67% acetonitrile in H₂O (add 0.1% TFA-ACN, v/v)]. The resulting solid was dissolved in 0.2 N hydrochloric acid and again lyophilized to give:

Compound (R)-5 (30 mg, 49% yield) as a white solid: cSFC analytical (D) tR=2.23 min., purity: 96.74%; LCMS (FF): tR=2.08 min., (ES⁺) m/z (M+H)⁺=336.1; 1H-NMR (CD₃OD, 400 MHz): δ 7.58 (d, J=8.4 Hz, 1H), 7.29 (d, J=8.4 Hz, 1H), 4.26 (m, 3H), 3.95 (s, 1H), 3.75-3.68 (m, 2H), 3.38-3.30 (m, 2H), 2.47-2.38 (m, 2H), 2.19-2.12 (m, 2H), 1.98-1.91 (m, 1H), 1.81 (s, 3H), 1.54 (s, 3H).

Example 6: (R)—N-(2,2-dimethylquinuclidin-3-yl)-6-methylbenzo[d]isoxazol-3-amine hydrochloride ((R)-6)

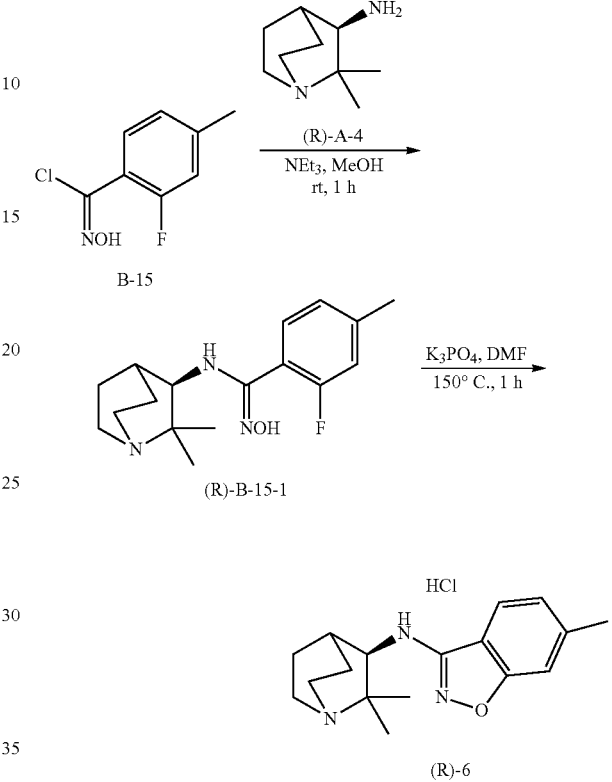

Following general procedure B1, compound (R)-6 was prepared from compound B-15:

Compound (R)-B-15-1 (75 mg, white solid, 18% yield) was prepared from compound B-15 (0.25 g, 1.3 mmol) and (R)-A-4 (0.21 g, 1.3 mmol) with a reaction time of 1 hour. The product was purified by prep-HPLC [Instrument: GX-C; Column: Phenomenex Gemini 250×50 mm, particle size: 10 μm; Mobile phase: 26-56% acetonitrile in H₂O (add 0.5% NH₃H2O, v/v)]. LCMS (J): (ES⁺) m/z (M+H)⁺=306.2, tR=1.13.

A solution of compound (R)-B-15-1 (65 mg, 0.21 mmol) and potassium phosphate (0.14 g, 0.64 mmol) in N,N-dimethylformamide (1.5 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150×30 mm, particle size: 10 μm; Mobile phase: 37-67% acetonitrile in H₂O (add 0.1% TFA-ACN, v/v)]. The resulting solid was dissolved in 0.2 N hydrochloric acid and again lyophilized to give:

Compound (R)-6 (30 mg, 49% yield) as a white solid: cSFC analytical (D) tR=2.35 min., purity: 100%; LCMS (FF): tR=1.97 min., (ES⁺) m/z (M+H)⁺=286.2; 1H-NMR (CD₃OD, 400 MHz): δ 7.78 (d, J=6.4 Hz, 1H), 7.21 (s, 1H), 7.11 (d, J=7.2 Hz, 1H), 3.92 (s, 1H), 3.69 (m, 2H), 3.32-3.29 (m, 2H), 2.47-2.3 (m, 5H), 1.91 (m, 1H), 1.77 (s, 3H), 1.51 (s, 3H).

Example 7: (R)—N-(2,2-dimethylquinuclidin-3-yl)-7-fluoro-6-methylbenzo[d]isoxazol-3-amine hydrochloride ((R)-7)

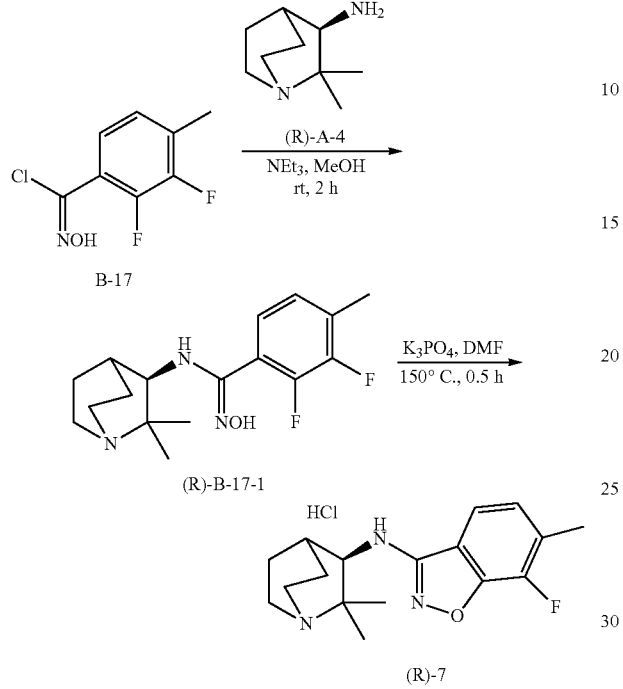

Example 8: (R)-7-chloro-N-(2,2-dimethylquinuclidin-3-yl)-6-fluorobenzo[d]isoxazol-3-amine hydrochloride ((R)-8)

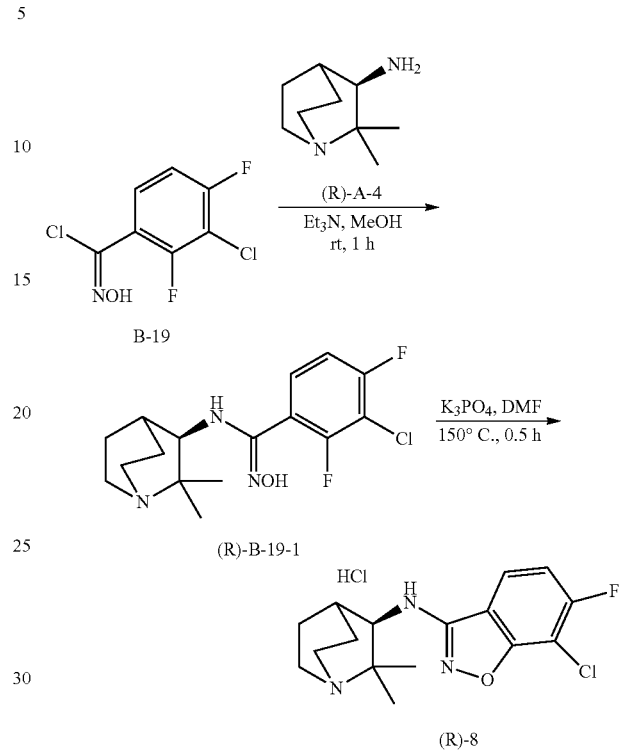

Following general procedure B1, compound (R)-7 was prepared from compound B-17:

Compound (R)-B-17-1 (0.15 g, white solid, 31% yield) was prepared from compound B-17 (0.30 g, 1.5 mmol) and (R)-A-4 (0.23 g, 1.5 mmol) with a reaction time of 2 hours. The product was purified by prep-HPLC [Instrument: GX-A; Column: Phenomenex Gemini C18 250×50 mm; particle size: 10 μm; Mobile phase: 28-58% acetonitrile in $H_2O$ (add 0.05% $NH_3$ $H_2O$, v/v)]. LCMS (J): ($ES^+$) m/z $(M+H)^+$=324.2, tR=1.183.

A mixture of compound (R)-B-17-1 (0.10 g, 0.31 mmol) and potassium phosphate (0.20 g, 0.93 mmol) in N,N-dimethylformamide (10 mL) was stirred at 150° C. for 0.5 hour. On completion, the reaction mixture was filtered and concentrated in vacuo. The residue was purified by prep-HPLC [Instrument: GX-I; Column: Welch Ultimate AQ-C18 150×30 mm; particle size: 5 μm; Mobile phase: 23-53% acetonitrile in $H_2O$ (add 0.1% TFA, v/v)]. The resulting solid was dissolved in 0.2 N hydrochloric acid and again lyophilized to give:

Compound (R)-7 (60 mg, 57% yield) as a white solid: cSFC analytical (D) tR=2.091 min., purity: 99.28%; LCMS (FF): tR=2.416 min., ($ES^+$) m/z $(M+H)^+$=324.1; $^1$H-NMR ($CD_3OD$, 400 MHz): δ 7.64-7.62 (d, J=8.4 Hz, 1H), 7.16-7.13 (m, 1H), 3.95 (s, 1H), 3.75-3.68 (m, 2H), 3.38-3.35 (m, 1H), 3.31-3.30 (m, 1H), 2.46-2.42 (m, 4H), 2.40-2.37 (m, 1H), 2.18-2.13 (m, 2H), 1.98-1.91 (m, 1H), 1.81 (s, 3H), 1.55 (s, 3H).

Following general procedure B1, compound (R)-8 was prepared from compound B-19:

Compound (R)-B-19-1 (0.30 g, white solid, 45% yield) was prepared from compound B-19 (0.44 g, 1.9 mmol) and (R)-A-4 (0.30 g, 1.9 mmol) with a reaction time of 16 hours. The product was purified by prep-HPLC [Instrument: GX-C; Column: Phenomenex Gemini C18 250×50 mm, particle size: 10 μm; Mobile phase: 30-60% acetonitrile in $H_2O$ (add 0.5% ammonia, v/v)]. LCMS (J): ($ES^+$) m/z $(M+H)^+$=344.1, tR=1.198.

A mixture of compound (R)-B-19-1 (0.10 g, 0.29 mmol) and potassium phosphate (0.19 g, 0.87 mmol) in N,N-dimethylformamide (10 mL) was stirred at 150° C. for 0.5 hour. On completion, the reaction mixture was filtered and concentrated in vacuo. The residue was purified by prep-HPLC [Instrument: GX-B; Column: Welch Ultimate AQ-C18 150×30 mm; particle size: 5 μm; Mobile phase: 23-53% acetonitrile in $H_2O$ (add 0.1% TFA, v/v)]. The resulting solid was dissolved in 0.2 N hydrochloric acid and again lyophilized to give:

Compound (R)-8 (60 mg, 57% yield) as a white solid: cSFC analytical (D) tR=2.091 min., purity: 97.28%; LCMS (FF): tR=2.416 min., ($ES^+$) m/z $(M+H)^+$=324.1; $^1$H-NMR ($CD_3OD$, 400 MHz): δ 7.93-7.90 (m, 1H), 7.28-7.23 (t, J=9.2 Hz, 1H), 3.95 (s, 1H), 3.75-3.67 (m, 2H), 3.38-3.37 (m, 2H), 2.44-2.38 (m, 2H), 2.20-2.13 (m, 2H), 1.99-1.95 (m, 1H), 1.81 (s, 3H), 1.54 (s, 3H).

Example 9: (R)—N-(2,2-dimethylquinuclidin-3-yl)-5-fluoro-6-methylbenzo[d]isoxazol-3-amine hydrochloride ((R)-9)

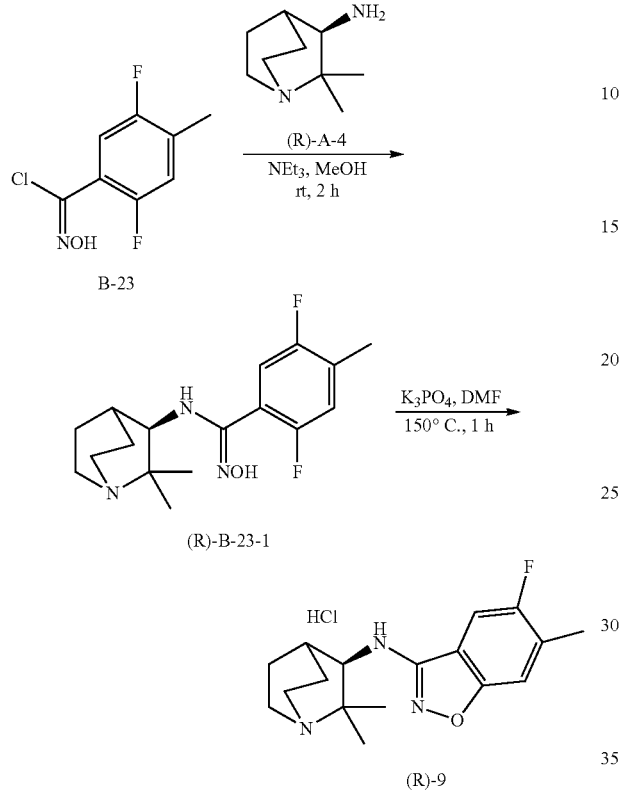

Following general procedure B1, compound (R)-9 was prepared from compound B-23:

Compound (R)-B-23-1 (0.15 g, white solid, 8% yield over 2 steps) was prepared from compound B-23 (0.9 g, 4.4 mmol) and (R)-A-4 (0.67 g, 4.38 mmol) with a reaction time of 2 hours. The product was purified by prep-HPLC [Instrument: GX-B; Column: Phenomenex Gemini C18 150×30 mm; particle size: 10 μm; Mobile phase: 10-40% acetonitrile in H$_2$O (add 0.1% TFA-ACN, v/v)]. LCMS (J): (ES$^+$) m/z (M+H)$^+$=324.3, tR=0.93.

A mixture of compound (R)-B-23-1 (0.12 g, 0.37 mmol) and potassium phosphate (0.24 g, 1.11 mmol) in N,N-dimethylformamide (5 mL) was stirred at 150° C. for 1 hour. On completion, the reaction mixture was filtered, concentrated in vacuo and purified by prep-HPLC [Instrument: GX-B; Column: Welch Ultimate AQ-C18 150×30 mm; particle size: 5 μm; Mobile phase: 20-40% acetonitrile in H$_2$O (add 0.1% TFA, v/v)]. The resulting solid was dissolved in 0.2 N hydrochloric acid and again lyophilized to give:

Compound (R)-9 (40 mg, 35% yield) as a white solid: cSFC analytical (M) tR=3.687 min., purity: 98.95%; LCMS (FF): tR=2.041 min., (ES$^+$) m/z (M+H)$^+$=304.2; $^1$H-NMR (CD$_3$OD, 400 MHz): δ 7.61 (d, J=9.2 Hz, 1H), 7.32 (d, J=6.4 Hz, 1H), 3.94 (s, 1H), 3.74-3.68 (m, 2H), 3.38-3.36 (m, 2H), 2.41-2.37 (m, 5H), 2.18-2.12 (m, 2H), 1.98-1.91 (m, 1H), 1.80 (s, 3H), 1.54 (s, 3H).

Example 10: (R)-6-chloro-N-(2,2-dimethylquinuclidin-3-yl)-7-methylbenzo[d]isoxazol-3-amine hydrochloride ((R)-10)

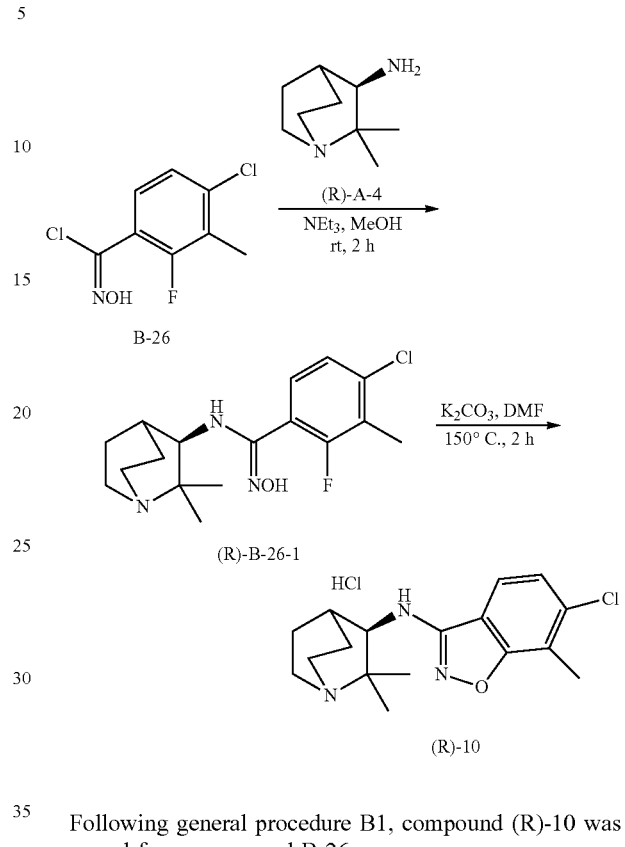

Following general procedure B1, compound (R)-10 was prepared from compound B-26:

Compound (R)-B-26-1 (0.12 g, white solid, 20% yield over 2 steps) was prepared from compound B-26 (0.3 g, 1.3 mmol) and (R)-A-4 (0.21 g, 1.3 mmol) with a reaction time of 2 hours. The product was purified by prep-HPLC [Instrument: GX-B; Column: Phenomenex Gemini C18 150×30 mm; particle size: 5 μm; Mobile phase: 40-44% acetonitrile in H$_2$O (add 0.1% TFA-ACN, v/v)]. LCMS (J): (ES$^+$) m/z (M+H)$^+$=340.1, tR=0.61.

A mixture of compound (R)-B-26-1 (0.12 g, 0.37 mmol) and potassium carbonate (0.15 g, 1.1 mmol) in N,N-dimethylformamide (2 mL) was stirred at 150° C. for 2 hours. On completion, the reaction mixture was filtered and concentrated in vacuo. The residue was purified by prep-HPLC [Instrument: GX-B; Column: Welch Ultimate AQ-C18 150×30 mm; particle size: 5 μm; Mobile phase: 36-66% acetonitrile in H$_2$O (add 0.1% TFA, v/v)]. The resulting solid was dissolved in 0.2 N hydrochloric acid and again lyophilized to give:

Compound (R)-10 (60 mg, 38% yield) as a white solid: cSFC analytical (D) tR=2.136 min., purity: 99.75%; LCMS (FF): tR=2.165 min., (ES$^+$) m/z (M+H)$^+$=320.1; $^1$H-NMR (CD$_3$OD, 400 MHz): δ 7.77 (d, J=8.0 Hz, 1H), 7.31 (d, J=8.4 Hz, 1H), 3.95 (s, 1H), 3.75-3.69 (m, 2H), 3.38-2.29 (m, 2H), 2.49 (s, 3H), 2.46-2.44 (m, 2H), 2.20-2.13 (m, 2H), 1.97-1.91 (m, 1H), 1.81 (s, 3H), 1.54 (s, 3H).

Example 11: (R)-6-chloro-N-(2,2-dimethylquinuclidin-3-yl)-5-fluorobenzo[d]isoxazol-3-amine hydrochloride ((R)-11)

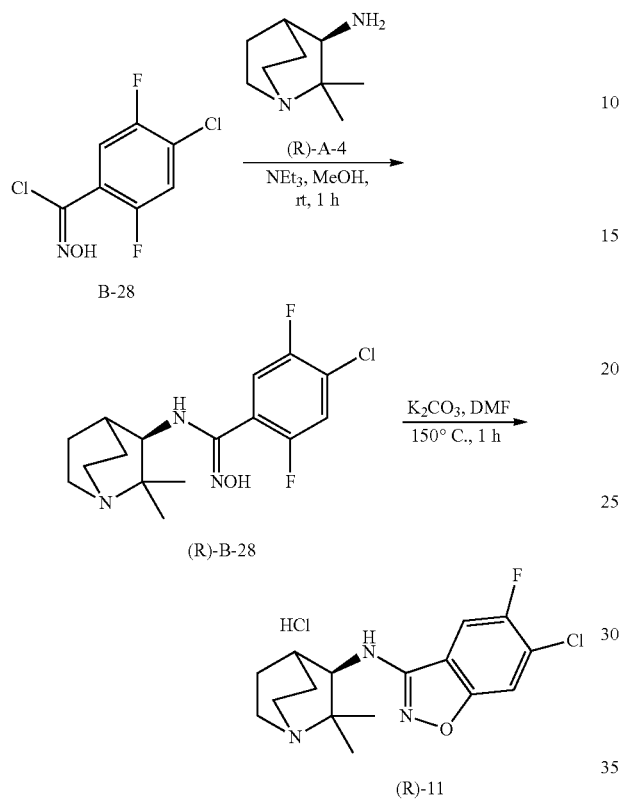

Following general procedure B1, compound (R)-11 was prepared from compound B-28:

Compound (R)-B-28-1 (0.30 g, white solid, 34% yield over two steps) was prepared from compound B-28 (0.60 g, 2.7 mmol) and (R)-A-4 (0.41 g, 2.7 mmol). The product was purified by prep-HPLC [Instrument: GX-A; Column: Phenomenex Gemini C18 250×50 mm, particle size: 10 m; Mobile phase: 33-63% acetonitrile in H₂O (add 0.05% NH₃ H2O, v/v)]. LCMS (J): tR=1.275 min., 344.1 m/z (M+1).

A solution of compound (R)-B-28-1 (0.25 g, 0.73 mmol) and potassium carbonate (0.20 g, 1.5 mmol) in N,N-dimethylformamide (3.0 mL) was stirred at 150° C. for 1 hour. On completion, the reaction mixture was filtered, concentrated in vacuo and purified by prep-HPLC [Instrument: GX-B; Column: Welch Ultimate AQ C18 150×30 mm, particle size: 5 μm; Mobile phase: 22-52% acetonitrile in H₂O (add 0.1% TFA-ACN, v/v)]. The resulting solid was dissolved in 0.2 N hydrochloric acid and again lyophilized to give:

Compound (R)-11 (100 mg, 38% yield) as a white solid: cSFC analytical (D) tR=3.058 min., chiral purity: 91%;

A solution of compound (R)-11 at 91% chiral purity (55 mg, 0.14 mmol) in 4 mL of methanol was purified by SFC (Instrument: SFC A; Column: AD-5 μm; Mobile phase: 50% methanol (0.01% NH₃ H2O) in CO₂) at room temperature and lyophilized. The resulting solids was dissolved in 0.2 M hydrochloric acid solution and again lyophilized to give:

Compound (R)-11 (25 mg, 49% yield) as a white solid: cSFC analytical (D) tR=2.036 min., purity: 100%; LCMS (GG): tR=2.10 min., (ES+) m/z (M+H)+=324.1; 1H-NMR (CD₃OD, 400 MHz): δ 7.89 (d, J=8.4 Hz, 1H), 7.67 (d, J=5.6 Hz, 1H), 3.94 (s, 1H), 3.75-3.68 (m, 2H), 3.35-3.28 (m, 2H), 2.45-2.38 (m, 2H), 2.19-2.13 (m, 2H), 1.96-1.90 (m, 1H), 1.78 (s, 3H), 1.52 (s, 3H).

Example 12: (R)-6-chloro-N-(2,2-dimethylquinuclidin-3-yl)-7-ethoxybenzo[d]isoxazol-3-amine hydrochloride ((R)-12)

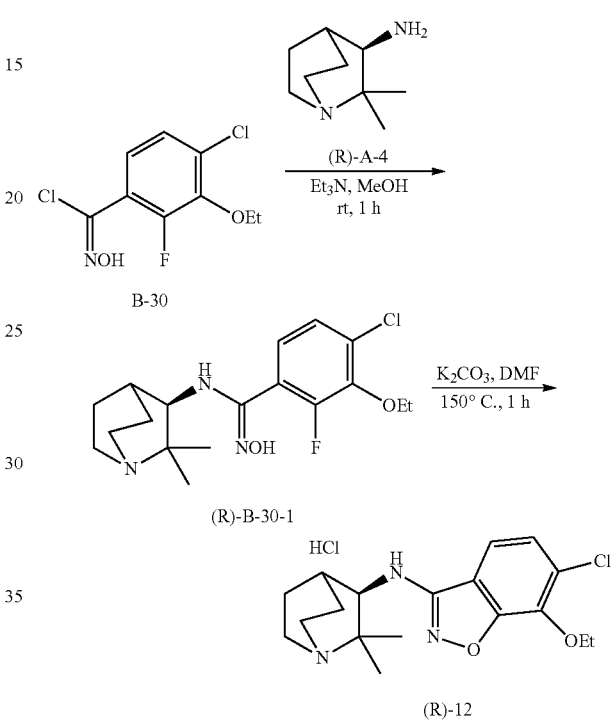

Following general procedure B1, compound (R)-12 was prepared from compound B-30:

Compound (R)-B-30-1 (0.20 g, white solid, 30% yield over two steps) was prepared from compound B-30 (0.49 g, 2.0 mmol) and (R)-A-4 (0.20 g, 1.3 mmol). The product was purified by prep-HPLC [Instrument: GX-A; Column: Phenomenex Gemini C18 250×50 mm, particle size: 10 m; Mobile phase: 35-55% acetonitrile in H₂O (add 0.5% NH₃.H2O, v/v)]. LCMS (J): (ES+) m/z (M+H)+=370.2, tR=1.226 min.

A solution of compound (R*R)—B-30-1 (0.18 g, 0.49 mmol) and potassium carbonate (0.13 g, 0.97 mmol) in N,N-dimethylformamide (8 mL) was stirred at 150° C. for 1 hour. On completion, the reaction mixture was filtered and concentrated in vacuo. The residue was purified by prep-HPLC [Instrument: GX-H; Column: Phenomenex Synergi C18 250×50 mm, particle size: 10 μm; Mobile phase: 50-80% acetonitrile in H₂O (add 0.5% NH₃ H2O, v/v)]. The resulting solids was dissolved in 0.2 M hydrochloric acid solution and again lyophilized to give:

Compound (R)-12 (70 mg, 37% yield) as a white solid: cSFC analytical (D) tR=2.167 min., purity: 94.10%; LCMS (GG): tR=2.175 min., (ES+) m/z (M+H)+=350.1; 1H-NMR (CD₃OD, 400 MHz): δ 7.57 (d, J=8 Hz, 1H), 7.30 (d, J=8.4 Hz, 1H), 4.48 (dd, J=14 Hz, J=7.2 Hz, 2H), 3.95 (s, 1H), 3.74-3.68 (m, 2H), 3.38-3.30 (m, 2H), 2.44-2.38 (m, 2H), 2.19-2.12 (m, 2H), 1.98-1.91 (m, 1H), 1.81 (s, 3H), 1.54 (s, 3H), 1.44 (t, J=6.8, 3H).

Example 13: (R)-7-chloro-N-(2,2-dimethylquinuclidin-3-yl)-6-methylbenzo[d]isoxazol-3-amine hydrochloride ((R)-13)

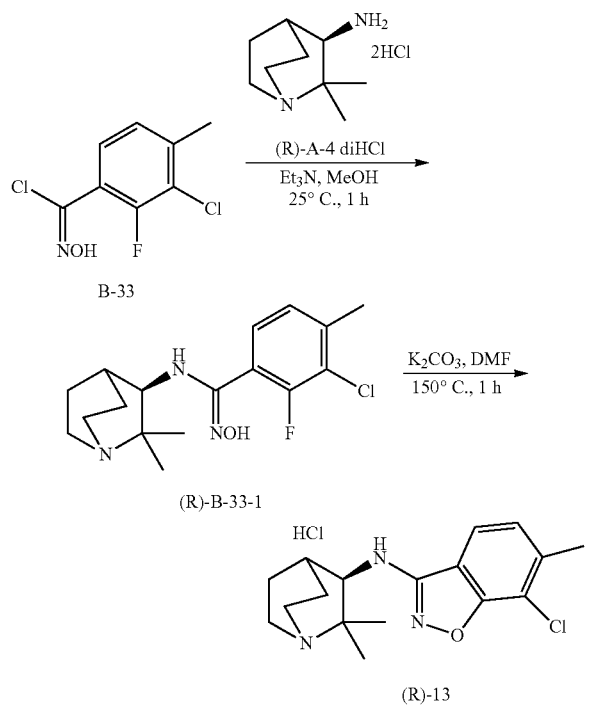

Following general procedure B1, compound (R)-13 was prepared from compound B-33:

Compound (R)-B-33-1 (0.50 g, white solid, 68% yield over two steps) was prepared from compound B-33 (0.45 g, 2.0 mmol) and compound (R)-A-4 dihydrochloride (0.46 g, 2.0 mmol) with 5 equivalent of triethyl amine. The product was purified by prep-HPLC [Instrument: HPLC-A; Column: Phenomenex Synergi C18 250×50 mm, particle size: 10 m; Mobile phase: 28-53% acetonitrile in H$_2$O (add 0.05% NH$_3$ H2O, v/v)]. LCMS (J): (ES$^+$) m/z (M+H)$^+$=340.1, tR=1.212 min.

A solution of compound (R)-B-33-1 (100 mg, 0.29 mmol) and potassium carbonate (0.12 g, 0.88 mmol) in N,N-dimethylformamide (2.0 mL) was stirred at 150° C. for 1 hour. On completion, the reaction mixture was filtered and concentrated in vacuo. The residue was purified by prep-HPLC [Instrument: GX-B; Column: Welch Ultimate AQ C18 150×30 mm, particle size: 4 m; Mobile phase: 28-58% acetonitrile in H$_2$O (add 0.1% TFA, v/v)]. The resulting solid was dissolved in 0.2 N hydrochloric acid and again lyophilized to give to give:

Compound (R)-13 (60 mg, 57% yield) as a white solid: cSFC analytical (D) tR=2.525 min., purity: 98.18%; LCMS (GG): tR=2.15 min., 320.2 m/z (M+1); 1H-NMR (CD$_3$OD, 400 MHz): δ 7.76 (d, J=8.0 Hz, 1H), 7.22 (d, J=8.0 Hz, 1H), 3.93 (s, 1H), 3.74-3.66 (m, 2H), 3.36-3.28 (m, 2H), 2.51 (s, 3H), 2.46-2.36 (m, 2H), 2.21-2.06 (m, 2H), 1.96-1.89 (m, 1H), 1.79 (s, 3H), 1.52 (s, 3H).

Example 14: (R)-6-chloro-N-(2,2-dimethylquinuclidin-3-yl)-7-(trifluoromethyl)benzo[d]isoxazol-3-amine hydrochloride ((R)-14)

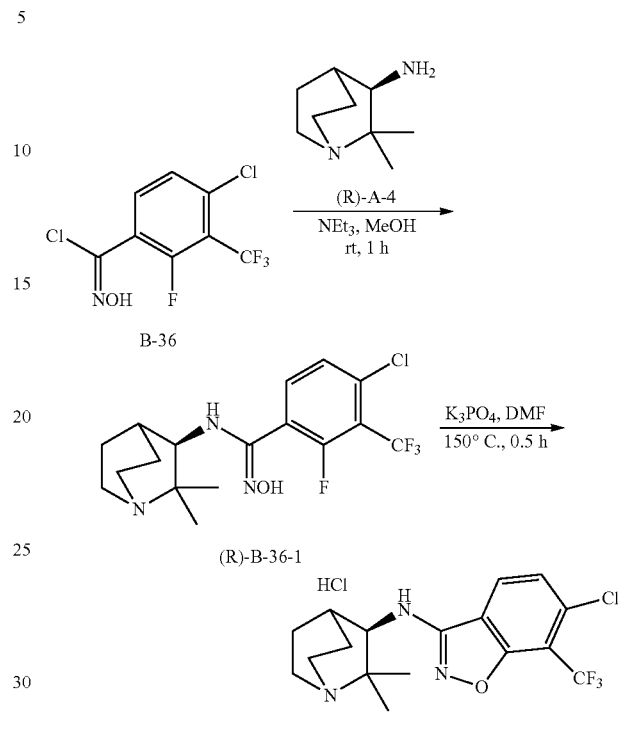

Following general procedure B1, compound (R)-14 was prepared from compound B-36:

Compound (R)-B-36-1 (0.15 g, yellow solid, 26% yield over 2 steps) was prepared from compound B-36 (0.45 g, 1.6 mmol) and (R)-A-4 (0.25 g, 1.6 mmol). The product was purified by prep-HPLC [Instrument: GX-C; Column: Phenomenex Gemini C18 250×50 mm; particle size: 10 μm; Mobile phase: 37-67% acetonitrile in H$_2$O (add 0.05% NH$_3$ H2O, v/v)]. LCMS (J): (ES$^+$) m/z (M+H)$^+$=394.1, tR=1.406.

A mixture of compound (R)-B-36-1 (0.12 g, 0.30 mmol) and potassium phosphate (0.19 g, 0.91 mmol) in N,N-dimethylformamide (20 mL) was stirred at 150° C. for 0.5 hour. On completion, the reaction mixture was filtered and concentrated in vacuo. The residue was purified by prep-HPLC [Instrument: GX-B; Column: Welch Ultimate AQ C18 150×30 mm; particle size: 5 μm; Mobile phase: 30-60% acetonitrile in H$_2$O (add 0.1% TFA, v/v)]. The resulting solid was dissolved in 0.2 N hydrochloric acid and again lyophilized to give:

Compound (R)-14 (80 mg, 64% yield) as a white solid: cSFC analytical (N) tR=3.292 min., purity: 98.02%; LCMS (GG): tR=2.291 min., (ES$^+$) m/z (M+H)$^+$=374.1; $^1$H-NMR (CD$_3$OD, 400 MHz): δ 8.19 (d, J=8.4 Hz, 1H), 7.55 (d, J=8.4 Hz, 1H), 3.97 (s, 1H), 3.75-3.70 (m, 2H), 3.39-3.37 (m, 2H), 2.45-2.40 (m, 2H), 2.20-2.13 (m, 2H), 1.99-1.96 (m, 1H), 1.82 (s, 3H), 1.54 (s, 3H).

Example 15: (R)-6-chloro-N-(2,2-dimethylquinuclidin-3-yl)-7-isopropoxybenzo[d]isoxazol-3-amine hydrochloride ((R)-15)

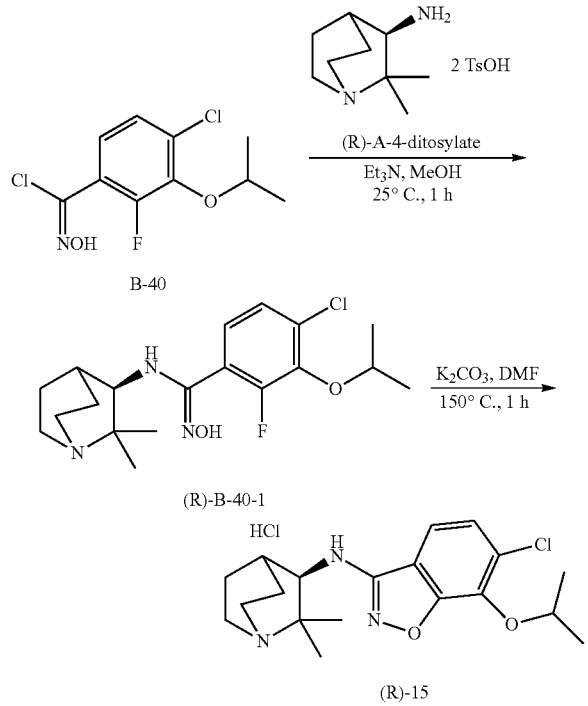

Following general procedure B1, compound (R)-15 was prepared from compound B-40:

Compound (R)-B-40-1 (0.20 g, white solid, 28% yield over two steps) was prepared from compound B-40 (0.50 g, 1.9 mmol) and (R)-A-4 ditosylate (0.94 g, 1.9 mmol) using 4 equivalents of triethylamine. The product was purified by prep-HPLC [Instrument: GX-H; Column: Boston pH-lex 150×25, particle size: 10 μm; Mobile phase: 40-70% water (0.05% $NH_3 \cdot H_2O$)-ACN. LCMS (J): ($ES^+$) m/z $(M+H)^+$ =384.1, tR=1.355 min.

A mixture of compound (R)-B-40-1(0.20 g, 0.52 mmol) and potassium carbonate (0.22 g, 1.6 mmol) in N,N-dimethylformamide (5.0 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150×30 mm; particle size 5 um; Mobile phase: 40-70% acetonitrile in water (0.1% TFA)-CAN]. The resulting solids were dissolved in 0.2 M hydrochloric acid solution and again lyophilized to give:

Compound (R)-15 (0.15 g, 79% yield) as a white solid: cSFC analytical (D) tR=2.089 min., purity: 100%; LCMS (GG): tR=2.279 min., 364.2 m/z (M+1); 1H-NMR (MeOD, 400 MHz): δ 7.59-7.55 (m, 1H), 7.31 (d, J=8.0 Hz, 1H), 5.00-4.89 (m, 1H), 3.94 (s, 1H), 3.75-3.69 (m, 2H), 3.38-3.30 (m, 2H), 2.43-2.38 (m, 2H), 2.19-2.11 (m, 2H), 1.95-1.94 (m, 1H), 1.81 (s, 3H), 1.54 (s, 3H). 1.39 (d, J=6.0 Hz, 6H)

Example 16: Preparation of 6-chloro-N-(1'-azaspiro[cyclopropane-1,2'-bicyclo[2.2.2]octan]-3'-yl)benzo[d]isoxazol-3-amine hydrochloride (rac-16)

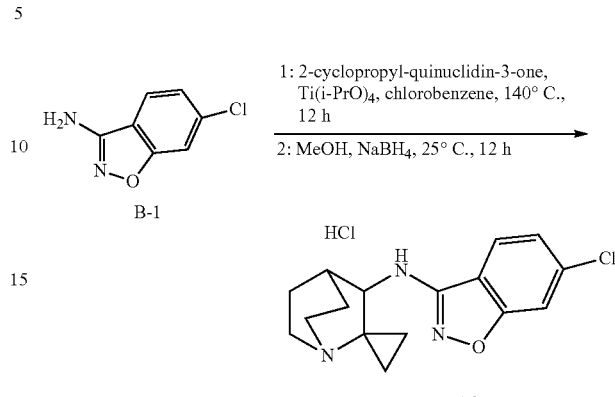

To a solution of compound B-1 (0.10 g, 0.6 mmol) and 2-cyclopropyl-quinuclidin-3-one (0.18 g, 1.2 mmol) in chlorobenzene (10 mL) at 25° C. was added portion-wise titanium(IV) isopropoxide (1.7 g, 6.0 mmol). The resulting solution was stirred at 140° C. for 12 hours. On completion, the mixture was cooled to 0° C., and methanol (2.0 mL) was added, followed by sodium borohydride (0.23 g, 6.0 mmol) in portions. The reaction was stirred at 25° C. for 12 hours, then quenched with saturated aqueous potassium carbonate solution, resulting in the formation of a solid. The mixture was filtered, and the filtrate was extracted with dichloromethane (3×10 mL). The combined organic layers were washed with brine, dried over anhydrous sodium sulfate, filtered and concentrated in vacuo. The residue was purified by prep-HPLC [Instrument: GX-I; Column: Xtimate C18 150×25 mm, particle size: 5 μm; Mobile phase: 20-50% acetonitrile in $H_2O$ (add 0.1% TFA, v/v)]. The resulting solid was dissolved in 0.2 N hydrochloric acid and again lyophilized to give rac-16 (5.1 mg, 2.8% yield) as a white solid. LCMS (B): tR=0.670 min., ($ES^+$) m/z $(M+H)^+$=304.1. 1H-NMR ($CD_3OD$, 400 MHz): δ 7.88 (d, J=8.4 Hz, 1H), 7.50 (s, 1H), 7.32-7.29 (m, 1H), 4.19-4.18 (m, 1H), 3.54-3.45 (m, 2H), 3.43-3.39 (m, 2H), 2.62-2.61 (m, 1H), 2.31 (m, 1H), 2.20-2.16 (m, 2H), 1.94 (m, 1H), 1.36-1.35 (m, 2H), 1.20-1.19 (m, 2H).

Preparation of (R)-6-chloro-N-(1'-azaspiro[cyclopropane-1,2'-bicyclo[2.2.2]octan]-3'-yl)benzo[d]isoxazol-3-amine ((R)-16)

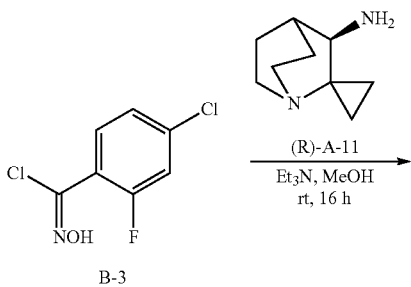

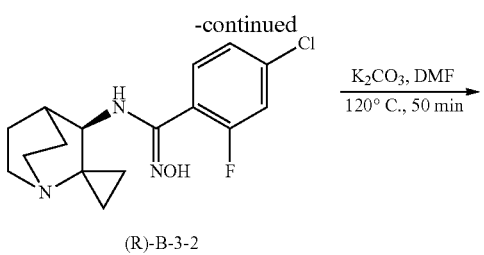

(R)-B-3-2

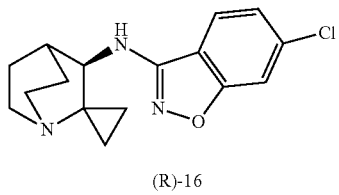

(R)-16

To a solution of (R)-A-11 (400 mg, 2.6 mmol) and triethylamine (332 mg, 3.3 mmol) in methanol (10 mL) at room temperature was added a solution of compound B-3 (574 mg, 2.8 mmol) in methanol (18 mL) over 4 hours using a syringe pump. The mixture was stirred for an additional 12 hours, concentrated, taken up in chloroform, washed with aqueous sodium carbonate and concentrated. The residue was purified by silica gel column chromatography [chloroform: methanol=1:0 to 9:1] to afford compound (R)-B-3-2 (528 mg, 62% yield) as a white solid. LCMS (1): tR=3.036 min., (ES$^+$)m/z (M+H)$^+$=324.2.

To a solution of compound (R)-B-3-2 (498 mg, 1.5 mmol) in N,N-dimethylformamide (10 mL) under argon atmosphere was added potassium carbonate (425 mg, 3.1 mmol). The mixture was heated at 120° C. for 50 minutes. The solution was put on an SCX column and eluted with methanol. The product was eluted from the column using 3.5 M ammonia in methanol, concentrated and purified by silica gel column chromatography [chloroform: methanol=1:0 to 9:1]. The resulting product was further purified by preparative HPLC (1) to give compound (R)-16 (285 mg, 61% yield) as a white solid after lyophilization: cHPLC analytical [Column: Chiralcel OD-H, 250×4.6 mm, particle size: 5 μm; Flow: 1.0 mL/min; Column temp: 25° C.; Eluent: 0.1% diethylamine in Heptane/Ethanol=9/1; detection: DAD (220-320 nm)] tR=4.542 min., purity: 97%; LCMS (1): tR=3.412 min., (ES$^+$) m/z (M+H)$^+$=304.1; 1H NMR (300 MHz, Chloroform-d) δ 7.47-7.38 (m, 2H), 7.24-7.18 (m, 1H), 4.25 (d, J=8.1 Hz, 1H), 3.87-3.77 (m, 1H), 3.13-2.75 (m, 4H), 2.45-2.36 (m, 1H), 1.85-1.70 (m, 3H), 1.53-1.37 (m, 1H), 1.02-0.90 (m, 1H), 0.90-0.78 (m, 1H), 0.74-0.63 (m, 2H).

Chiral Purification:

Compound (R)-16 (280 mg, 0.90 mmol, 97% chiral purity) in heptane/ethanol was purified by preparative chiral HPLC (Column: Chiralcel OD, 250×20 mm, particle size: 10 μm; Flow: 18 mL/min; Column temp: 25° C.; Eluent: 0.2% diethylamine in Heptane/Ethanol=9/1; detection: DAD (220-320 nm)). The collected fractions were concentrated at room temperature, taken up in methanol and purified by SCX chromatography. The resulting product was lyophilized to give compound (R)-16 (249 mg, 89%) as a white solid: cHPLC analytical tR=4.532 min., purity: 100%.

(R)-16 was also prepared by dissolving the freebase form of compound (R)-16 in 0.2 M hydrochloric acid solution and lyophilized to give:

Compound (R)-16 hydrochloride as a white solid: cSFC analytical (D) tR=2.037 min., purity: 100%; LCMS (GG): tR=2.019 min., (ES+) m/z (M+H)+=304.1; 1H-NMR (CD$_3$OD, 400 MHz): δ 7.94 (d, J=8.4 Hz, 1H), 7.48 (s, 1H), 7.29 (dd, J=8.4 Hz, J=1.6 Hz, 1H), 4.19 (d, J=2.4 Hz, 1H), 3.71-3.31 (m, 4H), 2.63-2.61 (m, 2H), 2.43-2.36 (m, 2H), 2.16-2.07 (m, 2H), 1.96-1.90 (m, 1H), 1.78 (s, 3H), 1.52 (s, 3H).

Preparation of (S)-6-chloro-N-(1'-azaspiro[cyclopropane-1,2'-bicyclo[2.2.2]octan]-3'-yl)benzo[d]isoxazol-3-amine ((S)-16)

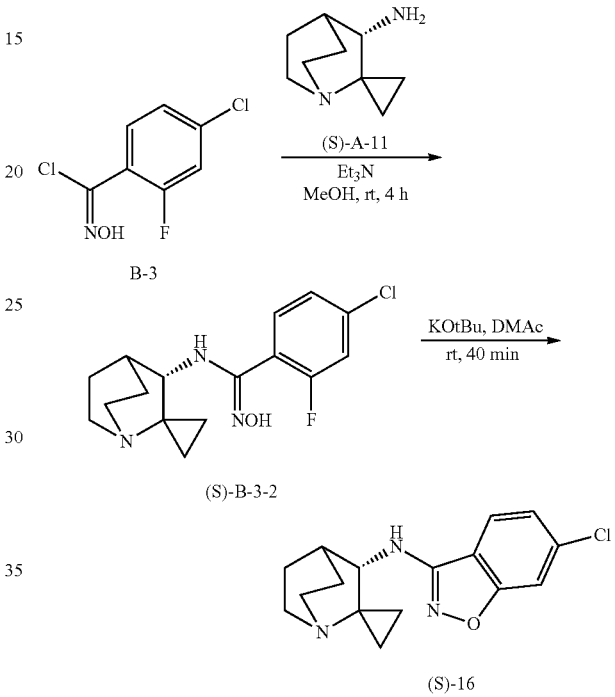

To a solution of (S)-A-11 (43 mg, 0.3 mmol) and triethylamine (29 mg, 0.3 mmol) in methanol (3 mL) at room temperature was added a solution of compound B-3 (59 mg, 0.3 mmol) in methanol (2.4 mL) over 4 hours using a syringe pump. Upon complete addition, the mixture was filtered, concentrated, taken up in chloroform, washed with aqueous potassium carbonate and concentrated. The residue was purified by silica gel column chromatography [chloroform: methanol=1:0 to 9:1] to afford compound (S)—B-3-2 (51 mg, 55% yield) as a white solid. LCMS (1): tR=3.021 min., (ES$^+$) m/z (M+H)$^+$=324.0.

To a solution of compound (S)—B-3-2 (57 mg, 0.2 mmol) in N,N-dimethylacetamide (3 mL) was added potassium tertbutoxide (40 mg, 0.4 mmol). The mixture was stirred at room temperature for 40 minutes. The solution was put on an SCX column and eluted with methanol. The product was eluted from the column using 3.5 M ammonia in methanol, concentrated and purified by preparative HPLC (1) to give compound (S)-16 (17 mg, 32% yield) as a white solid after lyophilization: cHPLC analytical [Column: Chiralcel OD-H, 250×4.6 mm, particle size: 5 μm; Flow: 1.0 mL/min; Column temp: 25° C.; Eluent: 0.1% diethylamine in Heptane/Ethanol=9/1; detection: DAD (220-320 nm)] tR=11.159 min., purity: 97%; LCMS (1): tR=3.402 min., (ES$^+$) m/z (M+H)$^+$=304.2; 1H NMR (300 MHz, Chloroform-d) δ 7.47-7.37 (m, 2H), 7.23-7.18 (m, 1H), 4.25 (d, J=8.6 Hz, 1H, exchange with D2O), 3.87-3.77 (m, 1H), 3.14-2.74 (m, 4H), 2.46-2.37 (m, 1H), 1.86-1.64 (m, 3H), 1.53-1.37 (m, 1H), 1.02-0.91 (m, 1H), 0.91-0.79 (m, 1H), 0.74-0.62 (m, 2H).

Example 17: (R)-6-chloro-7-fluoro-N-(1'-azaspiro [cyclopropane-1,2'-bicyclo[2.2.2]octan]-3'-yl)benzo [d]isoxazol-3-amine hydrochloride ((R)-17)

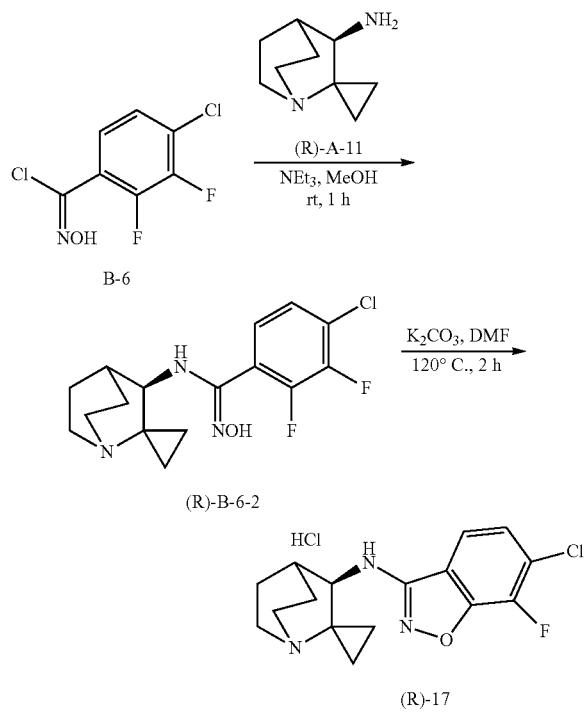

Following general procedure B1, compound (R)-17 was prepared from compound B-6:

Compound (R)-B-6-2 (70 mg, yellow solid, crude) was prepared from compound B-6 (50 mg, 0.22 mmol) and (R)-A-11 (34 mg, 0.22 mmol). The product was used for the next step without further purification. LCMS (J): (ES⁺) m/z (M+H)⁺=342.1, tR=1.163.

A mixture of compound (R)-B-6-2 (70 mg, 0.20 mmol) and potassium carbonate (85 mg, 0.60 mmol) in N,N-dimethylformamide (3.0 mL) was stirred at 120° C. for 2 hours. On completion, the reaction mixture was filtered, concentrated in vacuo and purified by prep-HPLC [Instrument: GX-I; Column: Xtimate C18 150×25 mm, particle size: 5 µm; Mobile phase: 20-50% acetonitrile in H₂O (add 0.1% TFA, v/v)]. The resulting solid was dissolved in 0.2 N hydrochloric acid and again lyophilized to give:

Compound (R)-17 (15 mg, 20% yield) as a white solid: cSFC analytical tR=1.90 min., purity: 98.10%; LCMS (FF): tR=2.40 min., 322.1 m/z (M+1); 1H-NMR (CD₃OD, 400 MHz): δ 7.75-7.72 (d, J=8.4 Hz 1H), 7.38-7.34 (m, 1H), 4.21-4.20 (m, 1H), 3.71-3.54 (m, 2H), 3.52-3.39 (m, 2H), 2.65-2.63 (m, 1H), 2.35-2.29 (m, 1H), 2.21-2.17 (m, 2H), 2.00-1.93 (m, 1H), 1.45-1.33 (m, 2H), 1.30-1.19 (m, 2H).

Example 18: (R)-6-methoxy-N-(1'-azaspiro[cyclopropane-1,2'-bicyclo[2.2.2]octan]-3'-yl)benzo[d] isoxazol-3-amine hydrochloride ((R)-18)

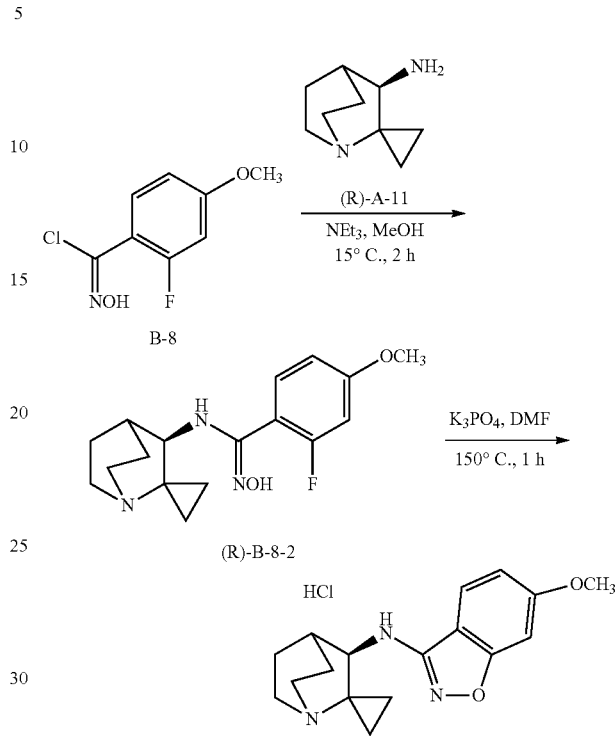

Following general procedure B1, compound (R)-18 was prepared from compound B-8:

Compound (R)-B-8-2 (0.21 g, white solid, 33% yield) was prepared from compound B-8 (0.40 g, 2.0 mmol), triethylamine (0.40 g, 3.9 mmol) and (R)-A-11 (0.30 g, 2.0 mmol) with a reaction time of 2 hours. The product was purified by prep-HPLC [Instrument: GX-A; Column: Phenomenex Gemini C18 250×50 mm, particle size: 10 µm; Mobile phase: 19-49% acetonitrile in H₂O (add 0.05% NH₃ H2O, v/v)]. 1H-NMR (CDCl₃, 400 MHz): δ 7.19 (t, J=8.2 Hz, 1H), 6.80-6.73 (m, 2H), 3.81 (s, 3H), 3.11-3.05 (m, 2H), 2.86-2.79 (m, 2H), 2.74-2.70 (m, 1H), 1.92 (m, 1H), 1.74-1.64 (m, 2H), 1.51-1.42 (m, 2H), 1.00-0.96 (m, 1H), 0.77-0.73 (m, 1H), 0.64-0.60 (m, 1H), 0.32 (m, 1H).

A mixture of compound (R)-B-8-2 (0.10 g, 0.31 mmol) and potassium phosphate (199 mg, 0.94 mmol) in N,N-dimethylformamide (4 mL) was degassed and purged with nitrogen 3 times at 15° C., and then stirred at 150° C. for 1 hour under nitrogen atmosphere. The reaction mixture was filtered, concentrated in vacuo and purified by prep-HPLC [Instrument: GX-B; Column: Phenomenex Synergi C18 150×30 mm, particle size: 4 µm; Mobile phase: 18-48% acetonitrile in H₂O (add 0.1% TFA, v/v)]. The resulting solid was dissolved in 0.2 M hydrochloric acid and lyophilized to give:

Compound (R)-18 (48 mg, 46% yield) as a white solid: cSFC analytical (D) tR=2.39 min., purity: 100%; LCMS (FF): tR=2.053 min., (ES⁺) m/z (M+H)⁺=300.1; 1H-NMR (CD₃OD, 400 MHz): δ 7.78 (d, J=8.8 Hz, 1H), 6.93 (s, 1H), 6.88 (d, J=8.8 Hz, 1H), 4.15 (s, 1H), 3.86 (s, 3H), 3.68-3.55 (m, 1H), 3.50-3.46 (m, 1H), 3.46-3.38 (m, 2H), 2.60 (d, J=2.4 Hz, 1H), 2.36-2.30 (m, 1H), 2.20-2.17 (m, 2H), 1.99-1.95 (m, 1H), 1.41-1.36 (m, 2H), 1.27-1.19 (m, 2H).

Example 19: (R)-6,7-dichloro-N-(1'-azaspiro[cyclopropane-1,2'-bicyclo[2.2.2]octan]-3'-yl)benzo[d]isoxazol-3-amine hydrochloride ((R)-19)

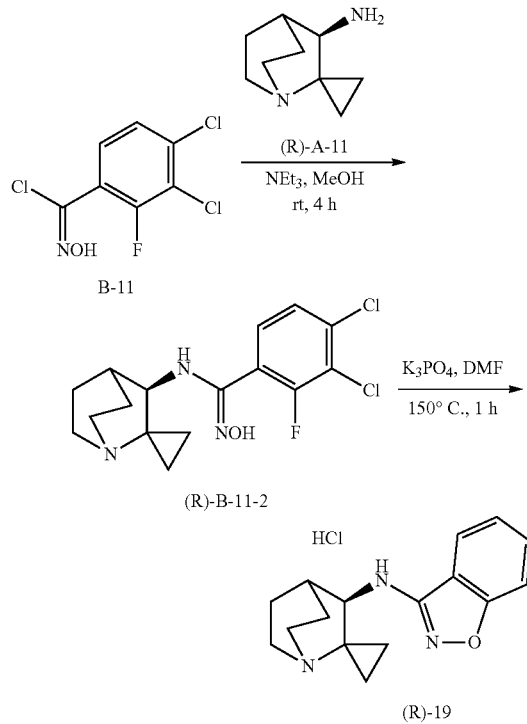

Following general procedure B1, compound (R)-19 was prepared from compound B-11:

Compound (R)-B-11-2 (96 mg, white solid, 43% yield) was prepared from compound B-11 (0.15 g, 0.62 mmol) and (R)-A-11 (94 mg, 0.62 mmol) with a reaction time of 4 hours. The product was purified by prep-HPLC [Instrument: GX-A; Column: Phenomenex Gemini C18 250×50 mm, particle size: 10 μm; Mobile phase: 32-62% acetonitrile in $H_2O$ (add 0.05% ammonia-ACN, v/v)]. LCMS (J): (ES$^+$) m/z (M+H)$^+$=358.1, tR=1.30.

A solution of compound (R)-B-11-2 (60 mg, 0.17 mmol) and potassium phosphate (70 mg, 0.5 mmol) in N,N-dimethylformamide (3.0 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150×30 mm, particle size: 5 μm; Mobile phase: 30-60% acetonitrile in $H_2O$ (add 0.1% TFA-ACN, v/v)]. The resulting solid was dissolved in 0.2 N hydrochloric acid and again lyophilized to give:

(R)-6,7-dichloro-N-(1'-azaspiro[cyclopropane-1,2'-bicyclo[2.2.2]octan]-3'-yl)benzo[d]isoxazol-3-amine hydrochloride compound (R)-19 (20 mg, 35% yield) as a white solid: cSFC analytical(D) tR=2.28 min., purity: 99.25%; LCMS (FF): tR=2.41 min., 338.0 m/z (M+1); 1H-NMR (CD$_3$OD, 400 MHz): δ 7.86 (d, J=8.4 Hz, 1H), 7.48 (d, J=8.8 Hz, 1H), 4.23 (m, 1H), 3.66-3.58 (m, 2H), 3.51-3.42 (m, 2H), 2.66-2.65 (m, 1H), 2.37-2.31 (m, 1H), 2.24-2.20 (m, 2H), 2.03-1.97 (m, 1H), 1.44-1.40 (m, 2H), 1.28-1.22 (m, 2H).

Example 20: (R)-6-chloro-7-methoxy-N-(1'-azaspiro[cyclopropane-1,2'-bicyclo[2.2.2]octan]-3'-yl)benzo[d]isoxazol-3-amine hydrochloride ((R)-20)

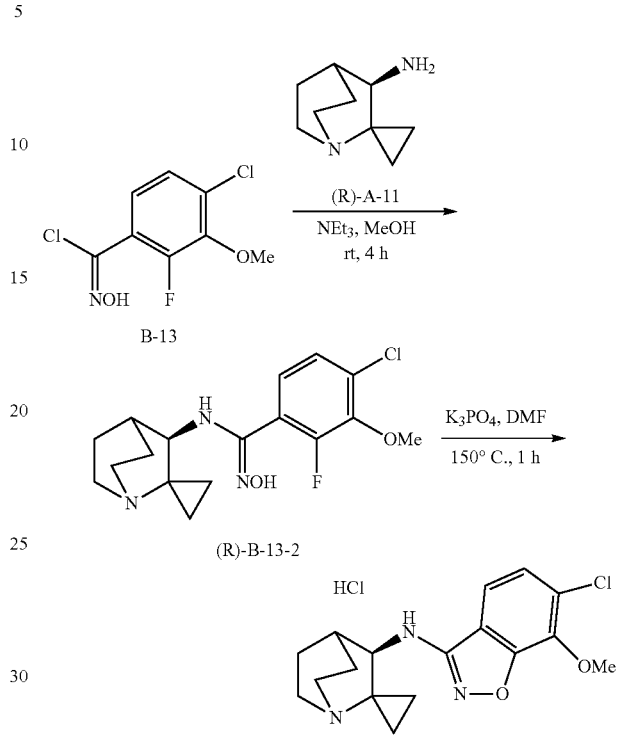

Following general procedure B1, compound (R)-20 was prepared from compound B-13:

Compound (R)-B-13-2 (75 mg, white solid, 17% yield) was prepared from compound B-13 (0.30 g, 1.3 mmol) and (R)-A-11 (0.19 g, 1.3 mmol) with a reaction time of 1 hour. The product was purified by prep-HPLC [Instrument: GX-C; Column: Phenomenex Gemini 250×50 mm, particle size: 10 μm; Mobile phase: 24-54% acetonitrile in $H_2O$ (add 0.5% NH$_3$ H2O, v/v)]. LCMS (J): (ES$^+$) m/z (M+H)$^+$=354.1, tR=1.17.

A solution of compound (R)-B-13-2 (50 mg, 0.14 mmol) and potassium phosphate (90 mg, 0.42 mmol) in N,N-dimethylformamide (1.5 mL) was stirred at 150° C. for 1 hour. On completion, the reaction mixture was filtered and concentrated in vacuo. The residue was purified by prep-HPLC [Instrument: GX-B; Column: Phenomenex Gemini C18 150×30 mm, particle size: 10 μm; Mobile phase: 37-67% acetonitrile in $H_2O$ (add 0.1% TFA-ACN, v/v)]. The resulting solid was dissolved in 0.2 N hydrochloric acid and again lyophilized to give:

Compound (R)-20 (30 mg, 63% yield) as a white solid: cSFC analytical (D) tR=2.27 min., purity: 100%; LCMS (FF): tR=2.08 min., (ES$^+$) m/z (M+H)$^+$=334.1; 1H-NMR (CD$_3$OD, 400 MHz): δ 7.54 (d, J=8.0 Hz, 1H), 7.30 (d, J=8.4 Hz, 1H), 4.23-4.22 (m, 1H), 4.19 (s, 3H), 3.67-3.58 (m, 2H), 2.52-2.42 (m, 2H), 2.66-2.64 (m, 1H), 2.37-2.31 (m, 1H), 2.24-2.20 (m, 2H), 2.00-1.98 (m, 1H), 1.43-1.36 (m, 2H), 1.28-1.22 (m, 2H).

Example 21: (R)-6-methyl-N-(1'-azaspiro[cyclopropane-1,2'-bicyclo[2.2.2]octan]-3'-yl) benzo[d]isoxazol-3-amine hydrochloride ((R)-21)

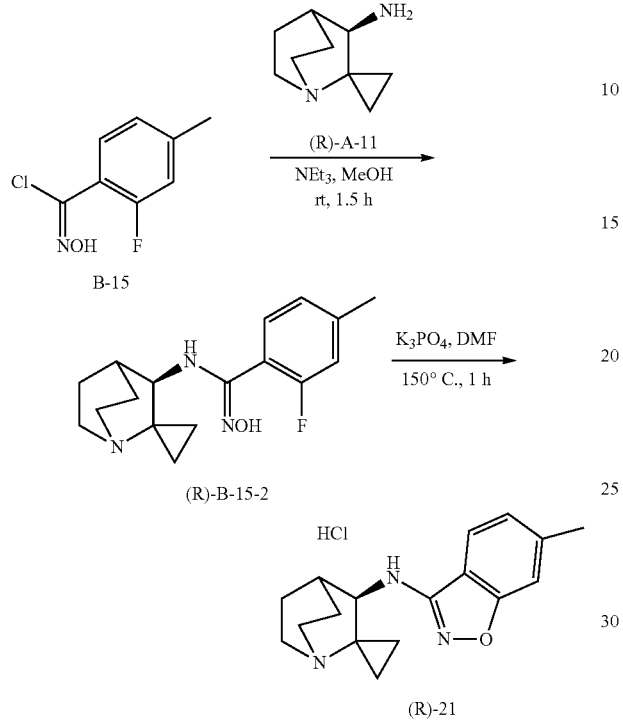

Example 22: (R)-7-fluoro-6-methyl-N-(1'-azaspiro[cyclopropane-1,2'-bicyclo[2.2.2]octan]-3'-yl)benzo[d]isoxazol-3-amine hydrochloride ((R)-22)

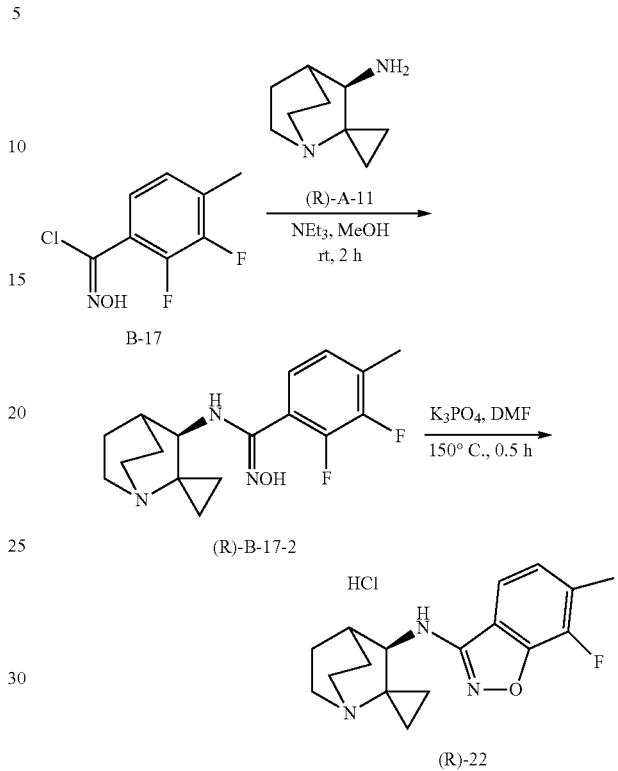

Following general procedure B1, compound (R)-21 was prepared from compound B-15:

Compound (R)-B-15-2 (200 mg, white solid, 25% yield) was prepared from compound B-15 (0.50 g, 2.67 mmol) and (R)-A-11 (0.41 g, 1.3 mmol) with a reaction time of 1.5 hours. The product was purified by prep-HPLC [Instrument: GX-C; Column: Phenomenex Gemini 250×50 mm, particle size: 10 μm; Mobile phase: 26-56% acetonitrile in $H_2O$ (add 0.5% $NH_3$ H2O, v/v)]. LCMS (J): ($ES^+$) m/z $(M+H)^+$=304.2, tR=1.10.

A solution of compound (R)-B-15-2 (120 mg, 0.21 mmol) and potassium phosphate (0.25 g, 1.19 mmol) in N,N-dimethylformamide (2 mL) was stirred at 150° C. for 1 hour. On completion, the reaction mixture was filtered, concentrated in vacuo and purified by prep-HPLC [Instrument: GX-C; Column: Phenomenex Gemini C18 250×50 mm, particle size: 10 m; Mobile phase: 33-63% acetonitrile in $H_2O$ (add 0.05% ammonia-ACN, v/v)]. The resulting solid was dissolved in 0.2 N hydrochloric acid and again lyophilized to give:

Compound (R)-21 (45 mg, 53% yield) as a white solid: cSFC analytical (D) tR=2.21 min., purity: 99.7%; LCMS (FF): tR=1.94 min., ($ES^+$) m/z $(M+H)^+$=284.2; 1H-NMR ($CD_3OD$, 400 MHz): δ 7.81 (d, J=8.4 Hz, 1H), 7.22 (s, 1H), 7.14 (d, J=8.4 Hz, 1H), 4.21-4.20 (m, 1H), 3.71-3.69 (m, 1H), 3.58-3.57 (m, 1H), 3.51-3.40 (m, 2H), 2.64-2.62 (m, 1H), 2.49 (s, 3H), 2.36-2.33 (m, 1H), 2.23-2.18 (m, 2H), 1.98-1.97 (m, 1H), 1.46-1.38 (m, 2H), 1.29-1.21 (m, 2H).

Following general procedure B1, compound (R)-22 was prepared from compound B-17:

Compound (R)-B-17-2 (0.20 g, white solid, 42% yield) was prepared from compound B-17 (0.30 g, 1.5 mmol) and (R)-A-11 (0.22 g, 1.5 mmol). The product was purified by prep-HPLC [Instrument: GX-H; Column: Phenomenex Gemini C18 250×50 mm; particle size: 10 μm; Mobile phase: 26-56% acetonitrile in $H_2O$ (add 0.05% $NH_3$ H2O, v/v)]. LCMS (J): ($ES^+$) m/z $(M+H)^+$=322.2, tR=1.181.

A mixture of compound (R)-B-17-2 (0.10 g, 0.29 mmol) and potassium phosphate (0.20 g, 0.87 mmol) in N,N-dimethylformamide (10 mL) was stirred at 150° C. for 0.5 hour. On completion, the reaction mixture was filtered and concentrated in vacuo. The residue was purified by prep-HPLC [Instrument: GX-B; Column: Xtimate C18 150×25 mm; particle size: 5 m; Mobile phase: 17-47% acetonitrile in $H_2O$ (add 0.1% TFA, v/v)]. The resulting solid was dissolved in 0.2 N hydrochloric acid and again lyophilized to give:

Compound (R)-22 (55 mg, 52% yield) as a white solid: cSFC analytical (D) tR=1.994 min., purity: 98.53%; LCMS (FF): tR=2.371 min., ($ES^+$) m/z $(M+H)^+$=302.1; $^1$H-NMR ($CD_3OD$, 400 MHz): δ 7.60-7.58 (d, J=8.4 Hz, 1H), 7.18-7.14 (m, 1H), 4.22 (d, J=2.4 Hz, 1H), 3.68-3.58 (m, 2H), 3.52-3.44 (m, 2H), 2.66-2.64 (m, 1H), 2.43-2.42 (d, J=2.0 Hz, 3H), 2.38-2.31 (m, 1H), 2.23-2.20 (m, 1H), 2.00-1.94 (m, 1H), 1.43-1.34 (m, 2H), 1.27-1.21 (m, 2H).

Example 23: (R)-7-chloro-6-fluoro-N-(1'-azaspiro[cyclopropane-1,2'-bicyclo[2.2.2]octan]-3'-yl)benzo[d]isoxazol-3-amine hydrochloride ((R)-23)

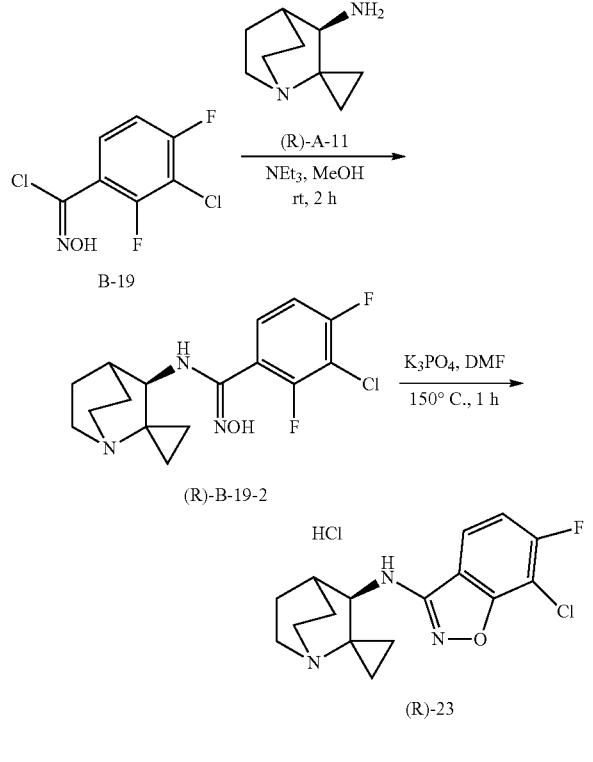

Example 24: (R)-5-fluoro-6-methyl-N-(1'-azaspiro[cyclopropane-1,2'-bicyclo[2.2.2]octan]-3'-yl) benzo[d]isoxazol-3-amine hydrochloride ((R)-24)

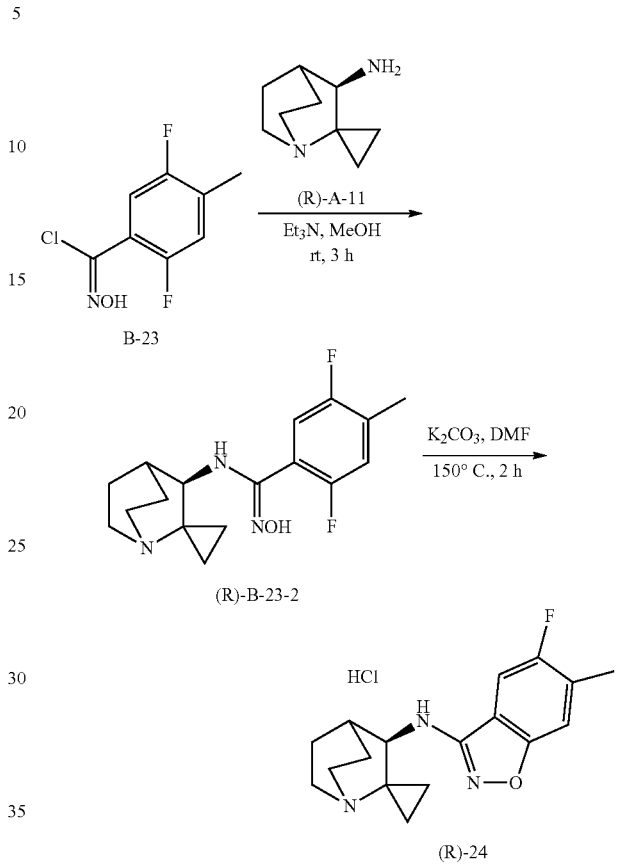

Following general procedure B1, compound (R)-23 was prepared from compound B-19:

Compound (R)-B-19-2 (0.21 g, yellow solid, 31% yield over 2 steps) was prepared from compound B-19 (0.45 g, 2.0 mmol) and (R)-A-11 (0.30 g, 2.0 mmol) with a reaction time of 2 hours. The product was purified by prep-HPLC [Instrument: GX-H; Column: Phenomenex Gemini C18 250×50 mm; particle size: 10 μm; Mobile phase: 24-54% acetonitrile in $H_2O$ (add 0.05% $NH_3$ H2O, v/v)]. LCMS (J): $(ES^+)$ m/z $(M+H)^+$=342.1, tR=1.183.

A mixture of compound (R)-B-19-2 (0.20 g, 0.59 mmol) and potassium phosphate (0.37 g, 1.8 mmol) in N,N-dimethylformamide (20 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150×30 mm; particle size: 5 m; Mobile phase: 22-52% acetonitrile in $H_2O$ (add 0.1% TFA, v/v)]. The resulting solid was dissolved in 0.2 N hydrochloric acid and again lyophilized to give:

Compound (R)-23 (50 mg, 24% yield) as a white solid: cSFC analytical (D) tR=1.835 min., purity: 98.24%; LCMS (GG): tR=2.096 min., $(ES^+)$ m/z $(M+H)^+$=322.1; $^1$H-NMR ($CD_3OD$, 400 MHz): δ 7.90 (dd, J=8.8 Hz, J=2.4 Hz, 1H), 7.25 (t, J=8.8 Hz, 1H), 4.22 (d, J=2.4 Hz, 1H), 3.70-3.50 (m, 2H), 3.49-3.44 (m, 2H), 2.66-2.64 (m, 1H), 2.43-2.42 (d, J=2.0 Hz, 3H), 2.38-2.31 (m, 1H), 2.23-2.19 (m, 2H), 2.01-1.98 (m, 1H), 1.44-1.37 (m, 2H), 1.28-1.23 (m, 2H).

Following general procedure B1, compound (R)-24 was prepared from compound B-23:

Compound (R)-B-23-2 (0.15 g, white solid, 40% yield over two steps) was prepared from compound B-23 (0.20 g, 0.97 mmol) and (R)-A-11 (0.15 g, 0.97 mmol) with a reaction of 3 hours. The product was purified by prep-HPLC [Instrument: GX-A; Column: Phenomenex Gemini C18 250×50 mm, particle size: 10 μm; Mobile phase: 28-58% acetonitrile in $H_2O$ (add 0.05% ammonia, v/v)]. LCMS (J): $(ES^+)$ m/z $(M+H)^+$=322.2, tR=1.67 min.

A solution of compound (R)-B-23-2 (0.15 g, 0.47 mmol) and potassium carbonate (0.19 g, 1.4 mmol) in N,N-dimethylformamide (6.0 mL) was stirred at 150° C. for 2 hours. On completion, the reaction mixture was filtered and concentrated in vacuo. The residue was purified by prep-HPLC [Instrument: GX-h; Column: Phenomenex Gemini C18 250×50 mm, particle size: 10 m; Mobile phase: 33-63% acetonitrile in $H_2O$ (add 0.05% TFA, v/v)]. The resulting solids was dissolved in 0.2 M hydrochloric acid solution and again lyophilized to give:

Compound (R)-24 (30 mg, 20% yield) as a white solid: cSFC analytical (D) tR=1.804 min., purity: 99.49%; LCMS (EE): tR=2.03 min., 302.2 m/z (M+1); 1H-NMR ($CD_3OD$, 400 MHz): δ 7.47 (d, J=8.4 Hz, 1H), 7.19 (d, J=6.4 Hz, 1H), 4.09-4.08 (m, 1H), 3.56-3.45 (m, 2H), 3.40-3.31 (m, 2H), 2.52-2.51 (m, 1H), 2.29-2.19 (m, 4H), 2.11-2.07 (m, 2H), 1.90-1.85 (m, 1H), 1.33-1.26 (m, 2H), 1.15-1.11 (m, 2H).

Example 25: (R)-6-chloro-7-methyl-N-(1'-azaspiro[cyclopropane-1,2'-bicyclo[2.2.2]octan]-3'-yl)benzo[d]isoxazol-3-amine hydrochloride ((R)-25)

Example 26: (R)-6-chloro-5-fluoro-N-(1'-azaspiro[cyclopropane-1,2'-bicyclo[2.2.2]octan]-3'-yl)benzo[d]isoxazol-3-amine hydrochloride ((R)-26)

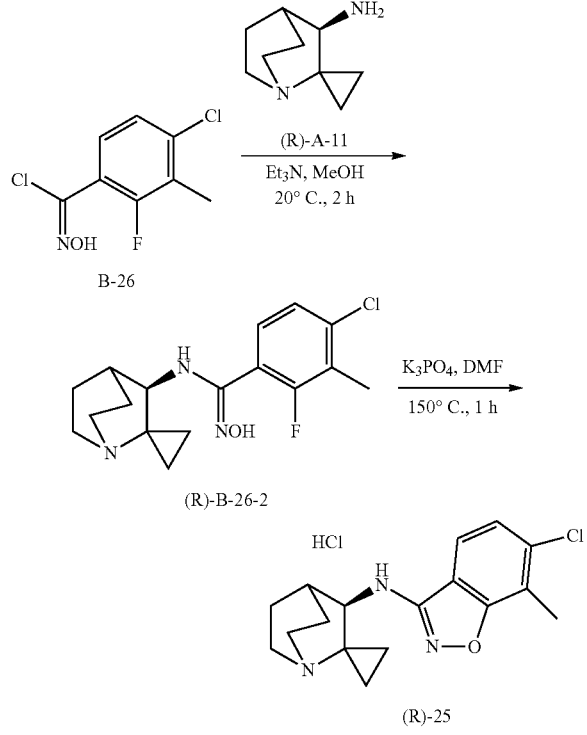

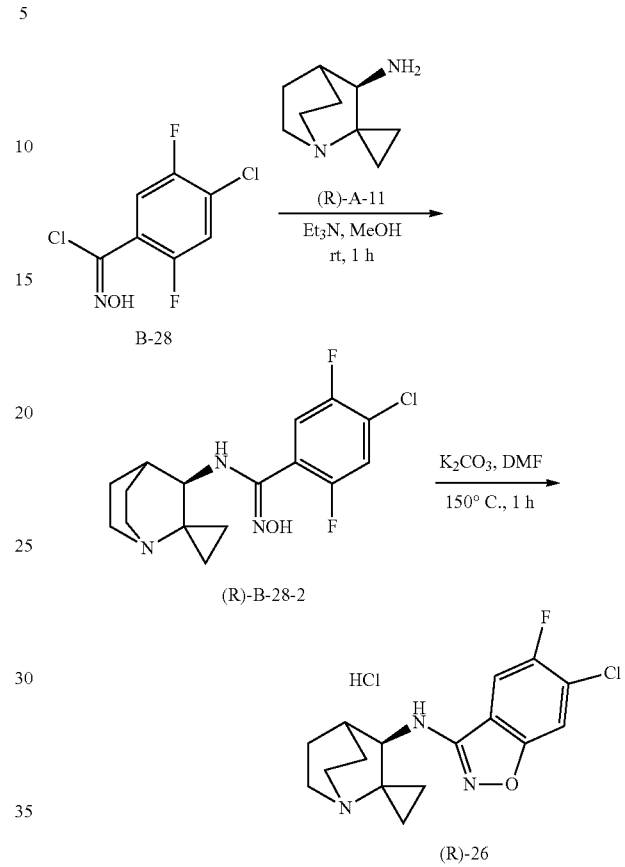

Following general procedure B1, compound (R)-25 was prepared from compound B-26:

Compound (R)-B-26-2 (0.12 g, white solid, 26% yield over two steps) was prepared from compound B-26 (0.30 g, 1.35 mmol) and (R)-A-11 (0.21 g, 1.35 mmol) with a reaction time of 2 hours and a reaction temperature of 20° C. The product was purified by prep-HPLC [Instrument: GX-C; Column: Phenomenex Gemini C18 250×50 mm, particle size: 10 μm; Mobile phase: 27-57% acetonitrile in $H_2O$ (add 0.05% ammonia, v/v)]. LCMS (J): ($ES^+$) m/z $(M+H)^+$= 307.1, tR=1.68 min.

A solution of compound (R)-B-26-2 (0.12 g, 0.33 mmol) and potassium phosphate (0.21 g, 0.98 mmol) in N,N-dimethylformamide (3.0 mL) was stirred at 150° C. for 1 hour. On completion, the reaction mixture was filtered and concentrated in vacuo. The residue was purified by prep-HPLC [Instrument: GX-C; Column: Phenomenex Gemini C18 250×50 mm, particle size: 10 μm; Mobile phase: 28-48% acetonitrile in $H_2O$ (add 0.05% TFA, v/v)]. The resulting solids was dissolved in 0.2 M hydrochloric acid solution and again lyophilized to give:

Compound (R)-25 (30 mg, 25% yield) as a white solid: cSFC analytical (D) tR=1.996 min., purity: 100.00%; LCMS (EE): tR=2.17 min., 318.1 m/z (M+1); 1H-NMR ($CD_3OD$, 400 MHz): δ 7.73 (d, J=8.4 Hz, 1H), 7.32 (d, J=8.4 Hz, 1H), 4.23-4.22 (m, 1H), 3.72-3.58 (m, 2H), 3.52-3.41 (m, 2H), 2.65-2.64 (m, 1H), 2.49 (S, 3H), 2.38-2.32 (m, 1H), 2.23-2.17 (m, 2H), 2.04-1.94 (m, 1H), 1.43-1.35 (m, 2H), 1.27-1.23 (m, 2H).

Following general procedure B1, compound (R)-26 was prepared from compound B-28:

Compound (R)-B-28-2 (0.20 g, white solid, 32% yield over two steps) was prepared from compound B-28 (0.40 g, 1.8 mmol) and (R)-A-11 (0.27 g, 1.8 mmol). The product was purified by prep-HPLC [Instrument: GX-H; Column: Phenomenex Synergi C18 150×25 mm, particle size: 10 μm; Mobile phase: 26-56% acetonitrile in $H_2O$ (add 0.5% $NH_3$ H2O, v/v)]. LCMS (J): ($ES^+$) m/z $(M+H)^+$=342.1, tR=1.206 min.

A solution of compound (R)-B-28-2 (0.18 g, 0.53 mmol) and potassium carbonate (0.22 g, 1.6 mmol) in N,N-dimethylformamide (5.0 mL) was stirred at 150° C. for 1 hour. On completion, the reaction mixture was filtered and concentrated in vacuo. The residue was purified by prep-HPLC [Instrument: GX-H; Column: Phenomenex Gemini C18 150×25 mm, particle size: 10 μm; Mobile phase: 40-70% acetonitrile in $H_2O$ (add 0.5% $NH_3$ H2O, v/v)]. The resulting solid was dissolved in 0.2 N hydrochloric acid and again lyophilized to give:

Compound (R)-26 (0.10 g, 53% yield) as a white solid: cSFC analytical (D) tR=1.776 min., purity: 98.06%; LCMS (GG): tR=2.086 min., 322.1 m/z (M+1); 1H-NMR ($CD_3OD$, 400 MHz): δ 7.84 (d, J=8.4 Hz, 1H), 7.67 (d, J=5.6 Hz, 1H), 4.21-4.21 (m, 1H), 3.68-3.41 (m, 4H), 2.66-2.63 (m, 1H), 2.37-2.31 (m, 1H), 2.23-2.18 (m, 2H), 2.00-1.95 (m, 1H), 1.46-1.35 (m, 2H), 1.27-1.23 (m, 2H).

Example 27: (R)-6-chloro-7-ethoxy-N-(1'-azaspiro[cyclopropane-1,2'-bicyclo[2.2.2]octan]-3'-yl)benzo[d]isoxazol-3-amine hydrochloride ((R)-27)

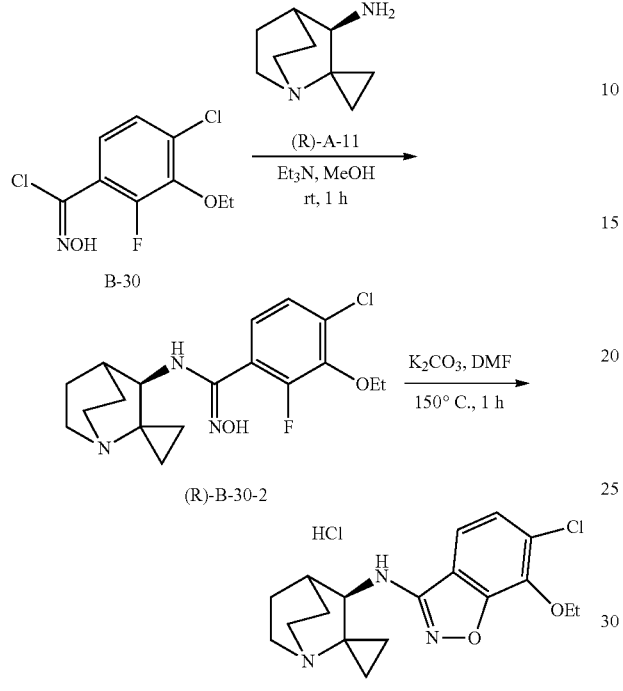

Example 28: (R)-7-chloro-6-methyl-N-(1'-azaspiro[cyclopropane-1,2'-bicyclo[2.2.2]octan]-3'-yl)benzo[d]isoxazol-3-amine hydrochloride ((R)-28)

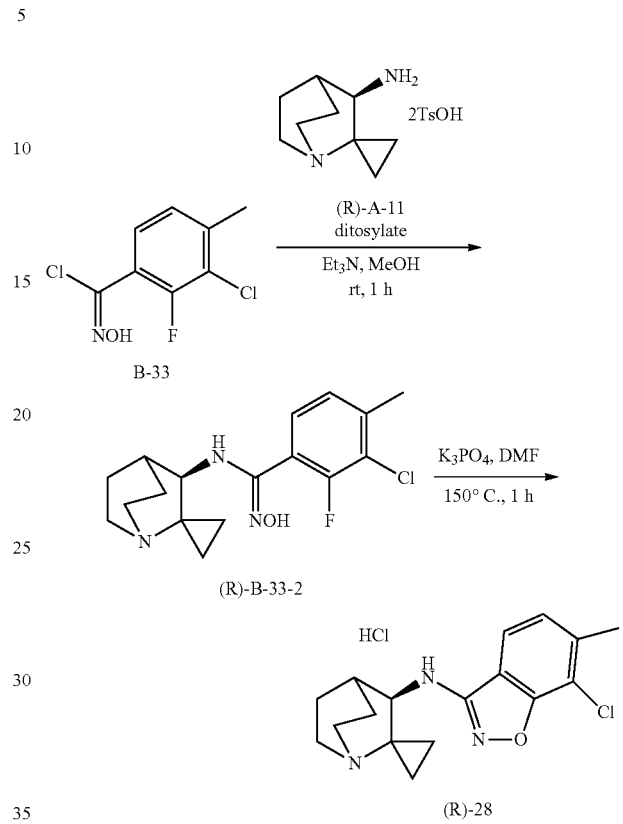

Following general procedure B1, compound (R)-27 was prepared from compound B-30:

Compound (R)-B-30-2 (0.20 g, white solid, 30% yield over two steps) was prepared from B-30 (0.50 g, 2.0 mmol) and compound (R)-A-11 (0.20 g, 1.3 mmol). The product was purified by prep-HPLC [Instrument: GX-A; Column: Phenomenex Gemini C18 250×50 mm, particle size: 10 μm; Mobile phase: 36-66% acetonitrile in $H_2O$ (add 0.5% $NH_3$ H2O, v/v)]. LCMS (J): ($ES^+$) m/z $(M+H)^+$=368.1, tR=1.264 min.

A solution of compound (R)-B-30-2 (0.20 g, 0.54 mmol) and potassium carbonate (0.15 g, 1.1 mmol) in N,N-dimethylformamide (5 mL) was stirred at 150° C. for 1 hour. On completion, the reaction mixture was filtered and concentrated in vacuo. The residue was purified by prep-HPLC [Instrument: GX-H; Column: Phenomenex Synergi C18 250×50 mm, particle size: 10 μm; Mobile phase: 50-80% acetonitrile in $H_2O$ (add 0.5% $NH_3$ H2O, v/v)]. The resulting solids was dissolved in 0.2 M hydrochloric acid solution and again lyophilized to give:

Compound (R)-27 (70 mg, 34% yield) as a white solid: cSFC analytical (D) tR=1.997 min., purity: 98.60%; LCMS (GG): tR=2.200 min., ($ES^+$) m/z $(M+H)^+$=348.1; 1H-NMR ($CD_3OD$, 400 MHz): δ 7.54 (dd, J=8.4 Hz, J=2.4 Hz, 1H), 7.30 (d, J=8.8 Hz, 1H), 4.46 (q, J=7.2 Hz, 2H), 4.22 (s, 1H), 3.71-3.58 (m, 2H), 3.52-3.33 (m, 2H), 3.65-3.64 (m, 1H), 2.37-2.31 (m, 1H), 2.23-2.20 (m, 2H), 2.02-1.95 (m, 1H), 1.45-1.36 (m, 5H), 1.27-1.22 (m, 2H).

Following general procedure B1, compound (R)-28 was prepared from compound B-33:

Compound (R)-B-33-2 (0.50 g, white solid, 69% yield over two steps) was prepared from B-33 (0.45 g, 2.0 mmol) and compound (R)-A-11 ditosylate (1.0 g, 2.0 mmol) with 5 equivalent of triethyl amine. The product was purified by prep-HPLC [Instrument: HPLC-A; Column: Phenomenex Synergi C18 250×50 mm, particle size: 10 μm; Mobile phase: 28-53% acetonitrile in $H_2O$ (add 0.05% $NH_3$ H2O, v/v)]. LCMS (J): ($ES^+$) m/z $(M+H)^+$=338.1, tR=1.228 min.

A solution of compound (R)-B-33-2 (150 mg, 0.44 mmol) and potassium phosphate (0.28 g, 1.3 mmol) in N,N-dimethylformamide (2.0 mL) was stirred at 150° C. for 1 hour. On completion, the reaction mixture was filtered and concentrated in vacuo. The residue was purified by prep-HPLC [Instrument: GX-B; Column: Welch Ultimate AQ C18 150×30 mm, particle size: 4 μm; Mobile phase: 30-60% acetonitrile in $H_2O$ (add 0.1% TFA, v/v)]. The resulting solid was dissolved in 0.2 N hydrochloric acid and again lyophilized to give:

Compound (R)-28 (40 mg, 25% yield) as a white solid: cSFC analytical (D) tR=2.293 min., purity: 99.76%; LCMS (GG): tR=2.13 min., 318.1 m/z (M+1); 1H-NMR ($CD_3OD$, 400 MHz): δ 7.78 (d, J=8.0 Hz, 1H), 7.24 (d, J=8.4 Hz, 1H), 4.21 (d, J=2.4 Hz, 1H), 3.69-3.45 (m, 4H), 2.66-2.63 (m, 1H), 2.51 (s, 3H), 2.36-2.30 (m, 1H), 2.21-2.16 (m, 2H), 1.97-1.94 (m, 1H), 1.44-1.36 (m, 2H), 1.28-1.17 (m, 2H).

Example 29: (R)-6-chloro-N-(1'-azaspiro[cyclopropane-1,2'-bicyclo[2.2.2]octan]-3'-yl)-7-(trifluoromethyl)benzo[d]isoxazol-3-amine hydrochloride ((R)-29)

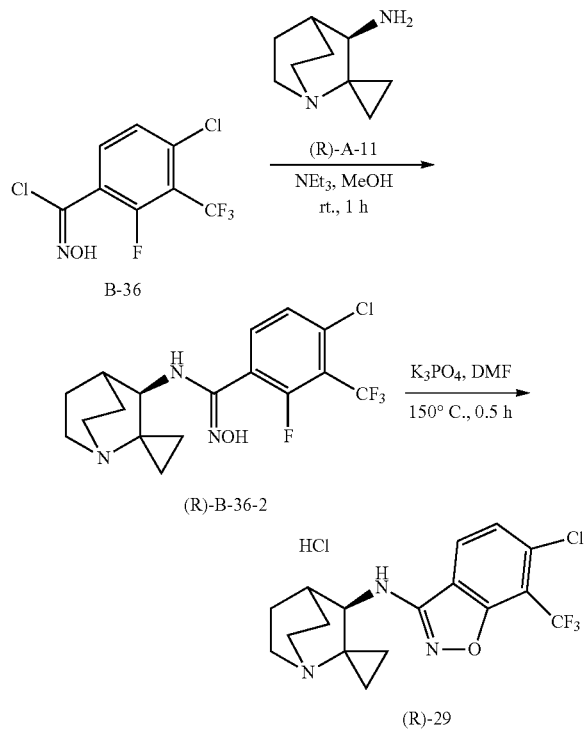

Following general procedure B1, compound (R)-29 was prepared from compound B-36:

Compound (R)-B-36-2 (0.26 g, white solid, 43% yield over 2 steps) was prepared from compound B-36 (0.50 g, 1.8 mmol) and (R)-A-11 (0.28 g, 1.8 mmol). The product was purified by prep-HPLC [Instrument: GX-C; Column: Phenomenex Gemini C18 250×50 mm; particle size: 10 m; Mobile phase: 38-68% acetonitrile in $H_2O$ (add 0.05% $NH_3$ H2O, v/v)]. LCMS (J): ($ES^+$) m/z (M+H)=392.1, tR=1.329.

A mixture of compound (R)-B-36-2 (0.15 g, 0.38 mmol) and potassium phosphate (0.24 g, 1.2 mmol) in N,N-dimethylformamide (20 mL) was stirred at 150° C. for 0.5 hour. On completion, the reaction mixture was filtered and concentrated in vacuo. The residue was purified by prep-HPLC [Instrument: GX-C; Column: Phenomenex Gemini C18 250×50 mm; particle size: 10 μm; Mobile phase: 45-75% acetonitrile in $H_2O$ (add 0.05% $NH_3$ H2O, v/v)]. The resulting solid was dissolved in 0.2 N hydrochloric acid and again lyophilized to give:

Compound (R)-29 (130 mg, 83% yield) as a white solid: cSFC analytical (D) tR=1.643 min., purity: 96.86%; LCMS (GG): tR=2.371 min., ($ES^+$) m/z (M+H)$^+$=302.1; $^1$H-NMR (CD$_3$OD, 400 MHz): δ 8.15 (d, J=8.4 Hz, 1H), 7.55 (d, J=8.4 Hz, 1H), 4.24 (d, J=2.4 Hz, 1H), 3.68-3.59 (m, 2H), 3.53-3.45 (m, 2H), 2.67-2.66 (m, 1H), 2.38-2.32 (m, 1H), 2.24-2.17 (m, 2H), 2.03-1.96 (m, 1H), 1.43-1.37 (m, 2H), 1.28-1.24 (m, 2H).

Example 30: (R)-6-chloro-7-isopropoxy-N-(1'-azaspiro[cyclopropane-1,2'-bicyclo[2.2.2]octan]-3'-yl)benzo[d]isoxazol-3-amine hydrochloride ((R)-30)

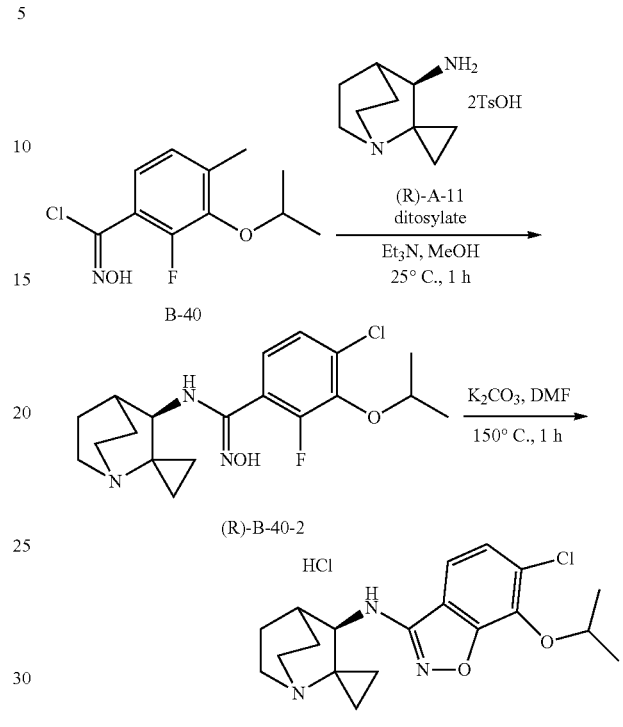

Following general procedure B1, compound (R)-30 was prepared from compound B-40:

Compound (R)-B-40-2 (0.40 g, white solid, 56% yield over two steps) was prepared from compound B-40 (0.50 g, 1.9 mmol) and compound (R)-A-11 di-tosylate (0.94 g, 1.9 mmol) using 4 equivalents of triethylamine. The product was purified by prep-HPLC [Instrument: GX-H; Column: Boston pH-lex 150×25 mm, particle size: 10 μm; Mobile phase: 40-70% acetonitrile in $H_2O$ (add 0.05% ammonia, v/v)]. LCMS (J): ($ES^+$) m/z (M+H)$^+$=382.1, tR=1.364 min.

A mixture of compound (R)-B-40-2 (0.20 g, 0.52 mmol) and potassium carbonate (0.22 g, 1.6 mmol) in N,N-dimethylformamide (5.0 mL) was stirred at 150° C. for 1 hour. On completion, the reaction mixture was filtered and concentrated in vacuo. The residue was purified by prep-HPLC [Instrument: GX-B; Column: Welch Ultimate AQ-C18 150×30 mm, particle size: 5 um; Mobile phase: 40-70% acetonitrile in water (0.1% TFA)-CAN]: The resulting solids were dissolved in 0.2 M hydrochloric acid solution and again lyophilized to give:

Compound (R)-30 (50 mg, 26% yield) as a white solid: cSFC analytical (D) tR=1.841 min., purity: 100%; LCMS (GG): tR=2.275 min., 362.2 m/z (M+1); 1H-NMR (CD$_3$OD, 400 MHz): δ 7.59 (d, J=8.8 Hz, 1H), 7.30 (d, J=8.8 Hz, 1H), 4.99-4.93 (m, 1H), 4.21 (d, J=2.4 Hz, 1H), 3.69-3.44 (m, 4H), 2.69-2.64 (m, 1H), 2.38-2.32 (m, 1H), 2.23-2.16 (m, 2H), 2.02-1.94 (m, 1H), 1.46-1.21 (m, 10H).

Crystallization Experiments

Example 31: (R)-2,2-dimethyl-N—((R)-1-phenyl-ethyl)quinuclidin-3-amine monofumarate ((R,R)-A-7 monofumarate)

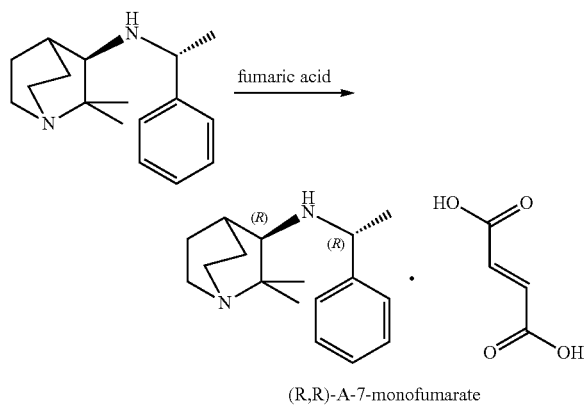

(R,R)-A-7-monofumarate

A solution of 2,2-dimethyl-N—((R)-1-phenylethyl)qui-nuclidin-3-amine (41 mg, 0.16 mmol, 1.6/98.4 mixture of diastereoisomers) in ethyl acetate was filtered through a 20 micron PTFE filter, concentrated and taken up in diethyl ether (4 mL). Next, a 0.8 M solution of fumaric acid in diethyl ether/methanol (9:1, v/v, 0.16 mmol, 2.0 mL) was added. An oily precipitate formed that turned into small needles. The mixture was concentrated and taken up in methanol (1 mL). Ethyl acetate (10 mL) was added, and the mixture was left to stand over weekend, during which time crystals formed. The solvent was decanted, and the crystals were washed with ethyl acetate (3×2 mL) and dried in vacuo to afford (R,R)-A-7 monofumarate (57 mg, 96% yield) as colorless crystals. 1H NMR (300 MHz, DMSO-$d_6$) δ 7.41-7.26 (m, 4H), 7.26-7.16 (m, 1H), 6.42 (s, 2H), 3.69 (q, J=6.5 Hz, 2H), 3.38-3.12 (m, 2H), 2.99-2.84 (m, 2H), 2.38-2.31 (m, 1H), 2.06-1.91 (m, 1H), 1.80-1.37 (m, 7H), 1.34 (s, 3H), 1.23 (d, J=6.6 Hz, 3H).

Single-crystal diffraction was performed on a Nonius KappaCCD single-crystal diffractometer using graphite monochromated Mo Kα radiation. During the measurement the crystal was cooled to −65° C. Diffraction images were integrated using Eval 14. Intensity data were corrected for Lorentz and polarization effects. A semi empirical multi scan absorption correction was applied (SADABS).

The structure was solved by SHELXT. This structure solution shows that the relative configuration of the bulk crystal is either (R,R) or (S,S) [and not (R,S) or (S,R)]. Refinement was performed with standard methods (refinement against F2 of all reflections with SHELXL97) with anisotropic displacement parameters for the non-hydrogen atoms. All hydrogen atoms were placed at calculated positions and refined riding on the parent atoms. The right enantiomer (the (R,R) versus the (S,S) form) was determined by careful examination of the Bijvoet pairs. This analysis showed that the vast majority of the crystal consists of the (R,R) form. Coordinate data from the X-ray analysis of the formed crystal of (R,R)-A-7 monofumarate are shown in Table 2, and its 3-D representation is shown in FIG. 1.

TABLE 2

X-ray Data:
Unit cell: 11.4272 12.7814 13.9040 90.000 90.000 90.000
Space group: P 21 21 21

| Atom | x | y | z |
|---|---|---|---|
| C1 | 0.382346 | 0.773501 | 0.978441 |
| H1 | 0.441086 | 0.824985 | 0.978134 |
| C2 | 0.389035 | 0.691661 | 1.042997 |
| H2 | 0.452287 | 0.687855 | 1.086078 |
| C3 | 0.303362 | 0.615194 | 1.044778 |
| H3 | 0.308259 | 0.559469 | 1.088714 |
| C4 | 0.210766 | 0.621504 | 0.981519 |
| H4 | 0.151757 | 0.570279 | 0.982616 |
| C5 | 0.204588 | 0.703345 | 0.916269 |
| H5 | 0.141569 | 0.706448 | 0.87291 |
| C6 | 0.289626 | 0.780722 | 0.913757 |
| C7 | 0.277321 | 0.871931 | 0.844143 |
| H7 | 0.227622 | 0.848412 | 0.789977 |
| C8 | 0.215153 | 0.963119 | 0.893086 |
| H8A | 0.260032 | 0.985387 | 0.948651 |
| H8B | 0.137825 | 0.941095 | 0.913533 |
| H8C | 0.208065 | 1.020869 | 0.848199 |
| N9 | 0.387075 | 0.91195 | 0.803634 |
| H09A | 0.428529 | 0.94322 | 0.851058 |
| C10 | 0.46518 | 0.834545 | 0.761719 |
| H10 | 0.464917 | 0.772012 | 0.803735 |
| C11 | 0.590972 | 0.877189 | 0.757592 |
| H11 | 0.610167 | 0.912196 | 0.819117 |
| C12 | 0.605827 | 0.954095 | 0.67511 |
| H12A | 0.68214 | 0.988741 | 0.679567 |
| H12B | 0.544643 | 1.007742 | 0.677811 |
| C13 | 0.596961 | 0.892436 | 0.580212 |
| H13A | 0.549106 | 0.93112 | 0.533774 |
| H13B | 0.67505 | 0.882408 | 0.552571 |
| N14 | 0.541888 | 0.788327 | 0.60147 |
| H14A | 0.525082 | 0.757863 | 0.544574 |
| C15 | 0.630396 | 0.723592 | 0.653638 |
| H15A | 0.696563 | 0.708187 | 0.611093 |
| H15B | 0.595231 | 0.657155 | 0.673706 |
| C16 | 0.673161 | 0.784434 | 0.742291 |
| H16A | 0.672575 | 0.738984 | 0.799054 |
| H16B | 0.753323 | 0.809268 | 0.731982 |
| C17 | 0.349716 | 0.877165 | 0.605596 |
| H17A | 0.271052 | 0.873601 | 0.631606 |
| H17B | 0.347983 | 0.859876 | 0.537681 |
| H17C | 0.38031 | 0.947384 | 0.613851 |
| C18 | 0.42793 | 0.799636 | 0.658441 |
| C19 | 0.367159 | 0.69317 | 0.659148 |
| H19A | 0.416303 | 0.642605 | 0.691936 |
| H19B | 0.353753 | 0.67037 | 0.593525 |
| H19C | 0.292837 | 0.698941 | 0.692432 |
| O20 | 0.534838 | 0.55045 | 0.500354 |
| O21 | 0.494626 | 0.700972 | 0.428969 |
| C22 | 0.508916 | 0.601753 | 0.429062 |
| C23 | 0.488106 | 0.548365 | 0.334472 |
| H23 | 0.44921 | 0.585217 | 0.28547 |
| C24 | 0.522344 | 0.451892 | 0.317715 |
| H24 | 0.565229 | 0.41667 | 0.365464 |
| C25 | 0.49606 | 0.396184 | 0.226392 |
| O26 | 0.544441 | 0.303217 | 0.223974 |
| H26 | 0.472243 | 0.766134 | 0.334473 |
| O27 | 0.437705 | 0.431251 | 0.163092 |

A large collection of crystals from the same batch was also analyzed with powder diffraction, in order to check the match between the crystal structure, obtained by single-crystal diffraction, with the characteristics of the whole batch of crystals. Powder diffraction was performed on a Bruker D8 Advance with a Vantec-1 detector with an effective angle of about 3 degrees with a step size of 0.0166 degrees. The pattern was measured in reflection mode in a Bragg-Brentano geometry using a Johansson monochromator with a focusing curved Ge 111 crystal. The diffraction pattern was measured at room temperature (20° C.) using monochromatic Cu Kalpha1 radiation in the range of 5-50 degrees 2theta with variable slits, resulting in a 12 mm constant footprint.

Combining SXRD and PXRD:

Using the data from single crystal diffraction a powder diffraction pattern was simulated with Cu Kalpha1 radiation in the range of 5-50 degrees 2theta with a step size of 0.02 degrees using Mercury software. Using the Bruker TOPAS software, for the calculated powder diffraction pattern the lattice cell parameters are adjusted to compensate for the temperature difference of Powder diffraction (20° C.) and the single crystal diffraction (−65° C.). Comparing the corrected calculated powder pattern with the measured powder pattern, we find an excellent fit leaving no measured diffraction peaks unassigned. Measuring extra diffraction peaks not corresponding to the corrected calculated powder pattern could indicate the presence of another chemical species/diastereomer [the (R,S) or (S,R) form]. If a significant/substantial amount of another diastereomer and/or species would be present, in a separate crystalline phase, this would most probably create new diffraction peaks, which we don't see. Therefore, there is no indication that a form different from the (R,R) form is present in the crystalline batch.

Example 32: (R)—N—((R)-1-phenylethyl)-1'-azaspiro[cyclopropane-1,2'-bicyclo[2.2.2]octan]-3'-amine bis(4-methylbenzenesulfonate) ((R,R)-A-13 bis(4-methylbenzenesulfonate))

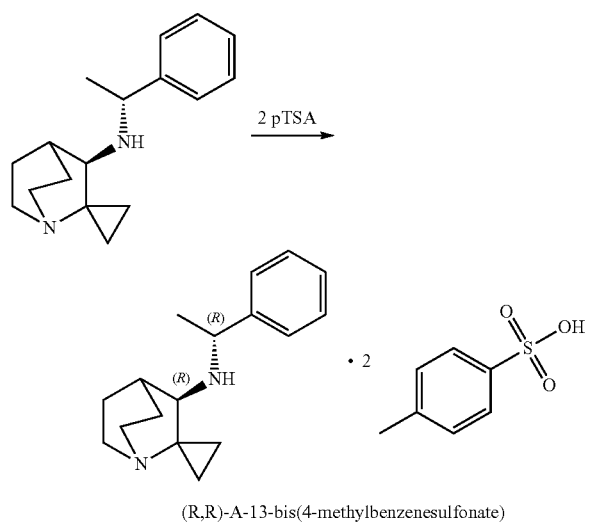

(R,R)-A-13-bis(4-methylbenzenesulfonate)

To a solution of N—((R)-1-phenylethyl)-1'-azaspiro[cyclopropane-1,2'-bicyclo[2.2.2]octan]-3'-amine (100 mg, 0.39 mmol, 1.6/98.4 mixture of diastereoisomers) in ethyl acetate was added dropwise a solution of p-toluenesulfonic acid monohydrate (148 mg, 0.78 mmol). The resulting suspension was heated to reflux, and methanol was added until the precipitate had almost completely dissolved. The mixture was allowed to cool to room temperature and left to stand over weekend. The solvent was decanted, and the crystals were washed with ethyl acetate (5 mL) and dried in vacuo to afford compound (R,R)-A-13 bis(4-methylbenzenesulfonate) (180 mg, 77% yield) as colorless crystals. 1H NMR (300 MHz, DMSO-d6) δ 9.46 (br s, 1H), 9.14 (br s, 1H), 8.83 (br s, 1H), 7.64-7.53 (m, 2H), 7.53-7.37 (m, 7H), 7.19-7.10 (m, 4H), 4.60-4.38 (m, 1H), 3.91-3.72 (m, 1H), 3.61-3.21 (m, 4H), 2.72-2.58 (m, 1H), 2.30 (s, 6H), 2.08-1.80 (m, 4H), 1.53 (d, J=6.3 Hz, 3H), 1.47-1.02 (m, 4H).

Figure 2:
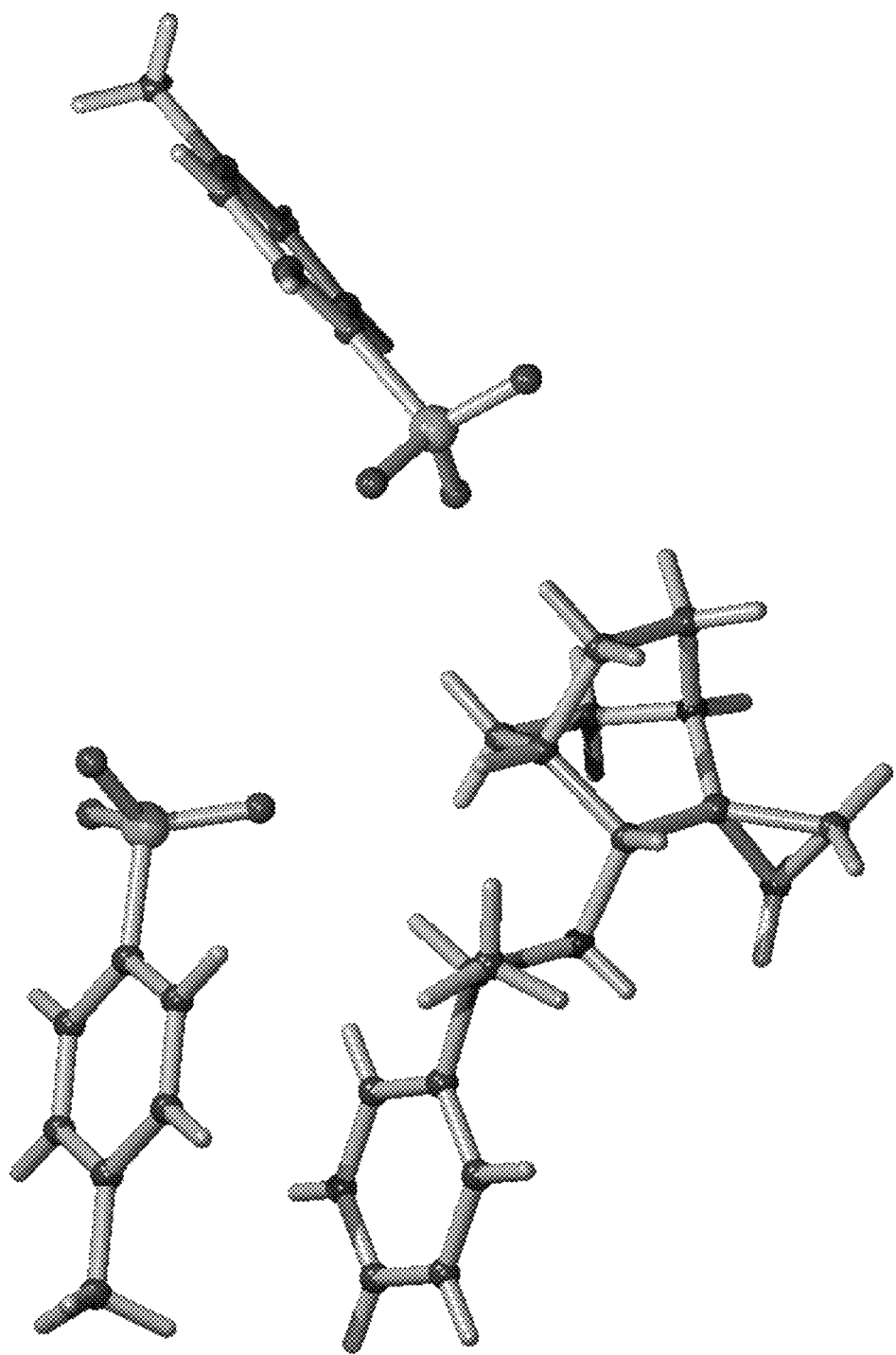
FIG. 2: Illustrates a 3-D representation of the formed crystal of (R)—N—((R)-1-phenylethyl)-1'-azaspiro[cyclopropane-1,2'-bicyclo[2.2.2]octan]-3'-amine bis(4-methylbenzenesulfonate).

Single crystal X-ray analysis of (R,R)-A-13 bis(4-methylbenzenesulfonate) was performed by the same technique as in Example 31. This analysis showed the absolute configuration to be (R,R) form. Coordinate data from the X-ray analysis of the formed crystal are shown in Table 3, and its 3-D representation is shown in FIG. 2.

TABLE 3

X-ray Data:
Unit cell: 6.3474 7.2244 16.0360 86.00 81.74 83.81
Space group P1

| | | | |
|---|---|---|---|
| C01 | 0.804341 | −0.177254 | 0.629535 |
| H01A | 0.698687 | −0.24098 | 0.606455 |
| H01B | 0.811861 | −0.205502 | 0.689765 |
| C02 | 1.008041 | −0.143845 | 0.573222 |
| H02A | 1.139692 | −0.151702 | 0.599133 |
| H02B | 1.026515 | −0.187182 | 0.51582 |
| C03 | 0.842241 | 0.015315 | 0.594449 |
| N04 | 0.71927 | 0.085105 | 0.524742 |
| H04 | 0.689495 | −0.019784 | 0.499645 |
| C05 | 0.84014 | 0.219849 | 0.466007 |
| H05A | 0.754593 | 0.270618 | 0.421916 |
| H05B | 0.974034 | 0.156197 | 0.438879 |
| C06 | 0.888221 | 0.378212 | 0.517515 |
| H06A | 1.042812 | 0.374087 | 0.51816 |
| H06B | 0.839124 | 0.498969 | 0.491477 |
| C07 | 0.502405 | 0.176995 | 0.559251 |
| H07A | 0.423689 | 0.088676 | 0.597585 |
| H07B | 0.419399 | 0.216624 | 0.512973 |
| C08 | 0.534685 | 0.345601 | 0.606488 |
| H08A | 0.461284 | 0.334961 | 0.664456 |
| H08B | 0.473046 | 0.459735 | 0.578721 |
| C09 | 0.773988 | 0.356413 | 0.60767 |
| H09 | 0.794689 | 0.463512 | 0.639888 |
| C10 | 0.875901 | 0.1761 | 0.647124 |
| H10 | 1.031592 | 0.185032 | 0.643218 |
| N11 | 0.788382 | 0.142702 | 0.738391 |
| H11A | 0.65707 | 0.09706 | 0.743984 |
| H11B | 0.865823 | 0.052082 | 0.759138 |
| C12 | 0.77872 | 0.308263 | 0.793704 |
| H12 | 0.675254 | 0.408674 | 0.774181 |
| C13 | 0.996841 | 0.381607 | 0.784542 |
| H13A | 0.998788 | 0.466616 | 0.828587 |
| H13B | 1.024981 | 0.446913 | 0.729781 |
| H13C | 1.106018 | 0.278118 | 0.789409 |
| C14 | 0.696056 | 0.245364 | 0.883823 |
| C15 | 0.478603 | 0.272261 | 0.911931 |
| H15 | 0.383874 | 0.324746 | 0.874724 |
| C16 | 0.832113 | 0.168243 | 0.939809 |
| H16 | 0.979931 | 0.149786 | 0.921508 |
| C17 | 0.754286 | 0.118007 | 1.022058 |
| H17 | 0.848507 | 0.064564 | 1.059281 |
| C18 | 0.400266 | 0.222081 | 0.994679 |
| H18 | 0.252585 | 0.23986 | 1.013349 |
| C19 | 0.53849 | 0.14626 | 1.049525 |
| H19 | 0.485334 | 0.113759 | 1.105808 |
| S40 | 0.498256 | 0.69953 | 0.398074 |
| O41 | 0.363831 | 0.556807 | 0.432234 |
| O42 | 0.5702 | 0.794389 | 0.463747 |
| O43 | 0.670496 | 0.637166 | 0.336137 |
| C44 | 0.335563 | 0.873233 | 0.346304 |
| C45 | 0.148375 | 0.832254 | 0.320669 |
| H45 | 0.102025 | 0.71279 | 0.332608 |
| C46 | 0.3997 | 1.050889 | 0.329127 |
| H46 | 0.527559 | 1.07927 | 0.346229 |
| C47 | 0.028371 | 0.968926 | 0.276979 |
| H47 | −0.097946 | 0.939998 | 0.25878 |
| C48 | 0.277841 | 1.186772 | 0.287149 |
| H48 | 0.321841 | 1.307413 | 0.277075 |
| C49 | 0.091987 | 1.146817 | 0.259878 |
| C50 | −0.041675 | 1.298321 | 0.215853 |
| H50A | −0.091455 | 1.397477 | 0.253841 |
| H50B | −0.163659 | 1.246965 | 0.199416 |
| H50C | 0.044225 | 1.347845 | 0.166019 |
| S55 | 0.29597 | 0.82788 | 0.785536 |
| O56 | 0.062941 | 0.851015 | 0.792039 |
| O57 | 0.393757 | 0.673164 | 0.736701 |
| O58 | 0.385583 | 1.00313 | 0.756908 |

TABLE 3-continued

| | | | |
|---|---|---|---|
| C60 | 0.3539 | 0.773904 | 0.889816 |
| C61 | 0.191446 | 0.767955 | 0.956468 |
| H61 | 0.048387 | 0.79671 | 0.947195 |
| C62 | 0.56471 | 0.732661 | 0.903811 |
| H62 | 0.676677 | 0.737724 | 0.858718 |
| C63 | 0.238985 | 0.719703 | 1.03692 |
| H63 | 0.127138 | 0.715798 | 1.082109 |
| C64 | 0.608063 | 0.684134 | 0.984687 |
| H64 | 0.751042 | 0.655036 | 0.99401 |
| C65 | 0.447722 | 0.677031 | 1.052338 |
| C66 | 0.50188 | 0.626002 | 1.140419 |
| H66A | 0.607394 | 0.704208 | 1.152632 |
| H66B | 0.559396 | 0.496191 | 1.144137 |
| H66C | 0.373575 | 0.644888 | 1.180964 |

Example 33: Human α7 nAChR Binding Assay

The ability of compounds to displace binding of radioactive ligands from human α7 nAChR was determined, as a measure of the affinity of the compounds for these ligand-gated ion channels. The [$^{125}$I]-αBungarotoxin competition binding assay was performed under contract by Cerep Poitiers, France following published the methods (Sharples et al., J Neurosci. 2000; 20(8):2783-91). "SH-SY5Y cells stably expressing human α7 nicotinic acetylcholine receptors, grown to confluency in 175 cm² flasks, were washed briefly with warm PBS containing (in mm): (150 NaCl, 8 K$_2$HPO$_4$, 2 KH$_2$PO$_4$, pH 7.4, 37° C.) and scraped into cold phosphate buffer. Cells were washed by centrifugation for 3 min at 500×g and resuspended in 10 mL of ice-cold phosphate buffer. The suspension was homogenized for 10 sec using an Ultraturax and centrifuged for 30 min at 45,000×g. The pellet was resuspended in phosphate buffer (0.5 mL per original flask). SH-SY5Y membranes (30 µg protein) were incubated in a total volume of 2 mL in 50 mM phosphate buffer with 0.05 nM [$^{125}$I]-αBgt and serial dilutions of test compound. Nonspecific binding was determined in the presence of α-bungarotoxin (1 µM). Samples were incubated for 120 min at 37° C. The reaction was terminated by filtration through Whatman GFA/E filter paper (presoaked overnight in 0.3% polyethyleneimine in PBS), using a Brandel Cell Harvester. Each condition was measured in duplicate. Filters were counted for radioactivity using a scintillation counter. The results were expressed as a percent inhibition of control specific binding obtained in the presence of the test compounds where Inhibition (%)=100–[(measured specific binding/control specific binding)×100].

The IC$_{50}$ values (concentration causing a half-maximal inhibition of control specific binding) and Hill coefficients (nH) were determined by non-linear regression analysis of the competition curves generated with mean replicate values using Hill equation:

$$Y = D + \left[\frac{A-D}{1+(C/C_{50})^{nH}}\right]$$

where Y=specific binding, A=left asymptote of the curve, D=right asymptote of the curve, C=compound concentration, $C_{50}$=IC$_{50}$, and nH=slope factor.

This analysis was performed using software developed at Cerep (Hill software) and validated by comparison with data generated by the commercial software SigmaPlot® 4.0 for Windows® (© 1997 by SPSS Inc.). The inhibition constants (K$_i$) were calculated using the Cheng Prusoff equation:

$$K_i = \frac{IC_{50}}{(1+L/K_D)}$$

where L=concentration of radioligand in the assay, and K$_D$=affinity of the radioligand for the receptor.

A scatchard plot is used to determine the K$_D$. Results are provided in Table 4 (reported as h-α7 Ki (µM)).

[$^3$H]BRL 43694 Competition Binding (h-5HT$_3$ Ki (µM))

[$^3$H]BRL 43694 competition binding assay was performed under contract by Cerep Poitiers, France following the methods described in Hope, A. G et al., "*Characterization of a human 5-hydroxytryptamine3 receptor type A (h5-HT3R-AS) subunit stably expressed in HEK 293 cells*," Brit. J. Pharmacol., (1996) 118: 1237-1245.

In brief, Chinese Hamster Ovary (CHO) cells stably expressing human 5-HT$_3$ serotonin receptors, grown to confluence in 175 cm² flasks. Following aspiration of the culture medium, cells were harvested by mechanical agitation in ice cold PBS containing (in mM): (150 NaCl, 8 K$_2$HPO$_4$, 2 KH$_2$PO$_4$, pH 7.4, 37° C.), centrifuged at 4,000 g for 10 min and subsequently stored as a cell pellet at −80 C. When required, the pellet was thawed and resuspended in ice cold homogenization buffer (Tris 50 mM, EGTA 5.0 mM, phenylmethylsulphonylfluoride 0.1 mM, pH 7.6) and homogenized. The homogenate was centrifuged at 48,000 g for 10 minutes at 40° C. The resulting pellet was resuspended in ice cold binding buffer comprising (in mM): NaCl 140, KCl 2.8, CaCl$_2$ 1.0; MgCl$_2$, 2.0; HEPES 10 (pH 7.4) and centrifuged as above. The pellet was resuspended in ice cold binding buffer and the protein concentration was determined by the method of Lowry et al., "*Protein measurement with the Folin phenol reagent*," J. Biol. Chem., (1953) 193, 265-275). The membrane homogenate was adjusted to a protein concentration of approximately 600 mg/mL in binding buffer. Assay tubes were loaded with equal volumes of binding buffer containing [$^3$H]BRL 43694 and test compound and 0.5 mL of membrane homogenate in a total reaction volume of 1 ml. Binding was initiated by the addition of the membrane homogenate and allowed to proceed for 120 min. at room temperature. Bound and free radioligand were separated by the addition of 3 ml of ice-cold binding buffer and immediate vacuum filtration through pre-soaked (0.1% (v/v) polyethyleneimine) Whatman GF/B filters. Filters were washed with a further 2×3 mL applications of binding buffer and counted for radioactivity using a scintillation counter.

The results were expressed as a percent inhibition of control specific binding obtained in the presence of the test compounds where Inhibition (%)=100–[(measured specific binding/control specific binding)×100].

The IC$_{50}$ values (concentration causing a half-maximal inhibition of control specific binding) and Hill coefficients (nH) were determined by non-linear regression analysis of the competition curves generated with mean replicate values using Hill equation $$Y = D + \left[\frac{A-D}{1+(C/C_{50})^{nH}}\right]$$

where Y=specific binding, A=left asymptote of the curve, D=right asymptote of the curve, C=compound concentration, $C_{50}$=IC$_{50}$, and nH=slope factor. This analysis was performed using software developed at Cerep (Hill software) and validated by comparison with data generated by the commercial software SigmaPlot® 4.0 for Windows® (© 1997 by SPSS Inc.).

The inhibition constants ($K_i$) were calculated using the Cheng Prusoff equation $$K_i = \frac{IC_{50}}{(1 + L/K_D)}$$

where L=concentration of radioligand in the assay, and $K_D$=affinity of the radioligand for the receptor.

A scatchard plot is used to determine the $K_D$. Results are provided in Table 4 (reported as h-5HT$_3$ Ki (µM)).

TABLE 4

| Compound | h- α7 $K_i$ (µM) | h-5HT$_3$ $K_i$ (µM) |
| --- | --- | --- |
| rac-1 | 0.11 | 2.7 |
| (R)-1 | 0.12 | 2.6 |
| (R)-2 | 0.1287 | 3.15 |
| (R)-3 | 0.15 | >10 |
| (R)-4 | 0.1087 | 0.13 |
| (R)-5 | 0.072 | 0.45 |
| (R)-6 | 0.135 | 3.5 |
| (R)-7 | 0.08 | 2.1 |
| (R)-8 | 0.195 | 0.1705 |
| (R)-9 | 0.63 | >10 |
| (R)-10 | 0.18 | 0.38 |
| (R)-11 | 0.28 | >10 |
| (R)-12 | 0.305 | >10 |
| (R)-13 | 0.18 | 0.15 |
| (R)-14 | 0.345 | >10 |
| (R)-15 | 0.41 | — |
| rac-16 | 0.05 | 1.8 |
| (R)-16 | 0.0747 | 1.6333 |
| (S)-16 | 1.7 | — |
| (R)-17 | 0.099 | 0.92 |
| (R)-18 | 0.1 | >10 |
| (R)-19 | 0.0745 | 0.1 |
| (R)-20 | 0.03 | 0.2 |
| (R)-21 | 0.235 | 1.6 |
| (R)-22 | 0.056 | 0.54 |
| (R)-23 | 0.23 | 0.11 |
| (R)-24 | 0.325 | 3.1 |
| (R)-25 | 0.09 | 0.17 |
| (R)-26 | 0.2 | 2.8 |
| (R)-27 | 0.17 | 5.6 |
| (R)-28 | 0.14 | 0.066 |
| (R)-29 | 0.37 | 4.3 |
| (R)-30 | 0.25 | — |

For reference, the literature reported α7 nAChR agonist AQW051 has a $K_i$ of 255 nM in the above described assay provided by Cerep (lit: $K_i$=28 nM; radioligand binding assay using recombinantly expressed human α7-nAChR and [$^{125}$I] α-BTX radioligand; Feuerbach et al., Br. J. Pharmacol., 2014, doi: 10.1111/bph.13001).

Example 34: Novel Object Recognition Task

The Novel Object Recognition (NOR) task is a behavioral assay commonly used to evaluate cognition, particularly recognition memory, in rodent models of CNS disorders. This test is based on the spontaneous tendency of rodents to spend more time exploring a novel object compared to a familiar one. The choice to explore the novel object reflects the use of learning and recognition memory. The assay is commonly used to evaluate potential therapeutic agents for Alzheimer's disease, other neurodegenerative diseases and psychiatric disorders.

Procedure:

Male Wistar rats (Harlan Laboratories) weighing 350-400 grams were housed under a reversed light cycle and are tested during the dark cycle. Testing was done under low lux conditions, measured to be ~2-7 lux under red light. Animals were habituated and weighed one day prior to testing. During habituation, animals were placed in a cylindrical arena and allowed to explore for 3 minutes. Training (T1) was conducted approximately 24 hours later, with one set of identical objects placed on opposite sides of the arena. Animals were allowed to explore the objects in 3-minute sessions. Animals were dosed with a designated treatment 15-60 minutes prior to testing depending on the pharmacokinetic profile of the compound before the start of T1. Drug or vehicle was dosed subcutaneously based on body weight at 5 mL/kg. Testing (T2) was done at 48 hours after T1. During testing, one familiar object is replaced with a novel object. Animals were allowed to explore both objects in 3-minute sessions.

Equipment Specification:

Animals were tracked using Noldus Ethovision XT (EthoVision XT version: 8.5, Noldus Inc. Wageningen, Netherlands) tracking software, using a 2 centimeter (cm) perimeter for each object as a separate zone. The test arena consisted of a cylinder, 80 cm diameter with 40 cm high walls of black acrylic that was opaque and matte. Objects were custom fabricated shapes (cone and bullet) similar in overall size (8 cm high×8 cm diameter) and were counterbalanced between treatment groups.

Data Analysis and Statistics:

Contact time was defined as the amount of time (seconds) an animal spent within the 2 cm perimeter of an object. All animals that had ≤5 seconds total contact time were excluded from the study. Statistical significance was determined using a Mann Whitney U-test and the criterion was set at p<0.05.

Results:

Natural forgetting in an object recognition task in male Wistar rats (n=4-20/group). Test compound was administered via sub-cutaneous administration 30 minutes before T1. Test compounds improved object recognition using a 48-hour retention interval (mean±SEM). *p<0.05=novel (N) vs. familiar (F) object. Results are illustrated in Table 5.

TABLE 5

| Compound | Active doses (mg/kg) |
| --- | --- |
| (R)-16 | 0.003, 0.01, 0.03 |

All publications and patent applications mentioned in this specification are herein incorporated by reference to the same extent as if each individual publication or patent application was specifically and individually indicated to be incorporated by reference.

While preferred embodiments of the present invention have been shown and described herein, it will be obvious to those skilled in the art that such embodiments are provided by way of example only. It is intended that the following claims define the scope of the invention and that methods and structures within the scope of these claims and their equivalents be covered thereby.

What is claimed is:

1. A compound represented by Formula (Ia) or Formula (Ib):

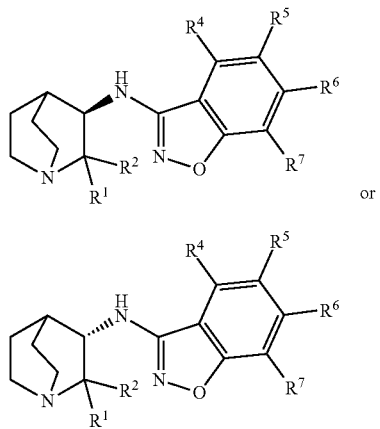

wherein:
- $R^1$ and $R^2$ independently represent an unbranched $C_1$-$C_4$-alkyl radical or a branched $C_3$-$C_4$-alkyl radical; or the $C(R^1)(R^2)$ moiety forms a (3-4 membered)-carbocycle, wherein $R^1$ and $R^2$ taken together represent a $C_2$-$C_3$-alkyl di-radical; wherein the unbranched $C_1$-$C_4$-alkyl radical, the branched $C_3$-$C_4$-alkyl radical, and the $C_2$-$C_3$-alkyl di-radical may be independently substituted with up to 4 radical substituents selected from the group consisting of: -D, —F, —Cl, —CN, —CH$_3$, —CH$_2$CH$_3$, =O, and —OR$^3$;
- $R^3$ independently represents —H; an unbranched $C_1$-$C_4$-alkyl radical; a branched $C_3$-$C_4$-alkyl radical; or a $C_3$-$C_4$-cycloalkyl radical; wherein the unbranched $C_1$-$C_4$-alkyl radical, the branched $C_3$-$C_4$-alkyl radical, and the $C_3$-$C_4$-cycloalkyl radical may be independently substituted with up to 4 radical substituents selected from the group consisting of: -D, —F, —Cl, —CN, =O, —OH, —OC$_1$-C$_4$-alkyl, and —OCF$_3$,
- $R^4$ and $R^5$ independently represent —H, -D, or halogen radical;
- $R^6$ independently represents —F, —Cl, —Br, —CN, —CH$_3$, —CH$_2$CH$_3$, cyclopropyl radical, —CHF$_2$, —CH$_2$F, —CF$_3$, —CH$_2$CF$_3$, —OCH$_3$, —OCH$_2$CH$_3$, —OCH(CH$_3$)$_2$, —O-cyclopropyl, or —OCF$_3$; and
- $R^7$ independently represents —H, -D, —F, —Cl, —CN, —CH$_3$, —CH(CH$_3$)$_2$, cyclopropyl radical, cyclobutyl radical, —CH$_2$F, —CHF$_2$, —CF$_3$, —CH$_2$CF$_3$, —OCH$_3$, —OH$_3$, —OCH$_2$CH$_3$, —OCH(CH$_3$)$_2$, —O-cyclopropyl, —OCF$_3$, or —OCH$_2$CF$_3$;

or a pharmaceutically acceptable salt thereof.

2. The compound of claim 1, wherein $R^6$ independently represents —F, —C, —CH$_3$, or —OCH$_3$.

3. The compound of claim 1, wherein $R^7$ independently represents —H, -D, —F, —C, —CH$_3$, or —OCH$_3$.

4. The compound of claim 1, wherein $R^4$ and $R^5$ independently represent —H or -D.

5. The compound of claim 1, wherein $R^6$ independently represents —Cl.

6. The compound of claim 5, wherein $R^7$ independently represents —H or -D.

7. The compound of claim 5, wherein $R^7$ independently represents —H, -D, or —F.

8. The compound of claim 1, wherein the compound is represented by Formula (Ia).

9. The compound of claim 8, wherein $R^1$ and $R^2$ independently represent an unbranched $C_1$-alkyl radical and said compound is represented by Formula (IIa):

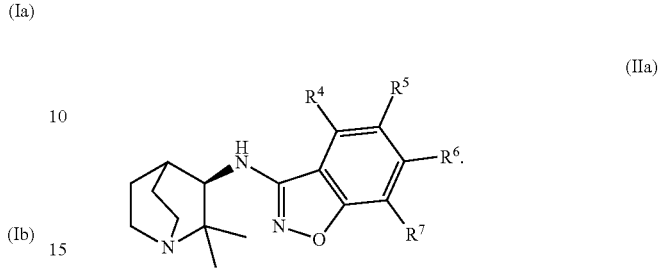

10. The compound of claim 1, wherein the compound is selected from the group consisting of:
- 6-chloro-N-(2,2-dimethylquinuclidin-3-yl)benzo[d]isoxazol-3-amine;
- 6-chloro-N-(2,2-dimethylquinuclidin-3-yl)-7-fluorobenzo[d]isoxazol-3-amine;
- N-(2,2-dimethylquinuclidin-3-yl)-6-methoxybenzo[d] isoxazol-3-amine;
- 6,7-dichloro-N-(2,2-dimethylquinuclidin-3-yl)benzo[d] isoxazol-3-amine;
- 6-chloro-N-(2,2-dimethylquinuclidin-3-yl)-7-methoxybenzo[d]isoxazol-3-amine;
- N-(2,2-dimethylquinuclidin-3-yl)-6-methylbenzo[d]isoxazol-3-amine;
- N-(2,2-dimethylquinuclidin-3-yl)-7-fluoro-6-methylbenzo[d]isoxazol-3-amine;
- 7-chloro-N-(2,2-dimethylquinuclidin-3-yl)-6-fluorobenzo[d]isoxazol-3-amine;
- N-(2,2-dimethylquinuclidin-3-yl)-5-fluoro-6-methylbenzo[d]isoxazol-3-amine;
- 6-chloro-N-(2,2-dimethylquinuclidin-3-yl)-7-methylbenzo[d]isoxazol-3-amine;
- 6-chloro-N-(2,2-dimethylquinuclidin-3-yl)-5-fluorobenzo[d]isoxazol-3-amine;
- 6-chloro-N-(2,2-dimethylquinuclidin-3-yl)-7-ethoxybenzo[d]isoxazol-3-amine;
- 7-chloro-N-(2,2-dimethylquinuclidin-3-yl)-6-methylbenzo[d]isoxazol-3-amine;
- 6-chloro-N-(2,2-dimethylquinuclidin-3-yl)-7-(trifluoromethyl)benzo[d]isoxazol-3-amine;
- 6-chloro-N-(2,2-dimethylquinuclidin-3-yl)-7-isopropoxybenzo[d]isoxazol-3-amine;
- 6-chloro-N-(1'-azaspiro[cyclopropane-1,2'-bicyclo[2.2.2]octan]-3'-yl)benzo[d]isoxazol 3-amine;
- 6-chloro-7-fluoro-N-(1'-azaspiro[cyclopropane-1,2'-bicyclo[2.2.2]octan]-3'-yl)benzo[d]isoxazol-3-amine;
- 6-methoxy-N-(1'-azaspiro[cyclopropane-1,2'-bicyclo[2.2.2]octan]-3'-yl)benzo[d]isoxazol-3-amine;
- 6,7-dichloro-N-(1'-azaspiro[cyclopropane-1,2'-bicyclo[2.2.2]octan]-3'-yl)benzo [d]isoxazol-3-amine;
- 6-chloro-7-methoxy-N-(1'-azaspiro[cyclopropane-1,2'-bicyclo[2.2.2] octan]-3'-yl)benzo[d]isoxazol-3-amine;
- 6-methyl-N-(1'-azaspiro[cyclopropane-1,2'-bicyclo[2.2.2]octan]-3'-yl)benzo[d]isoxazol-3-amine;
- 7-fluoro-6-methyl-N-(1'-azaspiro[cyclopropane-1,2'-bicyclo[2.2.2]octan]-3'-yl)benzo[d]isoxazol-3-amine;
- 7-chloro-6-fluoro-N-(1'-azaspiro[cyclopropane-1,2'-bicyclo[2.2.2]octan]-3'-yl)benzo[d]isoxazol-3-amine;
- 5-fluoro-6-methyl-N-(1'-azaspiro[cyclopropane-1,2'-bicyclo[2.2.2]octan]-3'-yl)benzo[d]isoxazol-3-amine;

6-chloro-7-methyl-N-(1'-azaspiro[cyclopropane-1,2'-bicyclo[2.2.2]octan]-3'-yl)benzo[d]isoxazol-3-amine;
6-chloro-5-fluoro-N-(1'-azaspiro[cyclopropane-1,2'-bicyclo[2.2.2]octan]-3'-yl)benzo[d]isoxazol-3-amine;
6-chloro-7-ethoxy-N-(1'-azaspiro[cyclopropane-1,2'-bicyclo[2.2.2]octan]-3'-yl)benzo[d]isoxazol-3-amine;
7-chloro-6-methyl-N-(1'-azaspiro[cyclopropane-1,2'-bicyclo[2.2.2]octan]-3'-yl)benzo[d]isoxazol-3-amine;
6-chloro-N-(1'-azaspiro[cyclopropane-1,2'-bicyclo[2.2.2]octan]-3'-yl)-7-(trifluoromethyl)benzo[d]isoxazol-3-amine; and
6-chloro-7-isopropoxy-N-(1'-azaspiro[cyclopropane-1,2'-bicyclo[2.2.2]octan]-3'-yl)benzo[d]isoxazol-3-amine;
and single enantiomers and pharmaceutically acceptable salts thereof.

11. The compound of claim 1, wherein the compound is selected from the group consisting of:
6-chloro-7-(difluoromethyl)-N-(1'-azaspiro[cyclopropane-1,2'-bicyclo[2.2.2]octan]-3'-yl)benzo[d]isoxazol-3-amine;
6-chloro-7-(difluoromethyl)-N-(2,2-dimethylquinuclidin-3-yl)benzo[d]isoxazol-3-amine;
6-chloro-N-(1'-azaspiro[cyclopropane-1,2'-bicyclo[2.2.2]octan]-3'-yl)-7-(trifluoromethoxy)benzo[d]isoxazol-3-amine;
6-chloro-N-(2,2-dimethylquinuclidin-3-yl)-7-(trifluoromethoxy)benzo[d]isoxazol-3-amine;
6-chloro-7-cyclopropoxy-N-(1'-azaspiro[cyclopropane-1,2'-bicyclo[2.2.2]octan]-3'-yl)benzo[d]isoxazol-3-amine;
6-chloro-7-cyclopropoxy-N-(2,2-dimethylquinuclidin-3-yl)benzo[d]isoxazol-3-amine;
6-chloro-N-(1'-azaspiro[cyclopropane-1,2'-bicyclo[2.2.2]octan]-3'-yl)-7-(2,2,2-trifluoroethyl)benzo[d]isoxazol-3-amine;
6-chloro-N-(2,2-dimethylquinuclidin-3-yl)-7-(2,2,2-trifluoroethyl)benzo[d]isoxazol-3-amine;
6-chloro-N-(1'-azaspiro[cyclopropane-1,2'-bicyclo[2.2.2]octan]-3'-yl)-7-(2,2,2-trifluoroethoxy)benzo[d]isoxazol-3-amine;
6-chloro-N-(2,2-dimethylquinuclidin-3-yl)-7-(2,2,2-trifluoroethoxy)benzo[d]isoxazol-3-amine;
6-chloro-7-isopropyl-N-(1'-azaspiro[cyclopropane-1,2'-bicyclo[2.2.2]octan]-3'-yl)benzo[d]isoxazol-3-amine; and
6-chloro-N-(2,2-dimethylquinuclidin-3-yl)-7-isopropylbenzo[d]isoxazol-3-amine;
and single enantiomers and pharmaceutically acceptable salts thereof.

12. The compound of claim 1, wherein the compound is selected from the group consisting of:
(R)-6-chloro-N-(2,2-dimethylquinuclidin-3-yl)benzo[d]isoxazol-3-amine;
(R)-6-chloro-N-(2,2-dimethylquinuclidin-3-yl)-7-fluorobenzo[d]isoxazol-3-amine;
(R)-6,7-dichloro-N-(2,2-dimethylquinuclidin-3-yl)benzo[d]isoxazol-3-amine;
(R)-6-chloro-N-(2,2-dimethylquinuclidin-3-yl)-7-methoxybenzo[d]isoxazol-3-amine;
(R)—N-(2,2-dimethylquinuclidin-3-yl)-6-methylbenzo[d]isoxazol-3-amine;
(R)-7-chloro-N-(2,2-dimethylquinuclidin-3-yl)-6-fluorobenzo[d]isoxazol-3-amine;
(R)-6-chloro-N-(2,2-dimethylquinuclidin-3-yl)-7-methylbenzo[d]isoxazol-3-amine;
(R)-6-chloro-N-(1'-azaspiro[cyclopropane-1,2'-bicyclo[2.2.2]octan]-3'-yl)benzo[d]isoxazol-3-amine;
(R)-6-methoxy-N-(1'-azaspiro[cyclopropane-1,2'-bicyclo[2.2.2]octan]-3'-yl)benzo[d]isoxazol-3-amine; and
(R)-7-fluoro-6-methyl-N-(1'-azaspiro[cyclopropane-1,2'-bicyclo[2.2.2]octan]-3'-yl)benzo[d]isoxazol-3-amine;
and pharmaceutically acceptable salts thereof.

13. A pharmaceutical composition, comprising:
i) the compound, or pharmaceutically acceptable salt thereof, of claim 1; and
ii) at least one pharmaceutically acceptable carrier, excipient or diluent.

* * * * *